US00RE49850E

(19) United States
(12) Reissued Patent
Wang et al.

(10) Patent Number: US RE49,850 E
(45) Date of Reissued Patent: Feb. 27, 2024

(54) N-(PYRIDIN-2-YL)-4-(THIAZOL-5-YL) PYRIMIDIN-2-AMINE DERIVATIVES AS THERAPEUTIC COMPOUNDS

(71) Applicant: AUCENTRA THERAPEUTICS PTY LTD, Adelaide (AU)

(72) Inventors: Shudong Wang, Adelaide (AU); Solomon Tadesse Zeleke, Adelaide (AU); Mingfeng Yu, Artarmon (AU)

(73) Assignee: AUCENTRA THERAPEUTICS PTY LTD, Adelaide (AU)

(21) Appl. No.: 17/591,158

(22) Filed: Feb. 2, 2022

Related U.S. Patent Documents

Reissue of:

(64) Patent No.: 10,479,785
Issued: Nov. 19, 2019
Appl. No.: 15/749,652
PCT Filed: Aug. 4, 2016
PCT No.: PCT/AU2016/000269
§ 371 (c)(1),
(2) Date: Feb. 1, 2018
PCT Pub. No.: WO2017/020065
PCT Pub. Date: Feb. 9, 2017

(30) Foreign Application Priority Data

Aug. 4, 2015 (AU) ..... 2015903106

(51) Int. Cl.
*C07D 417/14* (2006.01)
*A61P 35/02* (2006.01)

(52) U.S. Cl.
CPC ..... *C07D 417/14* (2013.01); *A61P 35/02* (2018.01)

(58) Field of Classification Search
CPC ..... C07D 417/14; A61P 35/02; A61P 35/00
See application file for complete search history.

(56) References Cited

U.S. PATENT DOCUMENTS 6,531,479 B2 * 3/2003 Wang ..... C07D 409/04 514/275
6,699,854 B2 * 3/2004 Wang ..... C07D 409/04 514/183
7,432,260 B2 * 10/2008 Wang ..... C07D 417/04 514/235.8
7,897,605 B2 * 3/2011 Wang ..... C07D 417/04 514/235.8
7,902,361 B2 * 3/2011 Wang ..... C07D 417/14 544/122
2002/0019404 A1 * 2/2002 Wang ..... C07D 409/04 514/256
2003/0149057 A1 * 8/2003 Wang ..... C07D 409/04 514/256
2005/0192300 A1 * 9/2005 Wang ..... C07D 417/04 514/269
2006/0241297 A1 * 10/2006 Wang ..... C07D 417/14 544/329
2007/0021452 A1 * 1/2007 Wang ..... C07D 417/04 514/275
2008/0287439 A1 * 11/2008 Wang ..... C07D 417/04 514/235.8
2008/0318954 A1 * 12/2008 Duncan ..... C07D 417/04 514/235.8
2009/0137572 A1 * 5/2009 Wang ..... C07D 417/04 514/227.8

FOREIGN PATENT DOCUMENTS

WO 01/72745 A1 10/2001
WO WO 01/72745 10/2001
WO WO-0172745 A1 * 10/2001 ..... C07D 409/04
WO 2007/054725 A2 5/2007
WO WO 2007/054725 5/2007
WO WO 2010/104899 9/2010
WO WO-2010104899 A1 * 9/2010 ..... C07D 417/04
WO 2013/156780 A1 10/2013
WO WO 2013/156780 10/2013
WO 2014/176210 A1 10/2014
WO WO 2014/176210 10/2014

OTHER PUBLICATIONS

Baker, et al., Genes & Cancer, 2012, 3, 658-669.
Bantie, et al., Gynecologic Oncology, 2020, 159, 827-838.
Barretina, et al., Nat. Genet., 2020, 42, 715-721.
Fernàndez, et al., J Clin Oncol, 2005, 23, 6364-6369.
Heine, et al., Jouranal of Hematology & Oncology, 2018, 11, 112.
International Search Report and Written Opinion for PCT/AU2016/000269, dated Oct. 20, 2016.
Italiano, et al., Clin Cancer Res. 2009, 15, 5696-5703.
Lee, et al., PLOS One, 2014, 9, e99452.
Malumbres, et al., Nature Reviews Cancer, 2001, 1, 222-231.
McLendon, et al., Nature, 2008, 1061-1068.
Ohgaki, et al., Cancer Research, 2004, 64, 6892-6899.
O'Leary, et al., Nat Rev Clin Oncol, 2016, 13, 417-430.
Patnaik, et al., Cancer Discovery, 2016, 6, 740-753.
Schmidt, et al., Cancer Research, 1994, 54, 6321-6324.
Sheppard, et al., Clin Cancer Res, 2013, 19, 5320-5328.
Yu, et al., Cancer Cell, 2006, 9, 23-32.
Zhao, et al., EBioMedicine, 2016, 8, 30-39.
Zuo, et al., Nat Genet, 1996, 12, 97-99.
International Search Report and Written Opinion dated Oct. 20, 2016, from International Application No. PCT/AU2016/000269, 10 pages.

* cited by examiner

*Primary Examiner* — Alan D Diamond
*Assistant Examiner* — Jerry D Johnson
(74) *Attorney, Agent, or Firm* — HUESCHEN AND SAGE

(57) ABSTRACT

A novel class of inhibitors of protein kinases that are useful in the treatment of cell proliferative diseases and conditions, and especially those characterised by over-expression of CDK4, CDK6 and/or cyclin D, including certain cancers of lung, breast, brain, central nervous system, colorectal cancer and leukaemias. The inhibitors have the general structure I:

I

12 Claims, 1 Drawing Sheet

N-(PYRIDIN-2-YL)-4-(THIAZOL-5-YL) PYRIMIDIN-2-AMINE DERIVATIVES AS THERAPEUTIC COMPOUNDS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

TECHNICAL FIELD

The present invention relates to a novel class of inhibitors of protein kinases useful in the treatment of proliferative cell diseases and conditions including cancers.

PRIORITY DOCUMENT

The present application is a 371 Application of International Application No PCT/AU2016/000269, filed 4 Aug. 2016, which claims priority from Australian Provisional Patent Application No 2015903106 titled "Novel kinase inhibitors II" filed on 4 Aug. 2015, the contents of which are hereby incorporated by reference in their entirety.

INCORPORATION BY REFERENCE

The following publication is referred to herein and its contents are hereby incorporated by reference in their entirety:

International Patent Application No PCT/GB2013/050982 (WO 2013/156780) titled "Therapeutic compounds" in the name of Changzhou Le Sun Pharmaceuticals Limited.

BACKGROUND

There is an ongoing need to identify and develop new compounds for treating proliferative diseases and conditions including cancers. Among the numerous "targets" for potential anti-proliferative compounds under investigation are the group of enzymes known as protein kinases.

Cyclin-dependent kinases (CDKs) are a type of protein kinase. They are known to be associated with various cyclin subunits, playing pivotal roles in the regulation of a variety of important regulatory pathways in cells, including cell-cycle control, apoptosis, neuronal physiology, differentiation and transcription. There are more than 20 CDKs which may be classified into two major groups, reflecting their functions; namely, the cell cycle regulator CDKs and the transcription regulator CDKs. The class of the cell cycle regulator CDKs includes CDK 1, CDK2, CDK3, CDK4 and CDK6, and they function with their cyclin partners (eg cyclin A, B, D1, D2, D3, E and F) to regulate promotion of the cell cycle. The class of the transcription regulator CDKs includes CDK7, CDK8, CDK9 and CDK 11, which work together with cyclin C, H, K, L1, L2, T1 and T2 and tend to play roles in transcriptional regulation. Given the functions of these two CDK classes, it is perhaps not surprising that CDKs have been implicated in cell proliferation diseases and conditions, particularly cancer. Cell proliferation is a result of the direct or indirect deregulation of the cell division cycle and the CDKs play a critical role in the regulation of the various phases of this cycle. Therefore, inhibitors of CDKs and their associated cyclins are considered to be useful targets for cancer therapy.

Certain pyrimidine-based compounds have been previously investigated for use in treating proliferative cell diseases and conditions including cancers, for example, 4-thiazol-2-pyridinylamino-pyrimidines and 5-substituted-4-thiazol-pyrimidines (see International patent publications WO 2005/012298 and WO2013/156780, respectively). These compounds inhibit multiple protein kinases, particularly CDKs, including CDK1/cyclin B, CDK2/cyclin E, CDK2/cyclin A, CDK4/cyclin D1, CDK7/cyclin H and CDK9/cyclin T1.

The present applicant has now identified a new class of thiazole-pyrimidine compounds for use in the prevention and/or treatment of proliferative diseases and conditions including cancers. While not wishing to be bound by theory, it is considered that these novel compounds are capable of inhibiting cell proliferation by inhibiting the activity of CDK4 and/or CDK6.

SUMMARY

According to a first aspect of the present invention, there is provided a compound of formula I shown below:

I

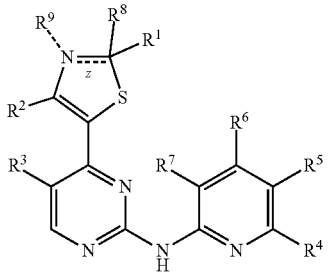

wherein:

z represents an optional bond such that the bond between N and the adjacent carbon atom can be a single or double bond;

$R^1$, $R^2$, $R^3$, $R^4$, $R^6$ and $R^7$ are each independently selected from the group consisting of H, alkyl, alkyl-$R^{10}$, aryl, aryl-$R^{10}$, aralkyl, aralkyl-$R^{11}$, halogen, $NO_2$, CN, $CF_3$, OH, O-alkyl, $COR^{10}$, $COOR^{10}$, O-aryl, O—$R^{10}$, $NH_2$, NH-alkyl, NH-aryl, N-$(alkyl)_2$, N-$(aryl)_2$, N-(alkyl)(aryl), NH—$R^{10}$, N—$(R^{10})(R^{11})$, N-(alkyl)($R^{10}$), N-(aryl)($R^{10}$), SH-alkyl, SH-aryl, S-$(alkyl)_2$, S-$(aryl)_2$, S-(alkyl)(aryl), SH—$R^{10}$, S—$(R^{10})(R^{11})$, S-(alkyl)($R^{10}$), S-(aryl)($R^{10}$), COOH, $CONH_2$, CONH-alkyl, CONH-aryl, CON-(alkyl)($R^{10}$), CON(aryl)($R^{10}$), CONH—$R^{10}$), CON—$(R^{10})(R^{11})$, $SO_3H$, $SO_2$-alkyl, $SO_2$-arlkyl-$R^{10}$, $SO_2$-aryl, $SO_2$-aryl-$R^{10}$, $SO_2NH_2$, $SO_2NH$—$R^{10}$, $SO_2N$—$(R^{10})(R^{11})$, $CF_3$, CO-alkyl, CO-alkyl-$R^{10}$, CO-aryl, CO-aryl-$R^{10}$ and $R^{12}$, wherein said alkyl, aryl and aralkyl groups may be optionally substituted with one or more groups selected from halogen, CN, OH, O-methyl, $NH_2$, COOH, $CONH_2$ and $CF_3$, and wherein when bond z is absent, $R^1$ is taken together with $R^8$ and is ═O or ═S;

$R^8$ is together with $R^1$═O or ═S when bond z is absent, or is not present when bond z is present;

$R^9$ is H, alkyl, aryl or heterocyclic group when bond z is absent, or is not present when bond z is present; and $R^{10}$, $R^{11}$ and $R^{12}$ are independently selected from water solubilising groups;

or a pharmaceutically acceptable salt, solvate or prodrug thereof.

In a second aspect, the present invention provides the use of a compound as defined in the first aspect or a pharmaceutically acceptable salt, solvate or prodrug thereof, for treating cancer or another proliferative cell disease or condition.

In a third aspect, the present invention provides a method of treating cancer or another proliferative cell disease or condition in a subject, the method comprising administering to said subject a therapeutically effective amount of a compound as defined in the first aspect or a pharmaceutically acceptable salt, solvate or prodrug thereof, optionally in combination with a pharmaceutically acceptable carrier, diluent and/or excipient.

In a fourth aspect, the present invention provides the use of a compound as defined in the first aspect, or a pharmaceutically acceptable salt, solvate or prodrug thereof, in the manufacture of a medicament for treating cancer or another proliferative cell disease or condition.

In a fifth aspect, the present invention provides a pharmaceutical composition or medicament comprising a compound as defined in the first aspect and a pharmaceutically acceptable carrier, diluent and/or excipient.

In a sixth aspect, the present invention provides a method for modulating protein kinase activity in a cell, comprising introducing to or contacting said cell with an effective amount of a compound as defined in the first aspect or a pharmaceutically acceptable salt, solvate or prodrug thereof.

DETAILED DESCRIPTION

Figure 1:
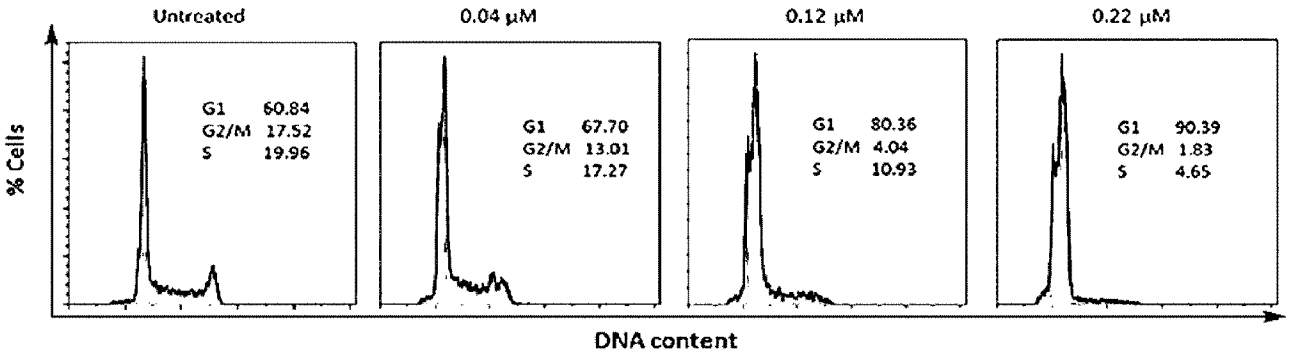
FIG. 1 provides graphical results of cell cycle analysis for a representative compound of the present invention (ie compound 60 described herein), wherein cells of the acute myeloid leukaemic cell line MV4-11 were treated 60 for 24 hours at the concentrations shown.

The present applicant has now identified a new class of 4-thiazol-N-(pyridin-2-yl)pyrimidin-2-amine derivatives suitable for use in the prevention and/or treatment of proliferative cell diseases and conditions including cancers, which possess desirable biological activity (eg the compounds may inhibit cell proliferation by inhibiting the activity of CDK4 and/or CDK6).

In a first aspect, the present invention provides a compound of formula I shown below:

I

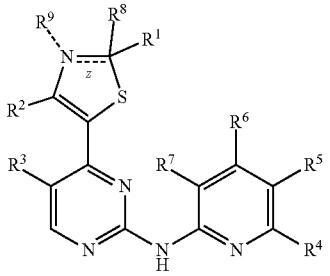

wherein:

z represents an optional bond such that the bond between N and the adjacent carbon atom can be a single or double bond;

$R^1$, $R^2$, $R^3$, $R^4$, $R^5$, $R^6$, and $R^7$ are each independently selected from the group consisting of H, alkyl, alkyl-$R^{10}$, aryl, aryl-$R^{10}$, aralkyl, aralkyl-$R^{11}$, halogen, $NO_2$, CN, $CF_3$, OH, O-alkyl, $COR^{10}$, $COOR^{10}$, O-aryl, O—$R^{10}$, $NH_2$, NH-alkyl, NH-aryl, N-$(alkyl)_2$, N-$(aryl)_2$, N-(alkyl)(aryl), NH—$R^{10}$, N—$(R^{10})(R^{11})$,)N-(alkyl)($R^{10}$), N-(aryl)($R^{10}$), SH-alkyl, SH-aryl, S-$(alkyl)_2$, S-$(aryl)_2$, S-(alkyl)(aryl), SH—$R^{10}$, S—$(R^{10})(R^{11})$, S-(alkyl)($R^{10}$), S-(aryl)($R^{10}$), COOH, $CONH_2$, CONH-alkyl, CONH-aryl, CON-(alkyl)($R^{10}$), CON(aryl)($R^{10}$), CONH—$R^{10}$, CON—$(R^{10})(R^{11})$, $SO_3H$, $SO_2$-alkyl, $SO_2$-alkyl-$R^{10}$, $SO_2$-aryl, $SO_2$-aryl-$R^{10}$, $SO_2NH_2$, $SO_2NH$—$R^{10}$, $SO_2N$—$(R^{10})(R^{11})$, $CF_3$, CO-alkyl, CO-alkyl-$R^{10}$, CO-aryl, CO-aryl-$R^{10}$ and $R^{12}$, wherein said alkyl, aryl and aralkyl groups may be optionally substituted with one or more groups selected from halogen, CN, OH, O-methyl, $NH_2$, COOH, $CONH_2$ and $CF_3$, and wherein when bond z is absent, $R^1$ is taken together with $R^8$ and is =O or =S;

$R^8$ is together with $R^1$=O or =S when bond z is absent, or is not present when bond z is present;

$R^9$ is H, alkyl, aryl or heterocyclic group when bond z is absent, or is not present when bond z is present; and $R^{10}$, $R^{11}$ and $R^{12}$ are independently selected from water solubilising groups;

or a pharmaceutically acceptable salt, solvate or prodrug thereof.

In some embodiments, the compounds of formula I may preferably comprise at least one water solubilising group $R^{10}$, $R^{11}$ or $R^{12}$. That is, in such embodiments, the compound is as defined above in paragraph [0018] with the proviso that said compound comprises at least one of said $R^{10}$, $R^{11}$ and $R^{12}$ groups. The present applicant has found that notwithstanding the addition of such solubilising group(s), the compounds possess desirable biological activity (eg by inhibiting the activity of CDK4 and/or CDK6). The presence of at least one water solubilising group may enhance in vivo absorption and oral bioavailability.

The compounds of formula I have been found to possess anti-proliferative activity and are therefore considered to be of use in the treatment of proliferative cell diseases and conditions such as cancer, leukaemia, lymphoma and other diseases and conditions associated with uncontrolled cell proliferation (or, in other words, requires control of the cell cycle) such as, for example, some cardiovascular diseases or conditions such as restenosis and cardiomyopathy, some auto-immune diseases such as glomerulonephritis and rheumatoid arthritis, dermatological conditions such as psoriasis, and fungal or parasitic disorders. As used herein, an anti-proliferative effect within the scope of the present invention may be demonstrated by the ability to inhibit cell proliferation in an in vitro whole cell assay. These assays, including methods for their performance, are described in more detail in the examples provided hereinafter.

The compounds of formula I may inhibit any of the steps or stages in the cell cycle, for example, formation of the nuclear envelope, exit from the quiescent phase of the cell cycle (G0), G1 progression, chromosome decondensation, nuclear envelope breakdown, START, initiation of DNA replication, progression of DNA replication, termination of DNA replication, centrosome duplication, G2 progression, activation of mitotic or meiotic functions, chromosome condensation, centrosome separation, microtubule nucleation, spindle formation and function, interactions with microtubule motor proteins, chromatid separation and segregation, inactivation of mitotic functions, formation of contractile ring, and cytokinesis functions. In particular, the compounds of formula I may influence certain gene functions such as chromatin binding, formation of replication complexes, replication licensing, phosphorylation or other secondary modification activity, proteolytic degradation, microtubule binding, actin binding, septin binding, microtubule organising centre nucleation activity and binding to components of cell cycle signalling pathways.

Thus, in a second aspect, the present invention provides the use of a compound as defined in the first aspect or a pharmaceutically acceptable salt, solvate or prodrug thereof, for treating cancer or another proliferative cell disease or condition.

In a third aspect, the present invention provides a method of treating cancer or another proliferative cell disease or condition in a subject, the method comprising administering to said subject a therapeutically effective amount of a compound as defined in the first aspect or a pharmaceutically acceptable salt, solvate or prodrug thereof, optionally in combination with a pharmaceutically acceptable carrier, diluent and/or excipient.

In a fourth aspect, the present invention provides the use of a compound as defined in the first aspect, or a pharmaceutically acceptable salt, solvate or prodrug thereof, in the manufacture of a medicament for treating cancer or another proliferative cell disease or condition.

In a fifth aspect, the present invention provides a pharmaceutical composition or medicament comprising a compound as defined in the first aspect and a pharmaceutically acceptable carrier, diluent and/or excipient.

In a sixth aspect, the present invention provides a method for modulating protein kinase activity in a cell, comprising introducing to or contacting said cell with an effective amount of a compound as defined in the first aspect or a pharmaceutically acceptable salt, solvate or prodrug thereof.

In this specification, a number of terms are used which are well known to those skilled in the art. Nevertheless, for the purposes of clarity, a number of these terms are hereinafter defined.

As used herein, the term "treating" includes prophylaxis as well as the alleviation of established symptoms of a condition. As such, the act of "treating" a disease or condition therefore includes: (1) preventing or delaying the appearance of clinical symptoms of the disease or condition developing in a subject afflicted with or predisposed to the disease or condition; (2) inhibiting the disease or condition (ie arresting, reducing or delaying the development of the disease or condition or a relapse thereof (in case of a maintenance treatment) or at least one clinical or subclinical symptom thereof and (3) relieving or attenuating the disease or condition (ie causing regression of the disease or condition or at least one of its clinical or subclinical symptoms).

As used herein, the term "alkyl" includes both straight chain and branched alkyl groups having from 1 to 8 carbon atoms (eg methyl, ethyl propyl, isopropyl, butyl, isobutyl, tert-butyl, pentyl, hexyl etc).

As used herein, the term "aryl" refers to a substituted (mono- or poly-) or unsubstituted monoaromatic or polyaromatic group, wherein said polyaromatic group may be fused or unfused. The term therefore includes groups having from 6 to 10 carbon atoms (eg phenyl, naphthyl etc). It is also to be understood that the term "aryl" is synonymous with the term "aromatic".

As used herein, the term "aralkyl" is used as a conjunction of the terms alkyl and aryl as defined above.

As used herein, the tern "alicyclic" refers to a cyclic aliphatic group.

The term "aliphatic" takes its normal meaning in the art and includes non-aromatic groups such as alkanes, alkenes and alkynes and substituted derivatives thereof.

The term "halogen" refers to fluoro, chloro, bromo and iodo.

As used herein, the term "heterocyclic" refers to a saturated or unsaturated cyclic group comprising one or more heteroatoms in the ring.

The term "derivative" as used herein, includes any chemical modification of an entity. Illustrative of such chemical modifications is the replacement of hydrogen by a halogen group, an alkyl group, an acyl group or an amino group.

As used herein, the phrase "manufacture of a medicament" includes the use of one or more of the compounds of formula I directly as the medicament or in any stage of the manufacture of a medicament comprising one or more of the compounds of formula I.

Some of the compounds of formula I may exist as single stereoisomers, racemates, and/or mixtures of enantiomers and/or diastereomers. All such single stereoisomers, racemates and mixtures thereof, are encompassed within the scope of the present invention. The isomeric forms such as diastereomers, enantiomers, and geometrical isomers can be separated by physical and/or chemical methods known to those skilled in the art.

The term "pharmaceutically acceptable salt" as used herein, refers to salts that retain the desired biological activity of the compounds of formula I, and include pharmaceutically acceptable acid addition salts and base addition salts. Suitable pharmaceutically acceptable acid addition salts of the compounds of formula I may be prepared from an inorganic acid or from an organic acid. Examples of such inorganic acids are hydrochloric, sulfuric and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic and arylsulfonic. Additional information on pharmaceutically acceptable salts can be found in Remington's Pharmaceutical Sciences, 19th Edition, Mack Publishing Co., Easton, Pa. 1995.

In the case of compounds of formula I that are solid, it will be understood by those skilled in the art that the compounds (or pharmaceutically acceptable salts, solvates or prodrugs thereof) may exist in different crystalline or polymorphic forms, all of which are encompassed within the scope of the present invention.

"Prodrug" means a compound that undergoes conversion to a compound of formula I within a biological system, usually by metabolic means (eg by hydrolysis, reduction or oxidation). For example, an ester prodrug of a compound of formula I containing a hydroxyl group may be convertible by hydrolysis in vivo to the compound of formula I. Suitable esters of the compounds of formula I containing a hydroxyl group may be, for example, acetates, citrates, lactates, tartrates, malonates, oxalates, salicylates, propionates, succinates, fumarates, maleates, methylene-bis-P-hydroxynaphthoates, gestisates, isethionates, di-p-toluoyltartrates, methanesulfonates, ethanesulfonates, benzenesulfonates, p-toluenesulfonates, cyclohexylsulfamates and quinates. As another example, an ester prodrug of a compound of formula I containing a carboxy group may be convertible by hydrolysis in vivo to the compound of formula I. Examples of ester prodrugs include those described by Leinweber F J, Drug Metab Rev 18:379-439 (1987). Similarly, an acyl prodrug of a compound of formula I containing an amino group may be convertible by hydrolysis in vivo to the compound of formula I. Examples of prodrugs for these and other functional groups, including amines, are provided in Prodrugs: challenges and rewards, Valentino J Stella (ed), Springer, 2007.

The term "therapeutically effective amount" or "effective amount" is an amount sufficient to effect beneficial or desired clinical results. A therapeutically effective amount can be administered in one or more administrations. Typically, a therapeutically effective amount is sufficient for treating a disease or condition or otherwise to palliate, ameliorate, stabilise, reverse, slow or delay the progression of a disease or condition such as, for example, cancer or another proliferative cell disease or condition. By way of example only, a therapeutically effective amount of a compound of formula I, or a pharmaceutically acceptable salt, solvate or prodrug thereof, may comprise between about 0.1 and about 250 mg/kg body weight per day, more preferably between about 0.1 and about 100 mg/kg body weight per day and, still more preferably between about 0.1 and about 25 mg/kg body weight per day. However, notwithstanding the above, it will be understood by those skilled in the art that the therapeutically effective amount may vary and depend upon a variety of factors including the activity of the particular compound (or salt, solvate or prodrug thereof), the metabolic stability and length of action of the particular compound (or salt, solvate or prodrug thereof), the age, body weight, sex, health, route and time of administration, rate of excretion of the particular compound (or salt, solvate or prodrug thereof), and the severity of, for example, the cancer or other proliferative cell disease or condition to be treated.

The compounds of formula I, and pharmaceutically acceptable salts, solvates and prodrugs thereof, are capable of inhibiting protein kinases, especially CDKs and may show higher selectivity (to inhibit) CDK4 and/or CDK6 over other protein kinases. As mentioned above, CDK4 and CDK6 promote cancer cell proliferation. As such, the compounds of formula I, and pharmaceutically acceptable salts, solvates and prodrugs thereof, which are believed to inhibit CDK4 and/or CDK6, have utility in both in vitro and in vivo applications (eg in vitro cell-based assays) and as the basis of a therapeutic method of treating cancer or another proliferative cell disease or condition in a subject.

The compounds of formula I bear a thiazole group attached to the pyrimidine ring through one of the ring carbon atoms (particularly, the carbon at position 4).

The compounds of formula I may bear at least one water solubilising group (eg provided by $R^{10}$, $R^{11}$ and/or $R^{12}$). The term "water solubilising group" will be well understood by those skilled in the art as referring to any polar functional group which either ionises or is capable of forming hydrogen bonds with water molecules to increase the water solubility of the compound (ie relative to the water solubility of the corresponding compound lacking the water solubilising group). Examples of suitable water solubilising groups and methods and considerations for their introduction are described in, for example, Fundamentals of Medicinal Chemistry by Gareth Thomas (publisher: John Wiley & Sons).

Preferably, where present, $R^{10}$ and $R^{11}$ are independently selected from water solubilising groups of the group consisting of:

(i) mono-, di- and poly-hydroxylated alicyclic groups, di- or poly-hydroxylated aliphatic or aryl groups, N-, O- and/or S-containing heterocyclic groups substituted with one or more hydroxyl or amino groups, aliphatic and aryl groups comprising one or more carboxamide, sulfoxide, sulfone or sulfonamide groups, and halogenated alkylcarbonyl groups; and ii) COOH, $SO_3H$, $OSO_3H$, $PO_3H_2$ and $OPO_3H_2$.

Preferably, where present, $R^{12}$ is selected from water solubilising groups of the group consisting of:

(i) mono-, di- and poly-hydroxylated alicyclic groups, di- or poly-hydroxylated aliphatic or aryl groups; N-, O- and/or S-containing heterocyclic groups substituted with one or more hydroxyl or amino groups, aliphatic and aryl groups comprising one or more carboxamide, sulfoxide, sulfone or sulfonamide groups; and halogenated alkylcarbonyl groups;

(ii) COOH, $SO_3H$, $OSO_3H$, $PO_3H_2$ and $OPO_3H_2$;

(iii) $NHCO(CH_2)_m[NHCO(CH_2)_{m'}]_p[NHCO(CH_2)_{m''}]_qY$ and $NHCO(CH_2)_tNH(CH_2)_{t'}Y$ wherein p and q are each independently selected from integers 0 or 1, and m, m', m", t and ' are each independently selected from integers 1 to 10, and Y is selected from:

(a) alicyclic, aryl and heterocyclic groups comprising one or more O—, S— or N— heteroatoms, which may further comprise an alkyl bridge (eg a —$CH_2$— or —$CH_2CH_2$— bridge), (b) alicyclic groups comprising one or more of —O—, $NH_2$, —NH—, =N—, quaternary amine salt, and amidine, and (c) morpholine, piperazine or 1,4-diazepane groups, each of which may be optionally substituted by one or more substituents selected from $SO_2$-alkyl, alkyl optionally substituted by one or more OH groups, CO-alkyl, aralkyl, COO-alkyl, and an ether group optionally substituted by one or more OH groups;

(iv) $(CH_2)_nNR^{13}COR^{14}$, $(CH_2)_{n'}NR^{13}SO_2R^{14}$ and $SO_2R^{15}$, wherein $R^{13}$ is selected from H and alkyl, $R^{14}$ and $R^{15}$ are each independently selected from alkyl groups optionally comprising one or more heteroatoms and/or optionally substituted with one or more substituents independently selected from OH, $NH_2$, halogen and $NO_2$, and n and n' are each independently selected from integers 0, 1, 2 and 3;

(v) ether and polyether groups optionally substituted with one or more OH groups or one or more Y groups, wherein Y is as defined above at (iii);

(vi) $(CH_2)_rNH_2$, wherein r is selected from integers 0, 1, 2 and 3;

(vii) $(CH_2)_{r'}OH$, wherein r' is selected from integers 0, 1, 2 and 3;

(viii) $(CH_2)_{n''}NR^{16}COR^{17}$, wherein $R^{16}$ is H or alkyl, n" is selected from integers 0, 1, 2 and 3, and $R^{17}$ is an aryl group optionally substituted with one or more substituents selected from halogen, $NO_2$, OH, alkoxy, $NH_2$, COOH, $CONH_2$ and $CF_3$; and (ix) $SO_2NR^{18}R^{19}$, wherein $R^{18}$ and $R^{19}$ are each independently selected from H, alkyl and aryl, with the proviso that at least one of $R^{18}$ and $R^{19}$ is other than H, or $R^{18}$ and $R^{19}$ together form a cyclic group optionally comprising one or more heteroatoms selected from N, O and S, and wherein said alkyl, aryl or cyclic group is optionally substituted by one or more substituents selected from halogen, $NO_2$, OH, alkoxy, $NH_2$, COOH, CONH, and $CF_3$.

In some embodiments, the compound is of the formula II shown below:

II

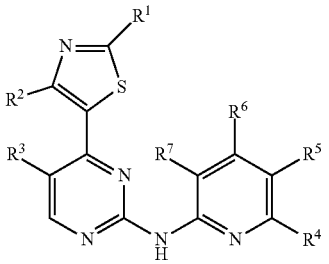

wherein $R^1$, $R^2$, $R^3$, $R^4$, $R^5$, $R^6$ and $R^7$ are as defined above for formula I.

In some embodiments, the compound is of the formula III shown below:

III

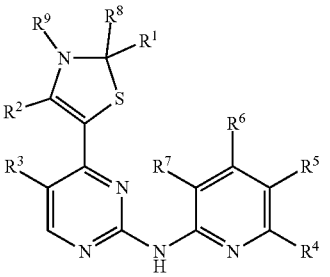

wherein $R^2$, $R^3$, $R^4$, $R^5$, $R^6$ and $R^7$ are as defined above for formula I, $R^8$ is together with $R^1$ is =O or =S, and $R^9$ is H, alkyl (eg a $C_{1-6}$ alkyl or, preferably, a $C_{1-3}$ alkyl such as methyl, ethyl and cyclopentyl), aryl or heterocyclic group.

In some embodiments, $R^1$ is H, alkyl (eg a $C_{1-6}$ alkyl or, preferably, a $C_{1-3}$ alkyl such as methyl, ethyl and $C(CH_3)_2$), aryl, NH-alkyl (eg a NH—$C_{1-6}$ alkyl such as $NH(C_5H_9)$ (ie NH-cyclopentyl) or, preferably, a NH—$C_{1-3}$ alkyl such as NH—$CH_3$), $N(alkyl)_2$ (eg a $N(C_{1-6}\ alkyl)_2$ such as $N(C_5H_9)_2$ or a $N(C_{1-3}\ alkyl)_2$ such as $N(CH_3)_2$), NH-aryl, N-(alkyl)(aryl), SH-alkyl (eg a SH—$C_{1-6}$ alkyl or, preferably, a SH—$C_{1-3}$ alkyl such as $SHCH_3$ and $SHC(CH_3)$) or $R^{12}$. Where $R^1$ is $R^{12}$, preferably $R^{12}$ is a mono-, di- or poly-hydroxylated alicyclic group, or an N-, O- and/or S-containing heterocyclic group substituted with one or more hydroxyl or amino group.

In some embodiments, $R^2$ is H, alkyl (eg a $C_{1-6}$ alkyl or, preferably, a $C_{1-3}$ alkyl such as methyl and ethyl), aryl, CN, $CF_3$, $NH_2$, NH-alkyl (eg a NH—$C_{1-6}$ alkyl such as $NH(C_5H_9)$ or, preferably, a NH—$C_{1-3}$ alkyl such as NH—$CH_3$), N-$(alkyl)_2$ (eg a $N(C_{1-6}\ alkyl)_2$ such as $N(C_5H_9)_2$ or a $N(C_{1-3}\ alkyl)_2$ such as $N(CH_3)_2$), N-(alkyl)(aryl) or $R^{12}$. Where $R^2$ is $R^{12}$, preferably $R^{12}$ is a mono-, di- or poly-hydroxylated alicyclic group, or an N-, O- and/or S-containing heterocyclic group substituted with one or more hydroxyl or amino group.

In some embodiments, $R^3$ is H, alkyl (eg a $C_{1-6}$ alkyl or, preferably, a $C_{1-3}$ alkyl such as methyl or ethyl), CN, or halogen (preferably F).

In some embodiments, $R^4$ is H, O-alkyl (preferably, a $C_{1-6}$ alkoxy or, more preferably, a $C_{1-3}$ alkoxy such as methoxy or ethoxy) or halogen (preferably F).

In some embodiments, at least one of $R^5$ and $R^6$, but preferably $R^5$, is $R^{12}$ wherein $R^{12}$ is preferably an N-, O- and/or S-containing heterocyclic group substituted with one or more hydroxyl, amino or alkoxy (eg —$COCH_3$) group. Preferably, the heteroatom(s) is/are N.

In some embodiments, where at least one of $R^5$ and $R^6$ is $R^{12}$, $R^{12}$ is preferably selected from the following:

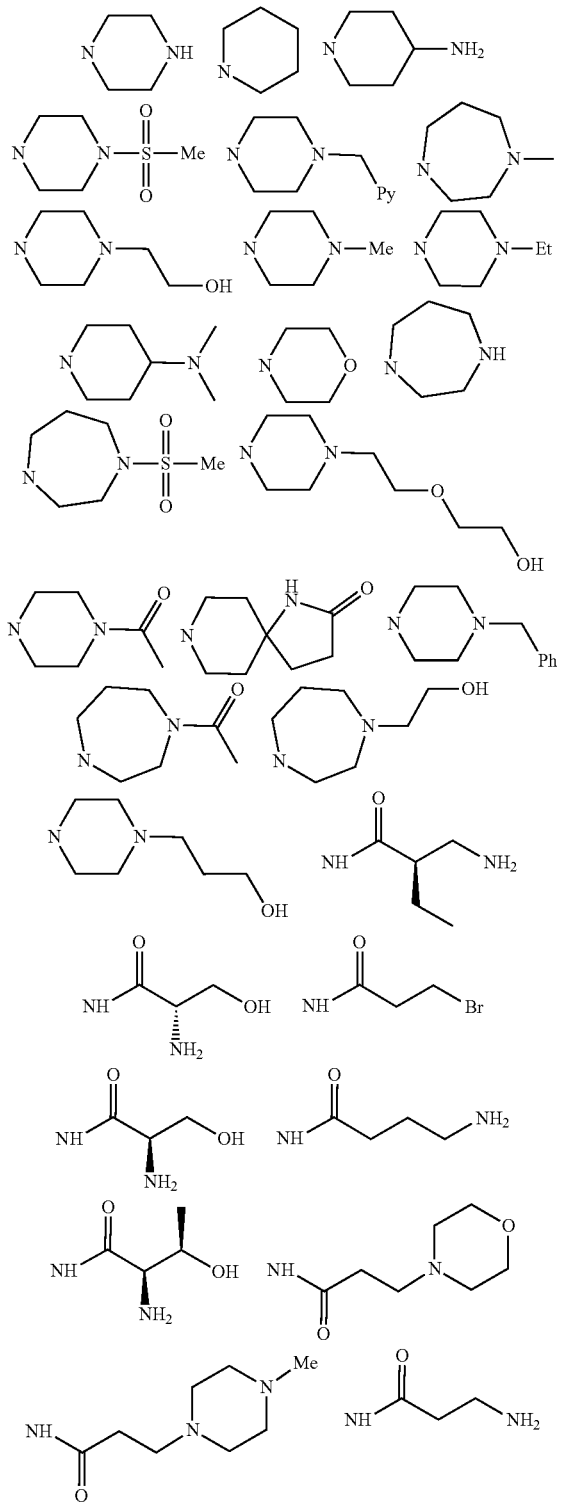

-continued

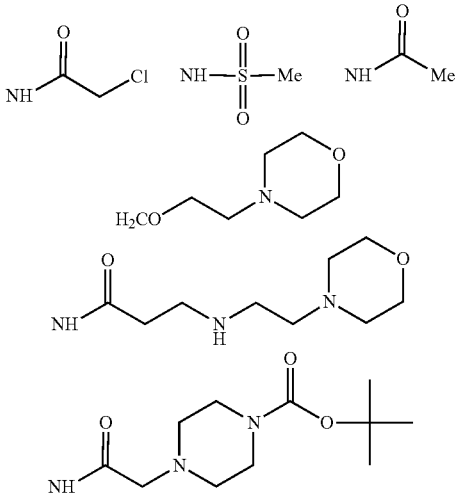

Optionally, the $R^{12}$ substituents shown in the preceding paragraph [0055] may further comprise an alkyl bridge (eg a —$CH_2$— or —$CH_2CH$— bridge) to the carbon atom at position 4/5 of the pyridine/phenyl ring.

Where $R_5$ is $R^{12}$, $R^6$ is preferably H. Vice versa, where $R^6$ is $R^{12}$, $R^5$ is preferably H.

In some embodiments, $R^7$ is H.

In some embodiments, $R^5$ is $R^{12}$ and $R^2$, $R^3$, $R^4$, $R^6$ and $R^7$ are each independently selected from H, alkyl (eg a $C_{1-6}$ alkyl or, preferably, a $C_{1-3}$ alkyl), aryl, alicyclic, heterocyclic, halogen, $NO_2$, CN, $CF_3$, OH, O-alkyl (eg a $C_{1-6}$ alkoxy or, more preferably, a $C_{1-3}$ alkoxy such as methoxy or ethoxy), $NH_2$, NH-alkyl (eg a NH—$C_{1-6}$ alkyl such as NH($C_5H_9$) or, preferably, a NH—$C_{1-3}$ alkyl such as NH—$CH_3$) and N-(alkyl)$_2$ (eg a N($C_{1-6}$ alkyl)$_2$ such as N($C_5H_9$)$_2$ or a N($C_{1-3}$ alkyl)$_2$ such as N($CH_3$)$_2$).

In some embodiments, the compound is of formula II and $R^5$ is $R^{12}$, $R^1$ is alkyl (eg a $C_{1-6}$ alkyl such as cyclopentyl or a $C_{1-3}$ alkyl such as methyl and ethyl), NH(alkyl) (eg a NH—$C_{1-6}$ alkyl or, preferably, a NH—$C_{1-3}$ alkyl), N(alkyl)$_2$(eg a N($C_{1-6}$ alkyl) such as N($C_5H_9$)$_2$ or a N($C_{1-3}$ alkyl)$_2$ such as N($CH_3$)$_2$), NH(aryl), O-alkyl (eg a $C_{1-6}$ alkoxy or, more preferably, a $C_{1-3}$ alkoxy), S-alkyl (eg a S—$C_{1-6}$ alkyl or a S—$C_{1-3}$ alkyl) and $NH_2$, and $R^2$, $R^3$, $R^4$, $R^6$ and $R^7$ are each independently selected from H, alkyl (eg a $C_{1-6}$ alkyl such as cyclopentyl or a $C_{1-3}$ alkyl), halogen, CN, $CF_3$, O-alkyl (eg a $C_{1-6}$ alkoxy or, more preferably, a $C_{1-3}$ alkoxy), $NH_2$ and NH-alkyl (eg a NH—$C_{1-6}$ alkyl or, preferably, a NH—$C_{1-3}$ alkyl).

In some embodiments, the compound is of formula II and $R^5$ is $R^{12}$, $R^1$ is alkyl (eg a $C_{1-6}$ alkyl such as cyclopentyl or a $C_{1-3}$ alkyl such as methyl and ethyl), NH(alkyl) (eg a NH—$C_{1-6}$ alkyl or, preferably, a NH—$C_{1-3}$ alkyl), N(alkyl)$_2$ (eg a N($C_{1-6}$ alkyl) or, more preferably, a N($C_{1-3}$ alkyl)$_2$) NH(aryl), O-alkyl (eg a $C_{1-6}$ alkoxy or, more preferably, a $C_{1-3}$ alkoxy), S-alkyl (eg a S—$C_{1-6}$ alkyl or a S—$C_{1-3}$ alkyl) and $NH_2$, $R^3$ is selected from H, alkyl, halogen and CN, and $R^2$, $R^4$, $R^6$ and $R^7$ are each independently selected from H, alkyl (eg a $C_{1-6}$ alkyl such as cyclopentyl or a $C_{1-3}$ alkyl), halogen, CN, $CF_3$, O-alkyl (eg a $C_{1-6}$ alkoxy or, more preferably, a $C_{1-3}$ alkoxy), $NH_2$ and NH-alkyl (eg a NH—$C_{1-6}$ alkyl or, preferably, a NH—$C_{1-3}$ alkyl).

In some embodiments, the compound is of formula III and $R^5$ is $R^{12}$, and $R^2$, $R^3$, $R^4$, $R^6$ and $R^7$ are each independently selected from H, alkyl (eg a $C_{1-6}$ alkyl such as cyclopentyl or a $C_{1-3}$ alkyl), halogen, CN, $CF_3$, O-alkyl (eg a $C_{1-6}$ alkoxy or, more preferably, a $C_{1-3}$ alkoxy), $NH_2$ and NH-alkyl (eg a NH—$C_{1-6}$ alkyl or, preferably, a NH—$C_{1-3}$ alkyl).

In some embodiments, the compound is of formula III and $R^5$ is $R^{12}$, $R^3$ is selected from H, alkyl (eg a $C_{1-6}$ alkyl such as cyclopentyl or a $C_{1-3}$ alkyl), halogen and CN, and $R^2$, $R^4$, $R^6$ and $R^7$ are each independently selected from H, alkyl (eg a $C_{1-6}$ alkyl such as cyclopentyl or a $C_{1-3}$ alkyl), halogen, CN, $CF_3$, O-alkyl (eg a $C_{1-6}$ alkoxy or, more preferably, a $C_{1-3}$ alkoxy), $NH_2$, and NH-alkyl (eg a NH—$C_{1-6}$ alkyl or, preferably, a NH—$C_{1-3}$ alkyl).

In some preferred embodiments, the compounds of the present invention exhibit anti-proliferative activity in human cell lines, as measured by a standard cytotoxicity assay. Preferably, the compound exhibits an $IC_{50}$ value of less than 5 μM, even more preferably less than 1 μM as measured by the cell viability (MTT proliferation) assay described in Example 2 hereinafter. More preferably still, the compound exhibits an $IC_{50}$ value of less than 0.5 μM.

In some preferred embodiments, the compounds of the present invention inhibit one or more protein kinases, as measured by any standard assay well known to those skilled in the art. Preferably, the compound exhibits an $IC_{50}$ value of less than 1 μM or less than 0.5 μM as measured by the kinase assay described in Example 2 hereinafter, more preferably still less than 0.1 μM.

Particular examples of compounds according to the first aspect are shown in Table 1 below.

TABLE 1

Chemical structure of selected compounds of the present invention

| No. | Structure | Name | Mass |
|---|---|---|---|
| 1. | 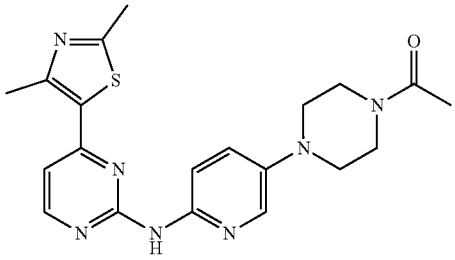 | 1-(4-(6-((4-(2,4-dimethylthiazol-5-yl)pyrimidin-2-yl)amino)pyridin-3-yl)piperazin-1-yl)ethan-1-one | 409.5 |

TABLE 1-continued

Chemical structure of selected compounds of the present invention

| No. | Structure | Name | Mass |
|---|---|---|---|
| 2. | 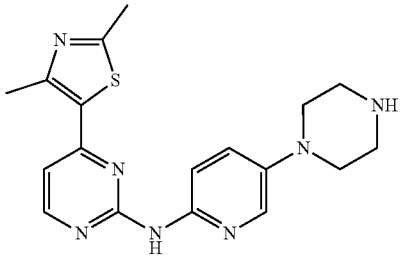 | 4-(2,4-dimethylthiazol-5-yl)-N-(5-(piperazin-1-yl)pyridin-2-yl)pyrimidin-2-amine | 367.5 |
| 3. | 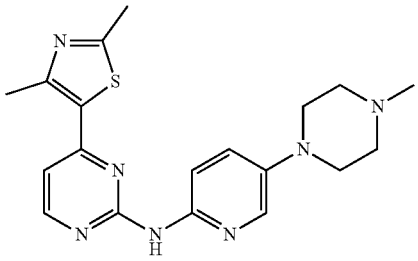 | 4-(2,4-dimethylthiazol-5-yl)-N-(5-(4-methylpiperazin-1-yl)pyridin-2-yl)pyrimidin-2-amine | 381.5 |
| 4. | 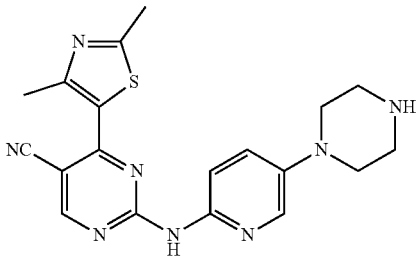 | 4-(2,4-dimethylthiazol-5-yl)-2-((5-(piperazin-1-yl)pyridin-2-yl)amino)pyrimidine-5-carbonitrile | 392.5 |
| 5. | 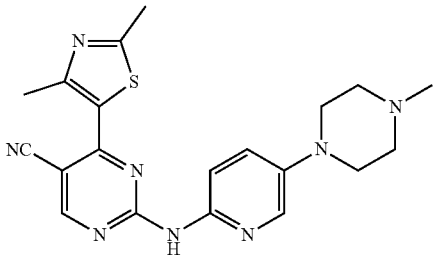 | 4-(2,4-dimethylthiazol-5-yl)-2-((5-(4-methylpiperazin-1-yl)pyridin-2-yl)amino)pyrimidine-5-carbonitrile | 406.5 |
| 6. | 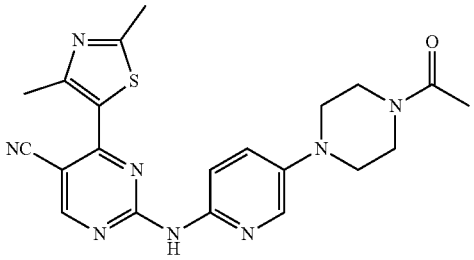 | 2-((5-(4-acetylpiperazin-1-yl)pyridin-2-yl)amino)-4-(2,4-dimethylthiazol-5-yl)pyrimidine-5-carbonitrile | 434.5 |

TABLE 1-continued

| Chemical structure of selected compounds of the present invention | | | |
|---|---|---|---|
| No. | Structure | Name | Mass |
| 7. | 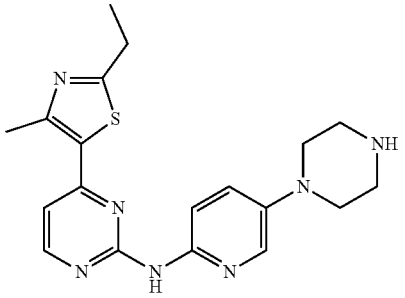 | 4-(2-ethyl-4-methylthiazol-5-yl)-N-(5-(piperazin-1-yl)pyridin-2-yl)pyrimidin-2-amine | 381.5 |
| 8. | 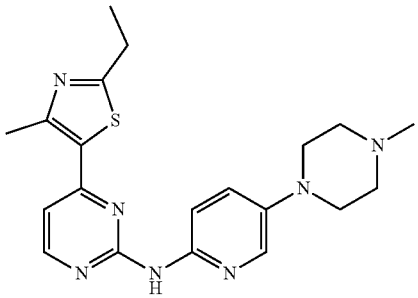 | 4-(2-ethyl-4-methylthiazol-5-yl)-N-(5-(4-methylpiperazin-1-yl)pyridin-2-yl)pyrimidin-2-amine | 395.5 |
| 9. | 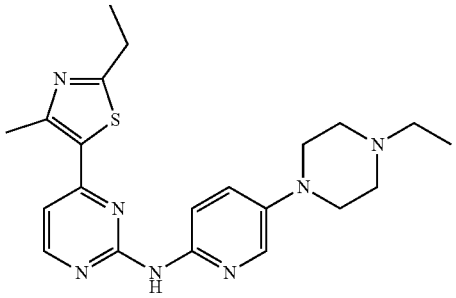 | 4-(2-ethyl-4-methylthiazol-5-yl)-N-(5-(4-ethylpiperazin-1-yl)pyridin-2-yl)pyrimidin-2-amine | 409.6 |
| 10. | 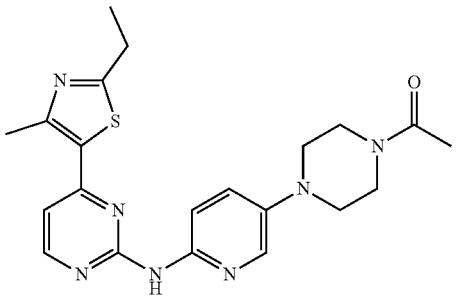 | 1-(4-(6-((4-(2-ethyl-4-methylthiazol-5-yl)pyrimidin-2-yl)amino)pyridin-3-yl)piperazin-1-yl)ethan-1-one | 423.5 |
| 11. | 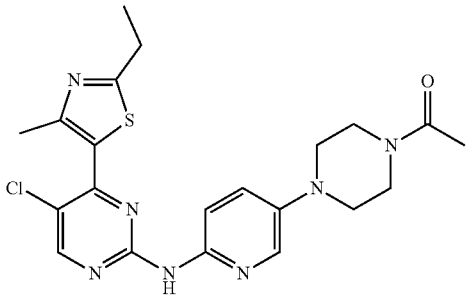 | 1-(4-(6-((5-chloro-4-(2-ethyl-4-methylthiazol-5-yl)pyrimidin-2-yl)amino)pyridin-3-yl)piperazin-1-yl)ethan-1-one | 458.0 |

TABLE 1-continued

| Chemical structure of selected compounds of the present invention | | | |
|---|---|---|---|
| No. | Structure | Name | Mass |
| 12. | 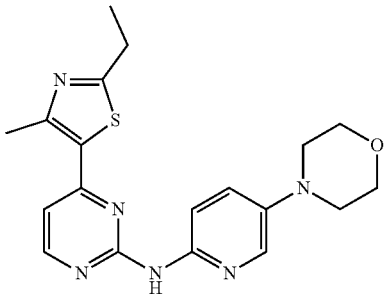 | 4-(2-Ethyl-4-methylthiazol-5-yl)-N-(5-morpholinopyridin-2-yl)pyrimidin-2-amine | 382.5 |
| 13. | 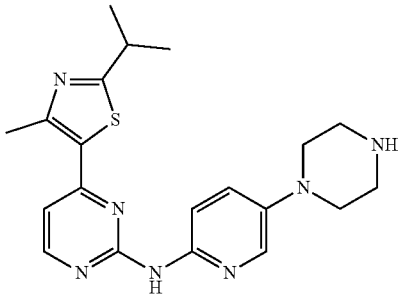 | 4-(2-isopropyl-4-methylthiazol-5-yl)-N-(5-(piperazin-1-yl)pyridin-2-yl)pyrimidin-2-amine | 395.5 |
| 14. | 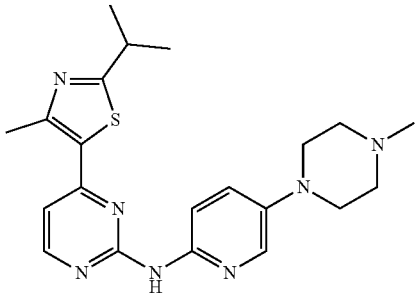 | 4-(2-isopropyl-4-methylthiazol-5-yl)-N-(5-(4-methylpiperazin-1-yl)pyridin-2-yl)pyrimidin-2-amine | 409.6 |
| 15. | 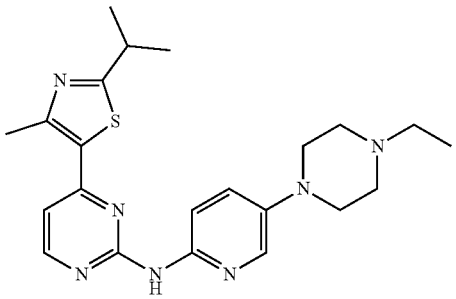 | N-(5-(4-ethylpiperazin-1-yl)pyridin-2-yl)-4-(2-isopropyl-4-methylthiazol-5-yl)pyrimidin-2-amine | 423.6 |
| 16. | 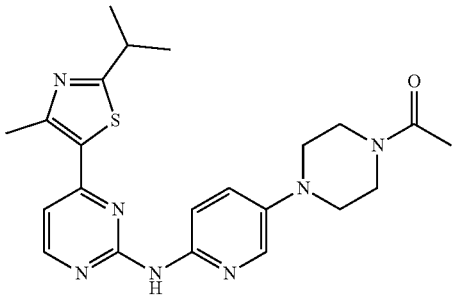 | 1-(4-(6-((4-(2-isopropyl-4-methylthiazol-5-yl)pyrimidin-2-yl)amino)pyridin-3-yl)piperazin-1-yl)ethan-1-one | 437.6 |

TABLE 1-continued

| Chemical structure of selected compounds of the present invention | | | |
|---|---|---|---|
| No. | Structure | Name | Mass |
| 17. | 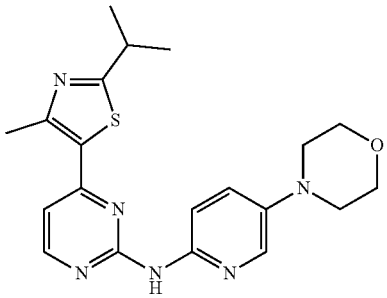 | 4-(2-isopropyl-4-methylthiazol-5-yl)-N-(5-morpholinopyridin-2-yl)pyrimidin-2-amine | 396.5 |
| 18. | 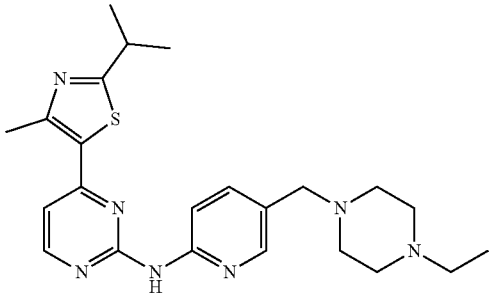 | N-(5-((4-ethylpiperazin-1-yl)methyl)pyridin-2-yl)-4-(2-isopropyl-4-methylthiazol-5-yl)pyrimidin-2-amine | 437.6 |
| 19. | 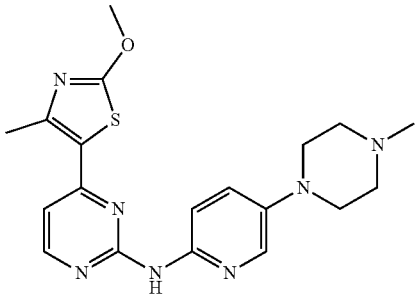 | 4-(2-methoxy-4-methylthiazol-5-yl)-N-(5-(4-methylpiperazin-1-yl)pyridin-2-yl)pyrimidin-2-amine | 397.5 |
| 20. | 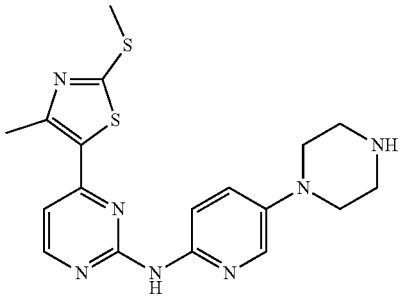 | 4-(4-methyl-2-(methylthio)thiazol-5-yl)-N-(5-(4-piperazin-1-yl)pyridin-2-yl)pyrimidin-2-amine | 399.5 |
| 21. | 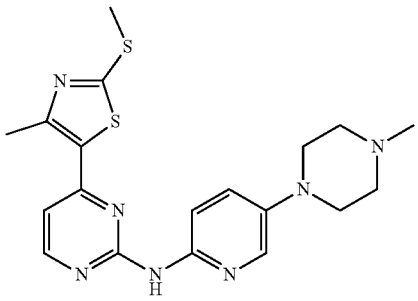 | 4-(4-methyl-2-(methylthio)thiazol-5-yl)-N-(5-(4-methylpiperazin-1-yl)pyridin-2-yl)pyrimidin-2-amine | 413.6 |

TABLE 1-continued

| Chemical structure of selected compounds of the present invention | | | |
|---|---|---|---|
| No. | Structure | Name | Mass |
| 22. | 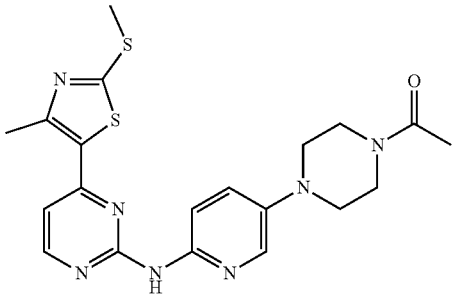 | 1-(4-(6-((4-(4-methyl-2-(methylthio)thiazol-5-yl)pyrimidin-2-yl)amino)pyridin-3-yl)piperazin-1-yl)ethan-1-one | 441.6 |
| 23. | 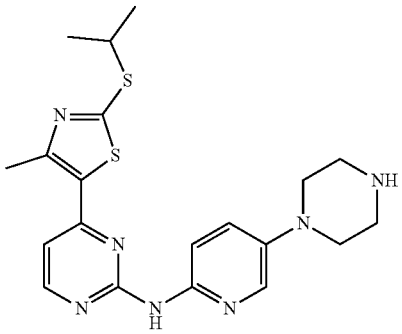 | 4-(2-(isopropylthio)-4-methylthiazol-5-yl)-N-(5-(piperazin-1-yl)pyridin-2-yl)pyrimidin-2-amine | 427.6 |
| 24. | 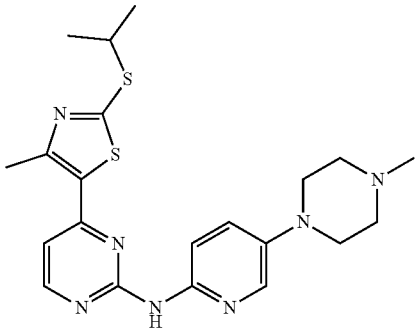 | 4-(2-(isopropylthio)-4-methylthiazol-5-yl)-N-(5-(4-methylpiperazin-1-yl)pyridin-2-yl)pyrimidin-2-amine | 441.6 |
| 25. | 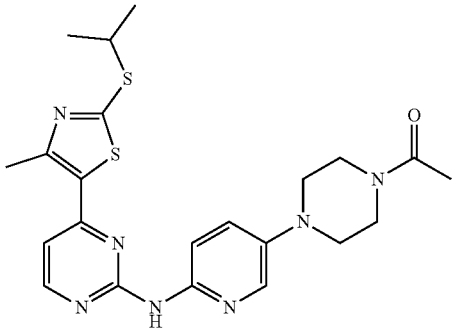 | 1-(4-(6-((4-(2-(isopropylthio)-4-methylthiazol-5-yl)pyrimidin-2-yl)amino)pyridin-3-yl)piperazin-1-yl)ethan-1-one | 469.6 |

TABLE 1-continued

| Chemical structure of selected compounds of the present invention | | | |
|---|---|---|---|
| No. | Structure | Name | Mass |
| 26. | 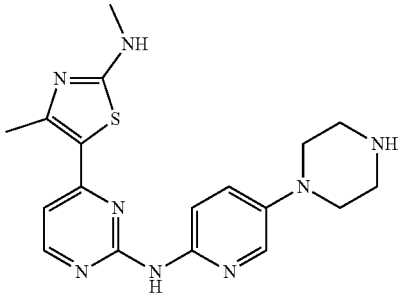 | N,4-dimethyl-5-(2-((5-(piperazin-1-yl)pyridin-2-yl)amino)pyrimidin-4-yl)thiazol-2-amine | 382.5 |
| 27. | 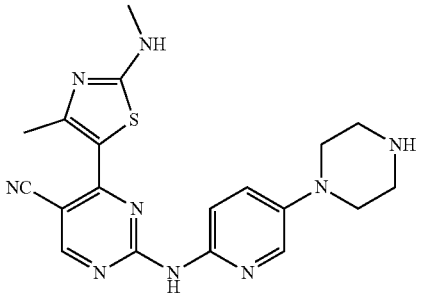 | 4-(4-methyl-2-(methylamino)thiazol-5-yl)-2-((5-(piperazin-1-yl)pyridin-2-yl)amino)pyrimidine-5-carbonitrile | 407.5 |
| 28. | 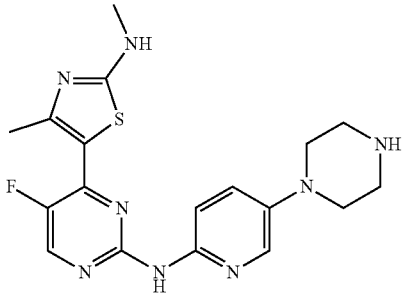 | 5-(5-fluoro-2-((5-(piperazin-1-yl)pyridin-2-yl)amino)pyrimidin-4-yl)-N,4-dimethylthiazol-2-amine | 400.5 |
| 29. | 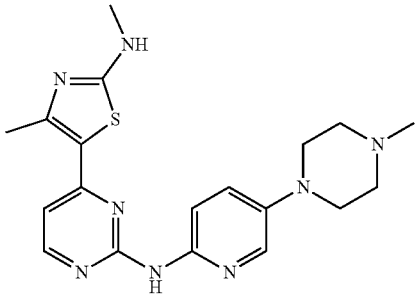 | N,4-dimethyl-5-(2-((5-(4-methylpiperazin-1-yl)pyridin-2-yl)amino)pyrimidin-4-yl)thiazol-2-amine | 396.5 |
| 30. | 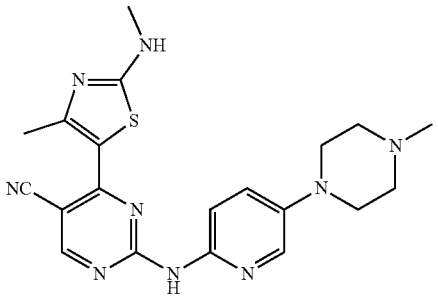 | 4-(4-methyl-2-(methylamino)thiazol-5-yl)-2-((5-(4-methylpiperazin-1-yl)pyridin-2-yl)amino)pyrimidine-5-carbonitrile | 421.5 |

TABLE 1-continued

| Chemical structure of selected compounds of the present invention | | | |
|---|---|---|---|
| No. | Structure | Name | Mass |
| 31. | 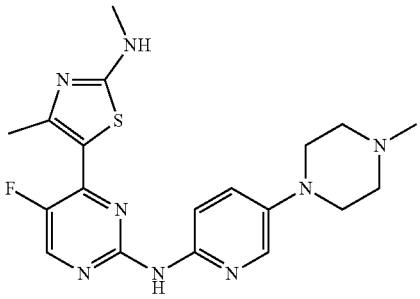 | 5-(5-fluoro-2-((5-(4-methylpiperazin-1-yl)pyridin-2-yl)amino)pyrimidin-4-yl)-N,4-dimethylthiazol-2-amine | 414.5 |
| 32. | 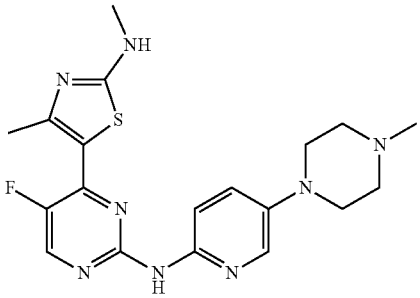 | 5-(5-fluoro-2-((5-(4-methylpiperazin-1-yl)pyridin-2-yl)amino)pyrimidin-4-yl)-N,4-dimethylthiazol-2-amine | 428.5 |
| 33. | 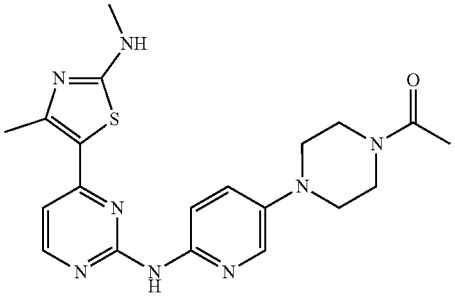 | 1-(4-(6-((4-(4-methyl-2-(methylamino)thiazol-5-yl)pyrimidin-2-yl)amino)pyridin-3-yl)piperazin-1-yl)ethan-1-one | 424.5 |
| 34. | 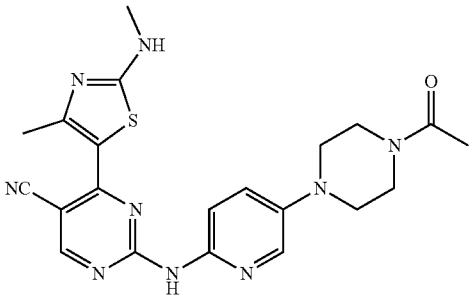 | 2-((5-(4-acetylpiperazin-1-yl)pyridin-2-yl)amino)-4-(4-methyl-2-(methylamino)thiazol-5-yl)pyrimidine-5-carbonitrile | 449.5 |
| 35. | 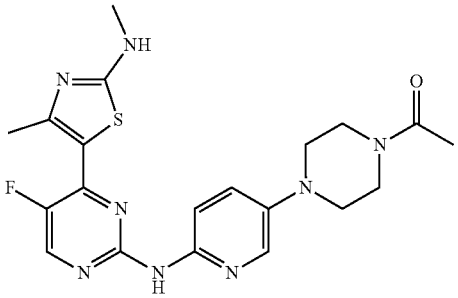 | 1-(4-(6-((5-fluoro-4-(4-methyl-2-(methylamino)thiazol-5-yl)pyrimidin-2-yl)amino)pyridin-3-yl)piperazin-1-yl)ethan-1-one | 442.5 |

TABLE 1-continued

| Chemical structure of selected compounds of the present invention | | | |
|---|---|---|---|
| No. | Structure | Name | Mass |
| 36. | 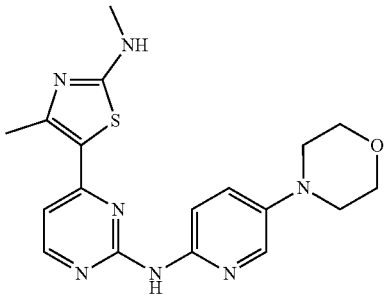 | N,4-dimethyl-5-(2-((5-morpholinopyridin-2-yl)amino)pyrimidin-4-yl)thiazol-2-amine | 383.5 |
| 37. | 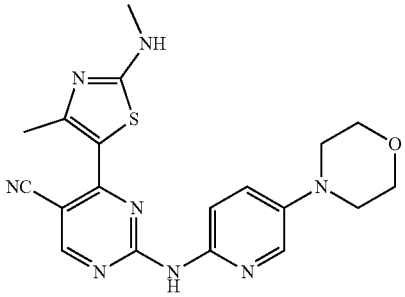 | 4-(4-methyl-2-(methylamino)thiazol-5-yl)-2-((5-morpholinopyridin-2-yl)amino)pyrimidine-5-carbonitrile | 408.5 |
| 38. | 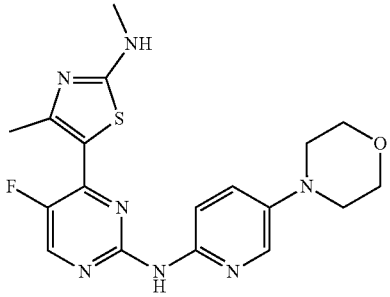 | 5-(5-fluoro-2-((5-morpholinopyridin-2-yl)amino)pyrimidin-4-yl)-N,4-dimethylthiazol-2-amine | 401.5 |
| 39. | 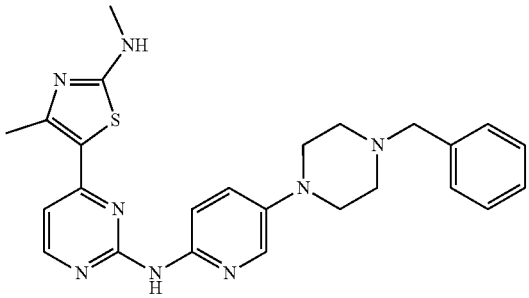 | 5-(2-((5-(4-benzylpiperazin-1-yl)pyridin-2-yl)amino)pyrimidin-4-yl)-N,4-dimethylthiazol-2-amine | 472.6 |
| 40. | 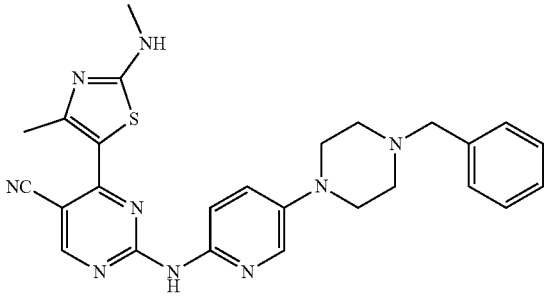 | 2-((5-(4-benzylpiperazin-1-yl)pyridin-2-yl)amino)-4-(4-methyl-2-(methylamino)thiazol-5-yl)pyrimidine-5-carbonitrile | 497.6 |

TABLE 1-continued

| Chemical structure of selected compounds of the present invention | | | |
|---|---|---|---|
| No. | Structure | Name | Mass |
| 41. | 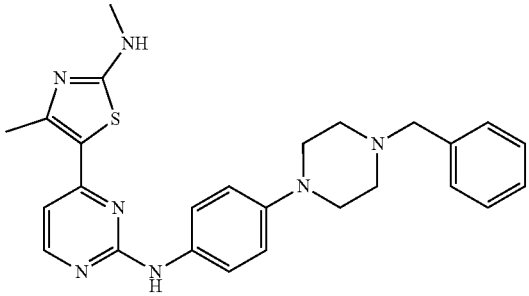 | 5-(2-((4-(4-benzylpiperazin-1-yl)phenyl)amino)pyrimidin-4-yl)-N,4-dimethylthiazol-2-amine | 471.6 |
| 42. | 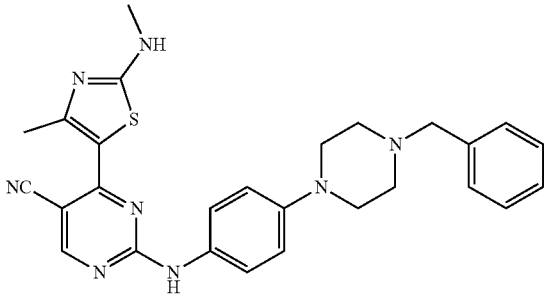 | 2-((4-(4-benzylpiperazin-1-yl)phenyl)amino)-4-(4-methyl-2-(methylamino)thiazol-5-yl)pyrimidine-5-carbonitrile | 496.6 |
| 43. | 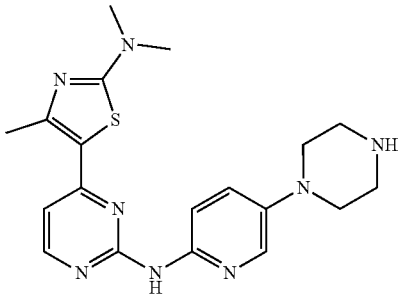 | N,N,4-trimethyl-5-(2-((5-(piperazin-1-yl)pyridin-2-yl)amino)pyrimidin-4-yl)thiazol-2-amine | 396.5 |
| 44. | 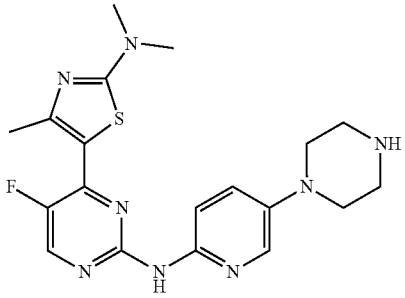 | 5-(5-fluoro-2-((5-(piperazin-1-yl)pyridin-2-yl)amino)pyrimidin-4-yl)-N,N,4-trimethylthiazol-2-amine | 414.5 |
| 45. | 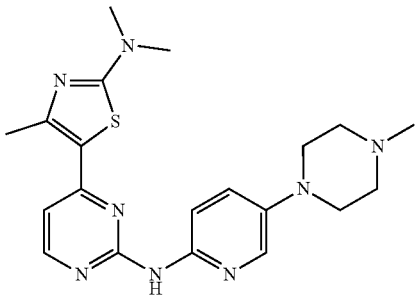 | N,N,4-trimethyl-5-(2-((5-(4-methylpiperazin-1-yl)pyridin-2-yl)amino)pyrimidin-4-yl)thiazol-2-amine | 410.5 |

TABLE 1-continued

| Chemical structure of selected compounds of the present invention | | | |
|---|---|---|---|
| No. | Structure | Name | Mass |
| 46. | 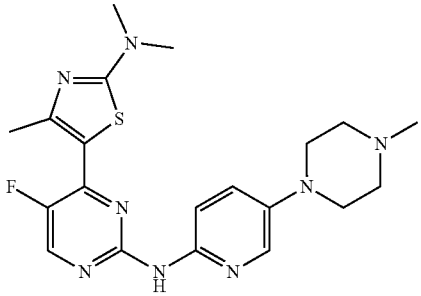 | 5-(5-fluoro-2-((5-(4-methylpiperazin-1-yl)pyridin-2-yl)amino)pyrimidin-4-yl)-N,N,4-trimethylthiazol-2-amine | 428.5 |
| 47. | 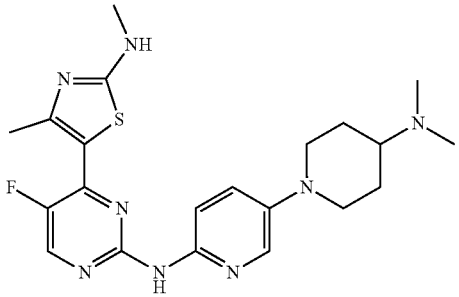 | 5-(2-((5-(4-(dimethylamino)piperidin-1-yl)pyridin-2-yl)amino)-5-fluoropyrimidin-4-yl)-N,4-dimethylthiazol-2-amine | 442.6 |
| 48. | 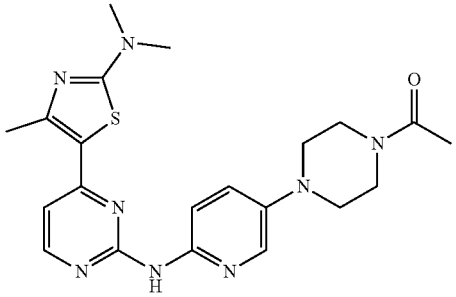 | 1-(4-(6-((4-(2-(dimethylamino)-4-methylthiazol-5-yl)pyrimidin-2-yl)amino)pyridin-3-yl)piperazin-1-yl)ethan-1-one | 438.6 |
| 49. | 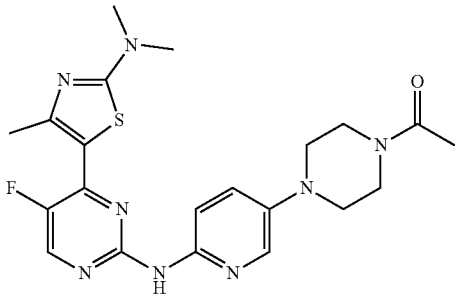 | 1-(4-(6-((4-(2-(dimethylamino)-4-methylthiazol-5-yl)-5-fluoropyrimidin-2-yl)amino)pyridin-3-yl)piperazin-1-yl)ethan-1-one | 456.5 |
| 50. | 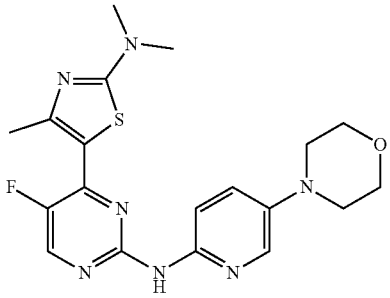 | 5-(5-fluoro-2-((5-morpholinopyridin-2-yl)amino)pyrimidin-4-yl)-N,N,4-trimethylthiazol-2-amine | 415.5 |

TABLE 1-continued

Chemical structure of selected compounds of the present invention

| No. | Structure | Name | Mass |
|---|---|---|---|
| 51. | 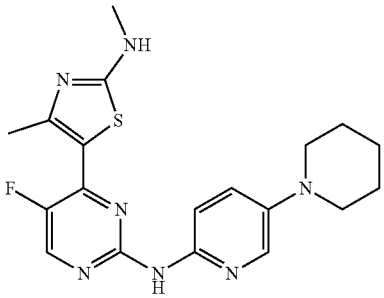 | 5-(5-fluoro-2-((5-(piperidin-1-yl)pyridin-2-yl)amino)pyrimidin-4-yl)-N,4-dimethylthiazol-2-amine | 399.5 |
| 52. | 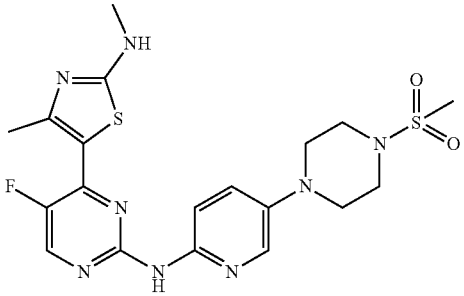 | 5-(5-fluoro-2-((5-(4-(methylsulfonyl)piperazin-1-yl)pyridin-2-yl)amino)pyrimidin-4-yl)-N,4-dimethylthiazol-2-amine | 478.6 |
| 53. | 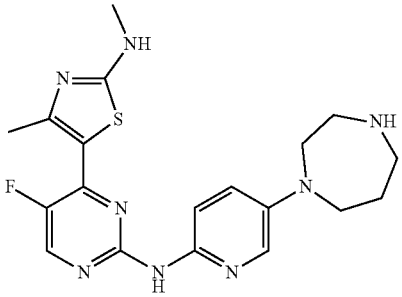 | 5-(2-((5-(1,4-diazepan-1-yl)pyridin-2-yl)amino)-5-fluoropyrimidin-4-yl)-N,4-dimethylthiazol-2-amine | 414.5 |
| 54. | 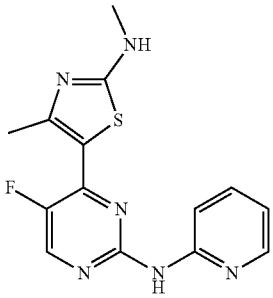 | 5-(5-fluoro-2-(pyridin-2-ylamino)pyrimidin-4-yl)-N,4-dimethylthiazol-2-amine | 316.4 |
| 55. | 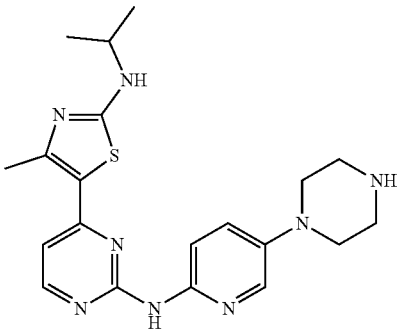 | N-isopropyl-4-methyl-5-(2-((5-(piperazin-1-yl)pyridin-2-yl)amino)pyrimidin-4-yl)thiazol-2-amine | 410.5 |

TABLE 1-continued

| Chemical structure of selected compounds of the present invention | | | |
|---|---|---|---|
| No. | Structure | Name | Mass |
| 56. | 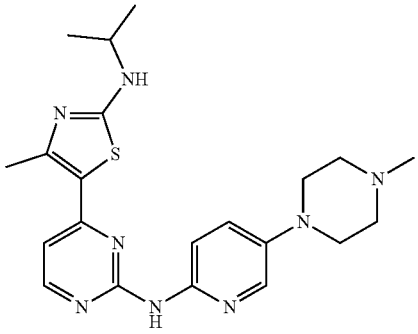 | N-isopropyl-4-methyl-5-(2-((5-(4-methylpiperazin-1-yl)pyridin-2-yl)amino)pyrimidin-4-yl)thiazol-2-amine | 424.6 |
| 57. | 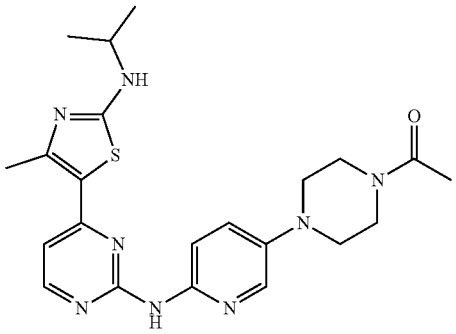 | 1-(4-(6-((4-(2-(isopropylamino)-4-methylthiazol-5-yl)pyrimidin-2-yl)amino)pyridin-3-yl)piperazin-1-yl)ethan-1-one | 452.6 |
| 58. | 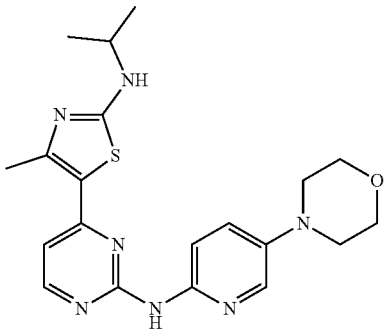 | N-isopropyl-4-methyl-5-(2-((5-morpholinopyridin-2-yl)amino)pyrimidin-4-yl)thiazol-2-amine | 411.5 |
| 59. | 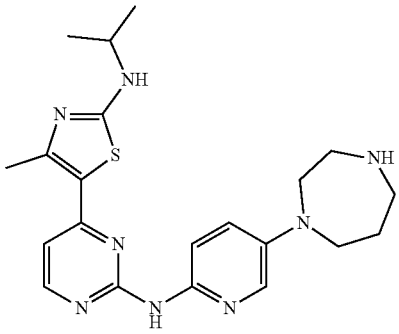 | 5-(2-((5-(1,4-diazepan-1-yl)pyridin-2-yl)amino)pyrimidin-4-yl)-N-isopropyl-4-methylthiazol-2-amine | 424.6 |

TABLE 1-continued

| Chemical structure of selected compounds of the present invention | | | |
|---|---|---|---|
| No. | Structure | Name | Mass |
| 60. | 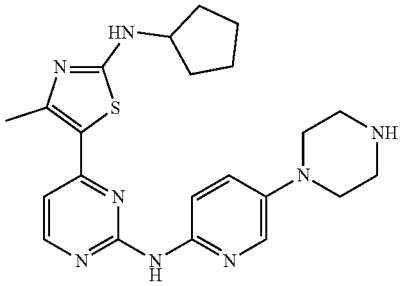 | N-cyclopentyl-4-methyl-5-(2-((5-(piperazin-1-yl)pyridin-2-yl)amino)pyrimidin-4-yl)thiazol-2-amine | 436.6 |
| 61. | 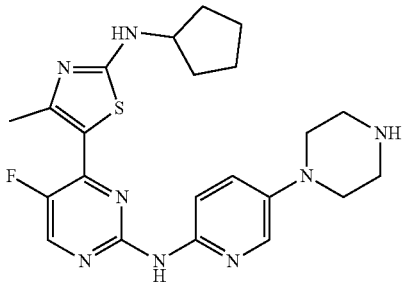 | N-cyclopentyl-5-(5-fluoro-2-((5-(piperazin-1-yl)pyridin-2-yl)amino)pyrimidin-4-yl)-4-methylthiazol-2-amine | 454.6 |
| 62. | 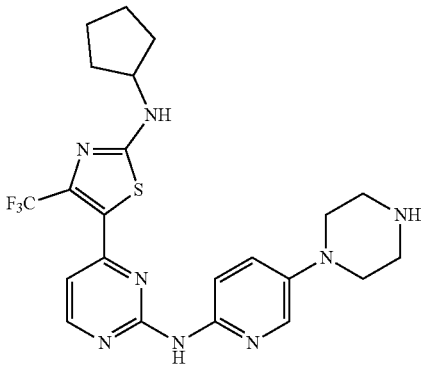 | N-cyclopentyl-5-(2-((5-(piperazin-1-yl)pyridin-2-yl)amino)pyrimidin-4-yl)-4-(trifluoromethyl)thiazol-2-amine | 490.6 |
| 63. | 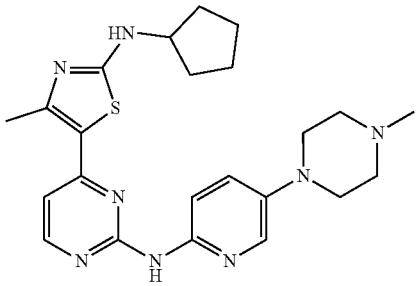 | N-cyclopentyl-4-methyl-5-(2-((5-(4-methylpiperazin-1-yl)pyridin-2-yl)amino)pyrimidin-4-yl)thiazol-2-amine | 450.6 |
| 64. | 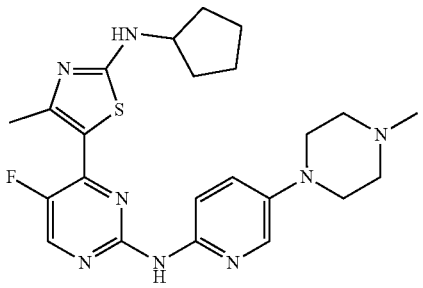 | N-cyclopentyl-5-(2-((5-(4-methylpiperazin-1-yl)pyridin-2-yl)amino)pyrimidin-4-yl)-4-(trifluoromethyl)thiazol-2-amine | 468.6 |

TABLE 1-continued

Chemical structure of selected compounds of the present invention

| No. | Structure | Name | Mass |
|---|---|---|---|
| 65. | 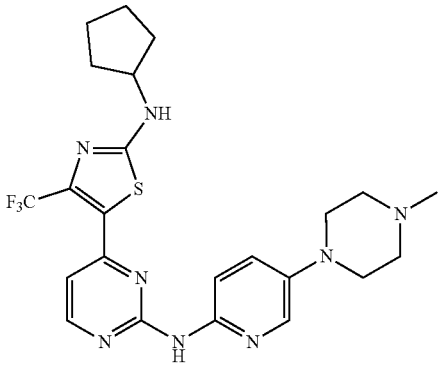 | N-cyclopentyl-5-(2-((5-(4-methylpiperazin-1-yl)pyridin-2-yl)amino)pyrimidin-4-yl)-4-(trifluoromethyl)thiazol-2-amine | 504.6 |
| 66. | 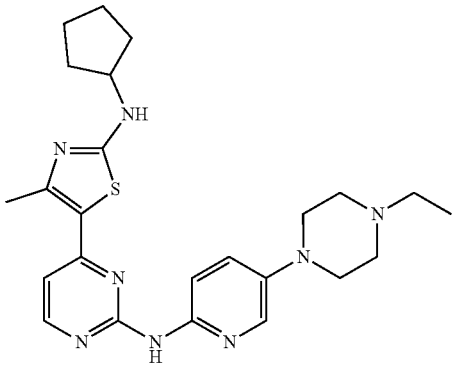 | N-cyclopentyl-5-(2-((5-(4-ethylpiperazin-1-yl)pyridin-2-yl)amino)pyrimidin-4-yl)-4-methylthiazol-2-amine | 464.6 |
| 67. | 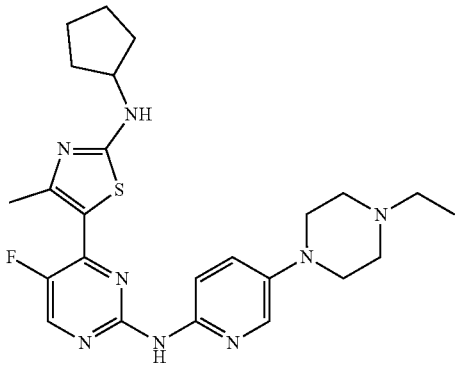 | N-cyclopentyl-5-(2-((5-(4-ethylpiperazin-1-yl)pyridin-2-yl)amino)-5-fluoropyrimidin-4-yl)-4-methylthiazol-2-amine | 482.6 |
| 68. | 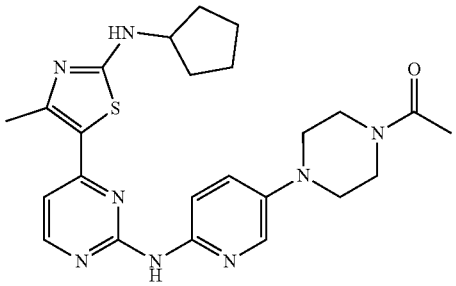 | 1-(4-(6-((4-(2-(cyclopentylamino)-4-(trifluoromethyl)thiazol-5-yl)pyrimidin-2-yl)amino)pyridin-3-yl)piperazin-1-yl)ethan-1-one | 478.6 |

TABLE 1-continued

| Chemical structure of selected compounds of the present invention | | | |
|---|---|---|---|
| No. | Structure | Name | Mass |
| 69. | 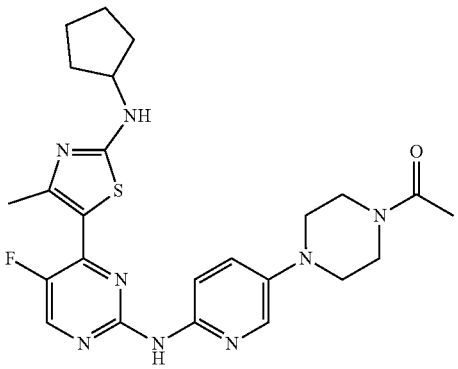 | 1-(4-(6-((4-(2-(cyclopentylamino)-4-(trifluoromethyl)thiazol-5-yl)pyrimidin-2-yl)amino)pyridin-3-yl)piperazin-1-yl)ethan-1-one | 496.6 |
| 70. | 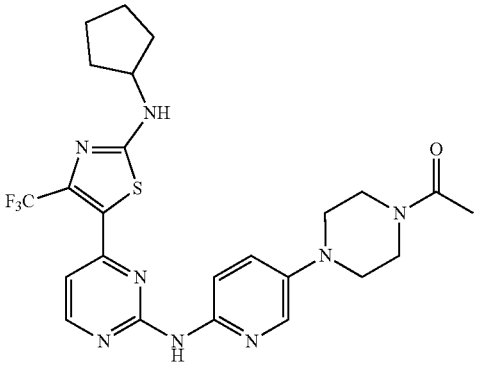 | 1-(4-(6-((4-(2-(cyclopentylamino)-4-(trifluoromethyl)thiazol-5-yl)pyrimidin-2-yl)amino)pyridin-3-yl)piperazin-1-yl)ethan-1-one | 532.6 |
| 71. | 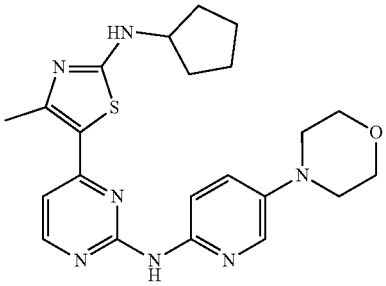 | N-cyclopentyl-4-methyl-5-(2-((5-morpholinopyridin-2-yl)amino)pyrimidin-4-yl)thiazol-2-amine | 437.6 |
| 72. | 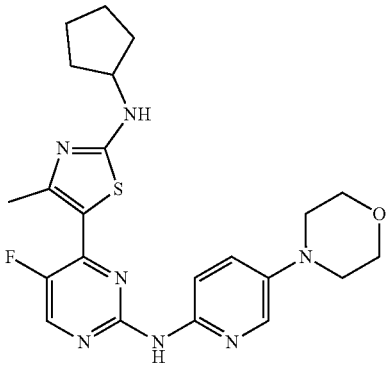 | N-cyclopentyl-5-(2-((5-morpholinopyridin-2-yl)amino)pyrimidin-4-yl)-4-(trifluoromethyl)thiazol-2-amine | 455.6 |

TABLE 1-continued

Chemical structure of selected compounds of the present invention

| No. | Structure | Name | Mass |
|---|---|---|---|
| 73. | 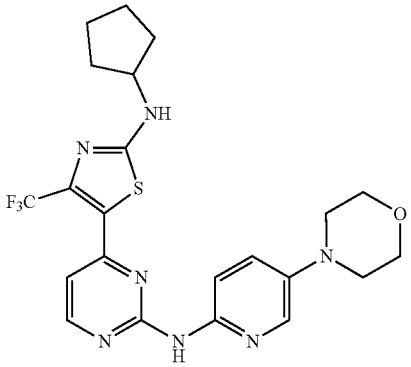 | N-cyclopentyl-5-(2-((5-morpholinopyridin-2-yl)amino)pyrimidin-4-yl)-4-(trifluoromethyl)thiazol-2-amine | 491.5 |
| 74. | 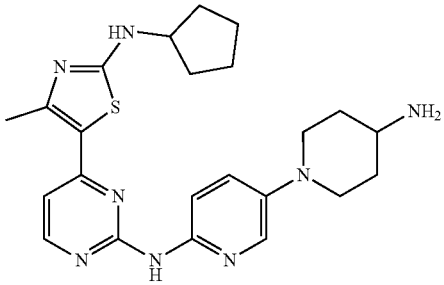 | 5-(2-((5-(4-aminopiperidin-1-yl)pyridin-2-yl)amino)pyrimidin-4-yl)-N-cyclopentyl-4-methylthiazol-2-amine | 450.6 |
| 75. | 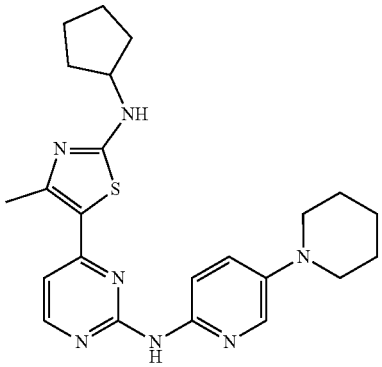 | N-cyclopentyl-4-methyl-5-(2-((5-(piperidin-1-yl)pyridin-2-yl)amino)pyrimidin-4-yl)thiazol-2-amine | 435.6 |
| 76. | 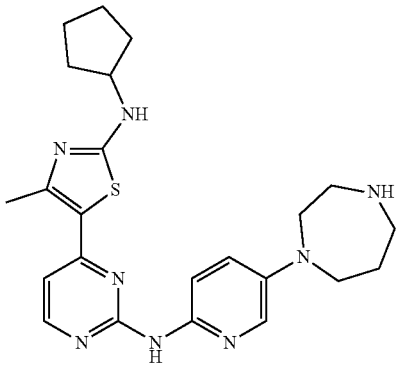 | 5-(2-((5-(1,4-diazepan-1-yl)pyridin-2-yl)amino)pyrimidin-4-yl)-N-cyclopentyl-4-methylthiazol-2-amine | 450.6 |

TABLE 1-continued

Chemical structure of selected compounds of the present invention

| No. | Structure | Name | Mass |
|---|---|---|---|
| 77. | 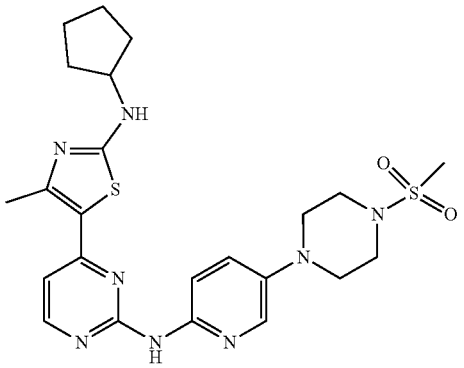 | N-cyclopentyl-4-methyl-5-(2-(pyridin-2-ylamino)pyrimidin-4-yl)thiazol-2-amine | 514.7 |
| 78. | 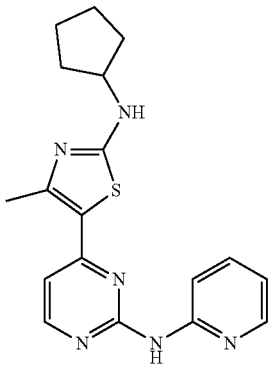 | N-cyclopentyl-4-methyl-5-(2-(pyridin-2-ylamino)pyrimidin-4-yl)thiazol-2-amine | 352.5 |
| 79. | 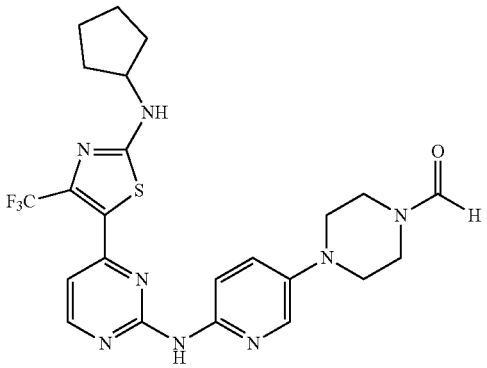 | 4-(6-((4-(2-(cyclopentylamino)-4-(trifluoromethyl)thiazol-5-yl)pyrimidin-2-yl)amino)pyridin-3-yl)piperazine-1-carbaldehyde | 518.6 |
| 80. | 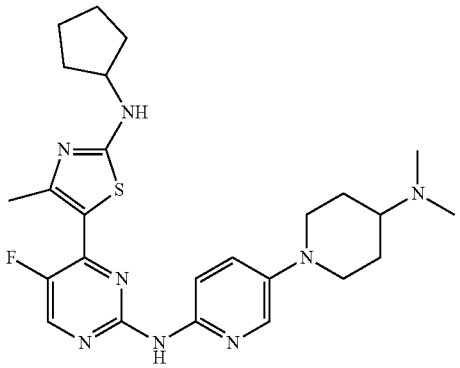 | N-cyclopentyl-5-(5-fluoro-2-((5-(4-(methylsulfonyl)piperazin-1-yl)pyridin-2-yl)amino)pyrimidin-4-yl)-4-methylthiazol-2-amine | 496.7 |

TABLE 1-continued

| Chemical structure of selected compounds of the present invention | | | |
|---|---|---|---|
| No. | Structure | Name | Mass |
| 81. | 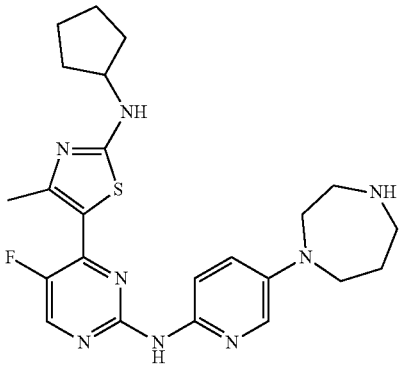 | N-cyclopentyl-5-(5-fluoro-2-((5-(4-(methylsulfonyl)piperazin-1-yl)pyridin-2-yl)amino)pyrimidin-4-yl)-4-methylthiazol-2-amine | 468.6 |
| 82. | 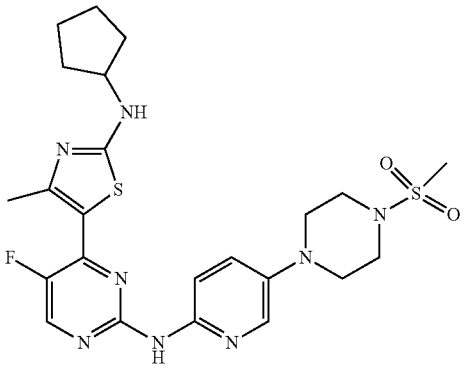 | N-cyclopentyl-5-(5-fluoro-2-((5-(4-(methylsulfonyl)piperazin-1-yl)pyridin-2-yl)amino)pyrimidin-4-yl)-4-methylthiazol-2-amine | 532.6 |
| 83. | 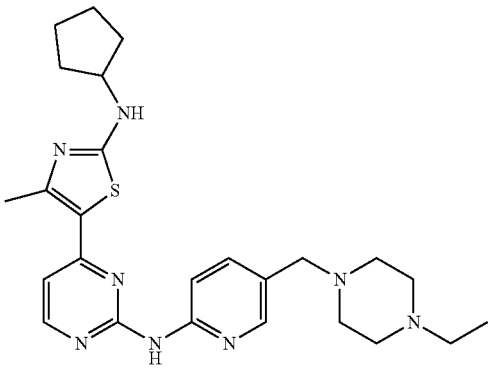 | N-cyclopentyl-5-(2-((5-((4-ethylpiperazin-1-yl)methyl)pyridin-2-yl)amino)-5-fluoropyrimidin-4-yl)-4-methylthiazol-2-amine | 478.7 |
| 84. | 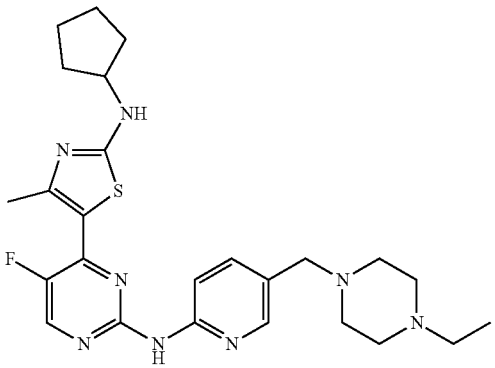 | N-cyclopentyl-5-(2-((5-((4-ethylpiperazin-1-yl)methyl)pyridin-2-yl)amino)-5-fluoropyrimidin-4-yl)-4-methylthiazol-2-amine | 496.6 |

TABLE 1-continued

| Chemical structure of selected compounds of the present invention | | | |
|---|---|---|---|
| No. | Structure | Name | Mass |
| 85. | 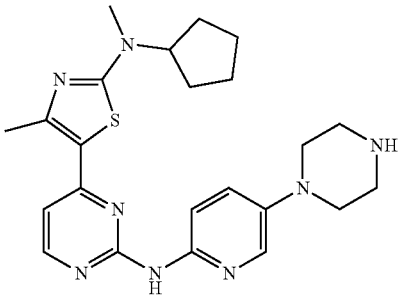 | N-cyclopentyl-N,4-dimethyl-5-(2-((5-(piperazin-1-yl)pyridin-2-yl)amino)pyrimidin-4-yl)thiazol-2-amine | 450.6 |
| 86. | 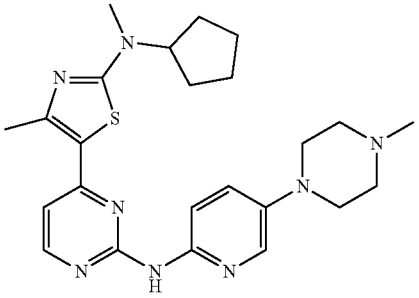 | N-cyclopentyl-N,4-dimethyl-5-(2-((5-(4-methylpiperazin-1-yl)pyridin-2-yl)amino)pyrimidin-4-yl)thiazol-2-amine | 464.6 |
| 87. | 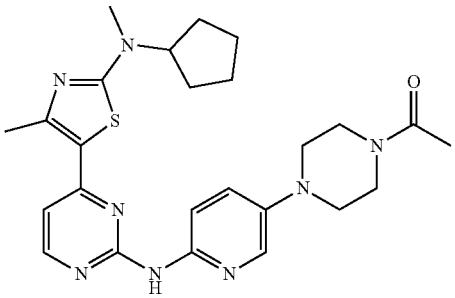 | 1-(4-(6-((4-(2-(cyclopentyl(methyl)amino)-4-methylthiazol-5-yl)pyrimidin-2-yl)amino)pyridin-3-yl)piperazin-1-yl)ethan-1-one | 492.6 |
| 88. | 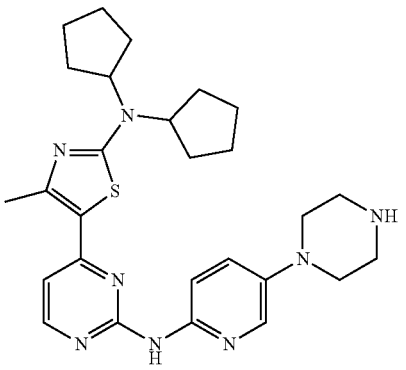 | N,N-dicyclopentyl-4-methyl-5-(2-((5-(piperazin-1-yl)pyridin-2-yl)amino)pyrimidin-4-yl)thiazol-2-amine | 504.7 |

TABLE 1-continued

| Chemical structure of selected compounds of the present invention | | | |
|---|---|---|---|
| No. | Structure | Name | Mass |
| 89. | 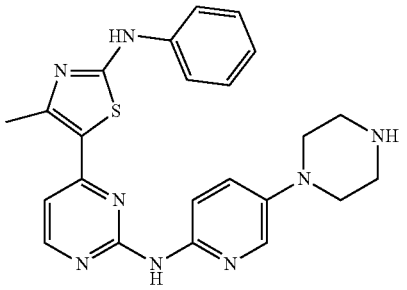 | 4-methyl-5-(2-((5-(4-methylpiperazin-1-yl)pyridin-2-yl)amino)pyrimidin-4-yl)-N-phenylthiazol-2-amine | 444.6 |
| 90. | 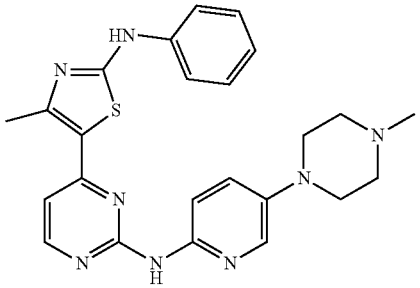 | 4-methyl-5-(2-((5-(4-methylpiperazin-1-yl)pyridin-2-yl)amino)pyrimidin-4-yl)-N-phenylthiazol-2-amine | 458.6 |
| 91. | 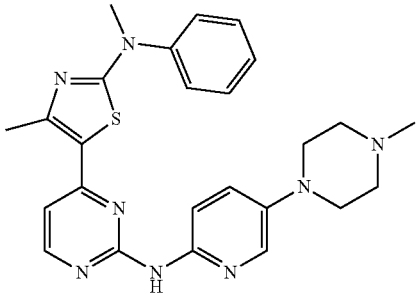 | N,4-dimethyl-5-(2-((5-(4-methylpiperazin-1-yl)pyridin-2-yl)amino)pyrimidin-4-yl)-N-phenylthiazol-2-amine | 472.6 |
| 92. | 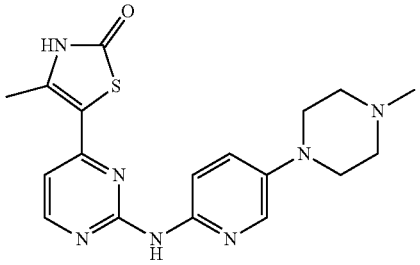 | 4-methyl-5-(2-((5-(4-methylpiperazin-1-yl)pyridin-2-yl)amino)pyrimidin-4-yl)thiazol-2(3H)-one | 383.5 |
| 93. | 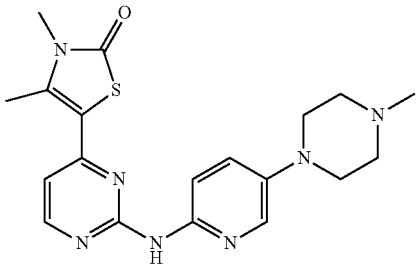 | 3,4-dimethyl-5-(2-((5-(4-methylpiperazin-1-yl)pyridin-2-yl)amino)pyrimidin-4-yl)thiazol-2(3H)-one | 397.5 |

TABLE 1-continued

Chemical structure of selected compounds of the present invention

| No. | Structure | Name | Mass |
|---|---|---|---|
| 94. | 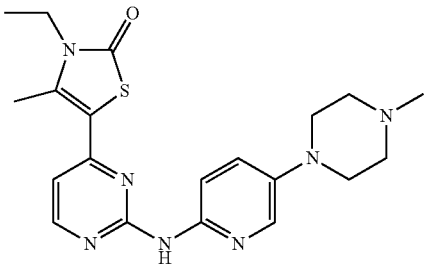 | 3-ethyl-4-methyl-5-(2-((5-(4-methylpiperazin-1-yl)pyridin-2-yl)amino)pyrimidin-4-yl)thiazol-2(3H)-one | 411.5 |
| 95. | 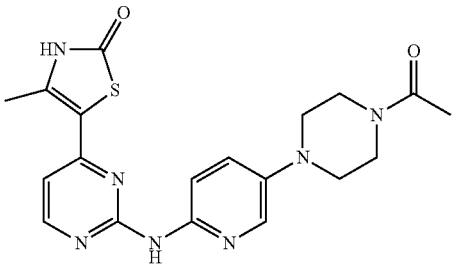 | 5-(2-((5-(4-acetylpiperazin-1-yl)pyridin-2-yl)amino)pyrimidin-4-yl)-4-methylthiazol-2(3H)-one | 411.5 |
| 96. | 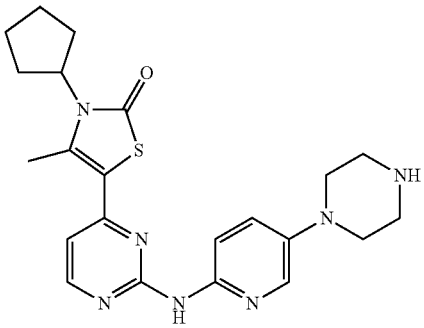 | 3-cyclopentyl-4-methyl-5-(2-((5-(piperazin-1-yl)pyridin-2-yl)amino)pyrimidin-4-yl)thiazol-2(3H)-one | 437.6 |
| 97. | 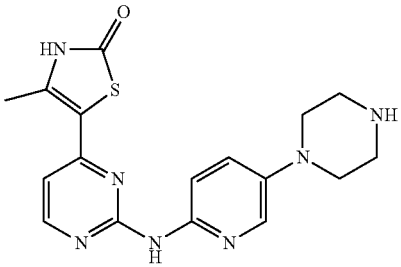 | 4-methyl-5-(2-((5-(piperazin-1-yl)pyridin-2-yl)amino)pyrimidin-4-yl)thiazol-2(3H)-one | 369.4 |
| 99. | 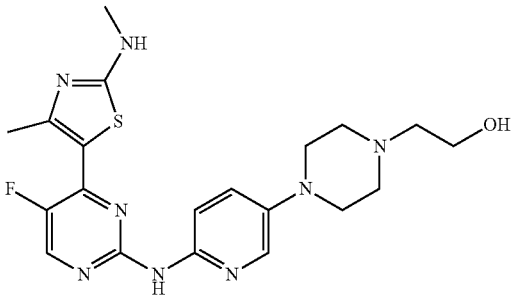 | 2-(4-(6-((5-fluoro-4-(4-methyl-2-(methylamino)thiazol-5-yl)pyrimidin-2-yl)amino)pyridin-3-yl)piperazin-1-yl)ethan-1-ol | 444.5 |

TABLE 1-continued

| Chemical structure of selected compounds of the present invention | | | |
|---|---|---|---|
| No. | Structure | Name | Mass |
| 100. | 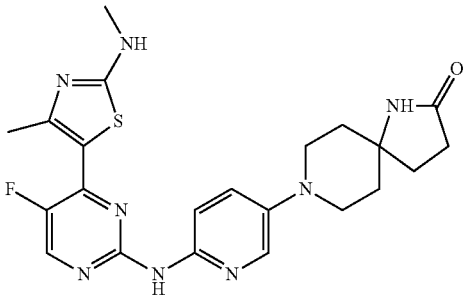 | 8-(6-((5-fluoro-4-(4-methyl-2-(methylamino)thiazol-5-yl)pyrimidin-2-yl)amino)pyridin-3-yl)-1,8-diazaspiro[4.5]decan-2-one | 468.6 |
| 101. | 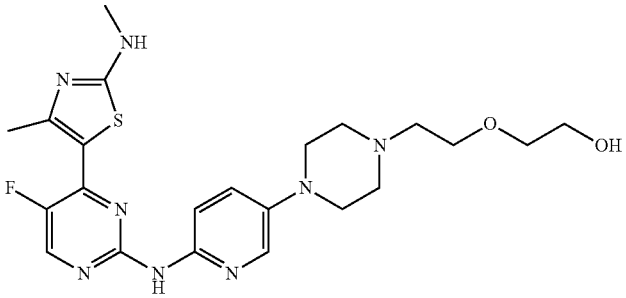 | 2-(2-(4-(6-((5-fluoro-4-(4-methyl-2-(methylamino)thiazol-5-yl)pyrimidin-2-yl)amino)pyridin-3-yl)piperazin-1-yl)ethoxy)ethan-1-ol | 488.6 |
| 102. | 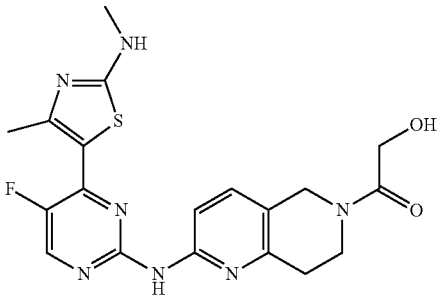 | 1-(2-((5-fluoro-4-(4-methyl-2-(methylamino)thiazol-5-yl)pyrimidin-2-yl)amino)-7,8-dihydro-1,6-naphthyridin-6(5H)-yl)-2-hydroxyethan-1-one | 429.5 |
| 103. | 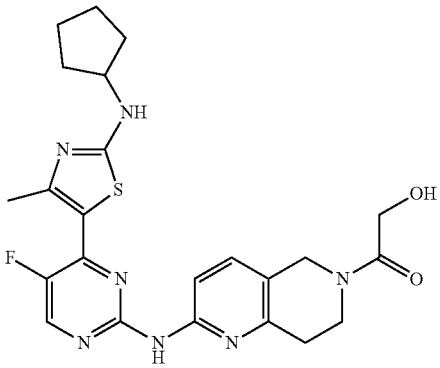 | 1-(2-((4-(2-(cyclopentylamino)-4-methylthiazol-5-yl)-5-fluoropyrimidin-2-yl)amino)-7,8-dihydro-1,6-naphthyridin-6(5H)-yl)-2-hydroxyethan-1-one | 483.6 |

TABLE 1-continued

| Chemical structure of selected compounds of the present invention | | | |
|---|---|---|---|
| No. | Structure | Name | Mass |
| 104. | 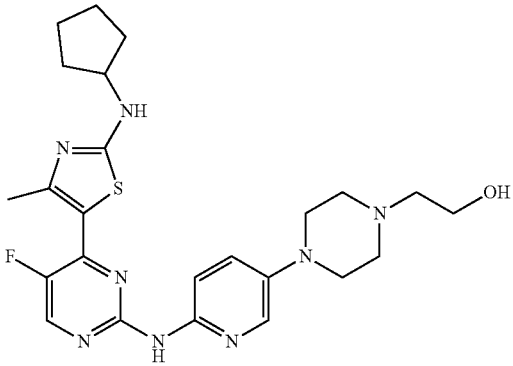 | 2-(4-(6-((4-(2-(cyclopentylamino)-4-methylthiazol-5-yl)-5-fluoropyrimidin-2-yl)amino)pyridin-3-yl)piperazin-1-yl)ethan-1-ol | 498.6 |
| 105. | 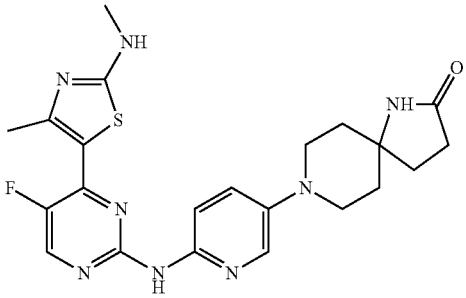 | 8-(6-((5-fluoro-4-(4-methyl-2-(methylamino)thiazol-5-yl)pyrimidin-2-yl)amino)pyridin-3-yl)-1,8-diazaspiro[4.5]decan-2-one | 468.6 |
| 106. | 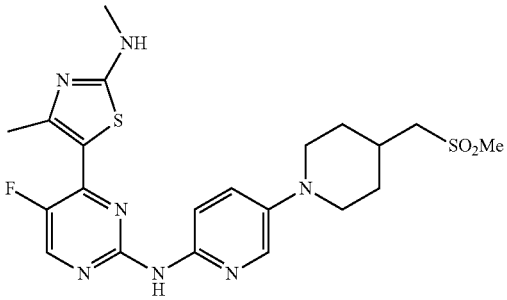 | 5-(5-fluoro-2-((5-(4-((methylsulfonyl)methyl)piperidin-1-yl)pyridin-2-yl)amino)pyrimidin-4-yl)-N,4-dimethylthiazol-2-amine | 491.6 |
| 107. | 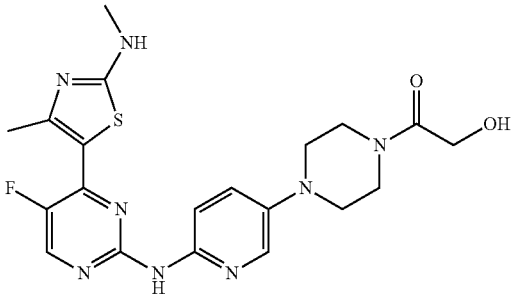 | 5-(5-fluoro-2-((5-(4-((methylsulfonyl)methyl)piperidin-1-yl)pyridin-2-yl)amino)pyrimidin-4-yl)-N,4-dimethylthiazol-2-amine | 458.5 |

TABLE 1-continued

Chemical structure of selected compounds of the present invention

| No. | Structure | Name | Mass |
|---|---|---|---|
| 108. | 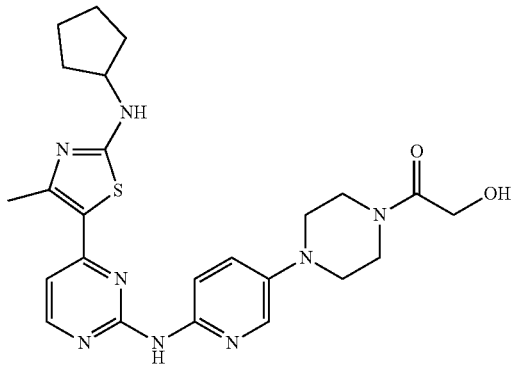 | 1-(4-(6-((4-(2-(cyclopentylamino)-4-methylthiazol-5-yl)pyrimidin-2-yl)amino)pyridin-3-yl)piperazin-1-yl)-2-hydroxyethan-1-one | 494.6 |

The compounds (and pharmaceutically acceptable salts, solvates and prodrugs thereof) may be administered in combination with one or more additional agent(s) for the treatment of cancer or another proliferative disease or condition. For example, the compounds may be used in combination with other anti-cancer agents in order to inhibit more than one cancer signalling pathway simultaneously so as to make cancer cells more susceptible to anti-cancer therapies (eg treatments with other anti-cancer agents, chemotherapy, radiotherapy or a combination thereof). As such, the compounds of formula I may be used in combination with one or more of the following categories of anti-cancer agents:

other anti-proliferative/antineoplastic drugs and combinations thereof, as used in medical oncology, such as alkylating agents (eg cis-platin, oxaliplatin, carboplatin, cyclophosphamide, nitrogen mustard, melphalan, chlorambucil, busulphan, temozolamide and nitrosoureas); antimetabolites (eg gemcitabine and antifolates such as fluoropyrimidines like 5-fluorouracil and tegafur, raltitrexed, methotrexate, cytosine arabinoside, fludarabine and hydroxyurea); antitumour antibiotics (eg anthracyclines such as adriamycin, bleomycin, doxorubicin, daunomycin, epirubicin, idarubicin, mitomycin-C, dactinomycin and mithramycin); antimitotic agents (eg vinca alkaloids such as vincristine, vinblastine, vindesine and vinorelbine and taxoids including taxol and taxotere and polokinase inhibitors); and topoisomerase inhibitors (eg epipodophyllotoxins such as etoposide and teniposide, amsacrine, topotecan and camptothecin);

cytostatic agents such as antioestrogens (eg tamoxifen, fulvestrant, toremifene, raloxifene, droloxifene and iodoxyfene), antiandrogens (eg bicalutamide, flutamide, nilutamide and cyproterone acetate), LHRH antagonists or LHRH agonists (eg goserelin, leuprorelin and buserelin), progestogens (eg megestrol acetate), aromatase inhibitors (eg as anastrozole, letrozole, vorazole and exemestane) and inhibitors of 5a-reductase such as finasteride;

anti-invasion agents (eg c-Src kinase family inhibitors such as 4-(6-chloro-2,3-methylenedioxyanilino)-7-[2-(4-methylpiperazin-1-yl)ethoxy]-5-tetrahydropyran-4-yloxyquinazoline (AZD0530; International Patent Publication No WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib) and bosutinib (SKI-606)), and metalloproteinase inhibitors including marimastat, inhibitors of urokinase plasminogen activator receptor function or antibodies to heparanase;

inhibitors of growth factor function (eg growth factor antibodies and growth factor receptor antibodies such as the anti-erbB2 antibody trastuzumab (Herceptintm™), the anti-EGFR antibody panitumumab, the anti-erbB1 antibody cetuximab (Erbitux, C225) and any growth factor or growth factor receptor antibodies disclosed by Stern et al. Critical reviews in oncology/haematology, 2005, Vol. 54, pp 11-29). Such inhibitors also include tyrosine kinase inhibitors such as inhibitors of the epidermal growth factor family (eg EGFR family tyrosine kinase inhibitors such as N-(3-chloro-4-fluorophenyl)-7-methoxy-6-(3-morpholinopropoxy) quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (eg Ras/Raf signalling inhibitors such as farnesyl transferase inhibitors including sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, PIt3 kinase inhibitors, CSF-IR kinase inhibitors, IGF receptor (insulin-like growth factor) kinase inhibitors; aurora kinase inhibitors (eg AZD1152, PH739358, VX-680, MLN8054, R763, MP235, MP529, VX-528 and AX39459) and cyclin dependent kinase inhibitors such as CDK2 and/or CDK9 inhibitors;

antiangiogenic agents such as those which inhibit the effects of vascular endothelial growth factor (eg the anti-vascular endothelial cell growth factor antibody bevacizumab (Avastin™) and VEGF receptor tyrosine kinase inhibitors such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within International Patent Publication No WO 00/47212), compounds such as those disclosed in International Patent Publication Nos WO97/22596, WO 97/30035, WO 97/32856 and WO 98/13354, and compounds that work by other mechanisms (eg linomide, inhibitors of integrin a vb3 function and angiostatin);

vascular damaging agents such as Combretastatin A4 and compounds disclosed in International Patent Publication Nos WO 99/02166, WO 00/40529, WO 00/41669, WO 01/92224, WO 02/04434 and WO 02/08213;

an endothelin receptor antagonist such as zibotentan (ZD4054) or atrasentan;

antisense therapies such as those which are directed to the targets listed above, such as ISIS 2503, an anti-ras antisense;

gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and immunotherapy approaches, including for example ex vivo and in vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Where used in combination with other anti-cancer agents, a compound of the present invention and the other anti-cancer agent can be administered in the same pharmaceutical composition or in separate pharmaceutical compositions. If administered in separate pharmaceutical compositions, the compound and the other anti-cancer agent may be administered simultaneously or sequentially in any order (eg within seconds or minutes or even hours (eg 2 to 48 hours)).

The present invention is typically applied to the treatment of cancer or another proliferative cell disease or condition in a human subject. However, the subject may also be selected from, for example, livestock animals (eg cows, horses, pigs, sheep and goats), companion animals (eg dogs and cats) and exotic animals (eg non-human primates, tigers, elephants etc).

Cancers and other proliferative cell diseases and conditions that may be treated in accordance with the present invention include biliary tract cancer, brain cancer (including glioblastomas and medulloblastomas), breast cancer, cervical cancer; choriocarcinoma, colonic cancer, endometrial cancer, oesophageal cancer, gastric cancer, haematological neoplasms (including acute lymphocytic leukemia (ALL)), chronic lymphocytic leukemia (CLL) and chronic myelogenous leukemia (CML), acute myeloid leukaemia (AML), multiple myeloma, AIDS-associated leukemias and adult T-cell leukemia lymphoma, intraepithelial neoplasms (including Bowen's disease and Paget's disease), liver cancer, lung cancer, lymphomas (including Hodgkin's disease and lymphocytic lymphomas), neuroblastomas, oral cancer (including squamous cell carcinoma), ovarian cancer (including those arising from epithelial cells, stromal cells, germ cells, and mesenchymal cells), pancreatic cancer, prostate cancer, colorectal cancer, sarcomas (including leiomyosarcoma, rhabdomyosarcoma, liposarcoma, fibrosarcoma, and osteosarcoma), skin cancer (including melanoma, Kaposi's sarcoma, basocellular cancer, and squamous cell cancer), testicular cancer (including germinal tumours such as seminoma, non-seminoma teratomas, and choriocarcinomas), stromal tumours, germ cell tumours, thyroid cancer (including thyroid adenocarcinoma and medullar carcinoma), and renal cancer (including adenocarcinoma and Wilms' tumour).

In some embodiments, the compounds of the present invention are used to treat cancers characterised by over-expression of CDK4 and/or cyclin D including, for example, lung cancer (Wu et al. J Transl Med 9:38 (2011)), breast cancer (An et al., Am J Pathol 154(1):113-118 (1999)), cancers of the central nervous system (CNS) and colorectal cancer (Ikeda et al., Jap J Clin Med 54(4):1054-1059 (1996)). CDK4 and/or cyclin Dover-expression may be determined by, for example, assessing the amount of mRNA encoding CDK4 and/or cyclin D in a suitable sample using any of the techniques well known to those skilled in the art (eg quantitative amplification techniques such as qPCR).

In some embodiments, the compounds of the present invention are used to treat cancers characterised by over-expression of CDK6 and/or cyclin D including, for example, T-cell acute lymphoblastic leukemia (ALL), colorectal cancer and medullablastoma (reviewed in Tadesse et al., Cell Cycle. 14(20):3220-30, 2015). CDK6 and/or cyclin Dover-expression may be determined by, for example, assessing the amount of mRNA encoding CDK6 and/or cyclin D in a suitable sample using any of the techniques well known to those skilled in the art (eg quantitative amplification techniques such as qPCR).

The compounds of the present invention may be formulated into a pharmaceutical composition with a pharmaceutically acceptable carrier, diluent and/or excipient. Examples of suitable carriers and diluents are well known to those skilled in the art, and are described in, for example, Remington's Pharmaceutical Sciences, Mack Publishing Co., Easton, Pa. 1995. Examples of suitable excipients for the various different forms of pharmaceutical compositions described herein may be found in the Handbook of Pharmaceutical Excipients, $2^{nd}$ Edition, (1994), Edited by A Wade and P J Weller. Examples of suitable carriers include lactose, starch, glucose, methyl cellulose, magnesium stearate, mannitol, sorbitol and the like. Examples of suitable diluents include ethanol, glycerol and water. The choice of carrier, diluent and/or excipient may be made with regard to the intended route of administration and standard pharmaceutical practice.

A pharmaceutical composition comprising a compound of the present invention may further comprise any suitable binders, lubricants, suspending agents, coating agents and solubilising agents. Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilising agents, dyes and even flavouring agents may be provided in the pharmaceutical composition. Examples of preservatives include sodium benzoate, sorbic acid and esters of p-hydroxybenzoic acid. Anti-oxidants and suspending agents may be also used.

A pharmaceutical composition comprising a compound of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration. For oral administration, particular use may be made of compressed tablets, pills, tablets, gellules, drops, and capsules. For other forms of administration, a pharmaceutical composition may comprise solutions or emulsions which may be injected intravenously, intraarterially, intrathecally, subcutaneously, intradermally, intraperitoneally or intramuscularly, and which are prepared from sterile or sterilisable solutions. A pharmaceutical composition comprising a compound of the present invention may also be in form of suppositories, pessaries, suspensions, emulsions, lotions, ointments, creams, gels, sprays, solutions or dusting powders. A pharmaceutical composition may be formulated in unit dosage form (ie in the form of discrete portions containing a unit dose, or a multiple or sub-unit of a unit dose).

The compounds of the present invention may be provided as a pharmaceutically acceptable salt including, for example, suitable acid addition or base salts thereof. A review of suitable pharmaceutical salts may be found in Berge et al., J Pharm Sci 66:1-19 (1977). Salts are formed, for example with strong inorganic acids such as mineral acids (eg sulfuric acid, phosphoric acid or hydrohalic acids), with strong organic carboxylic acids, such as alkanecarboxylic acids of 1 to 4 carbon atoms which are unsubstituted or substituted (eg by halogen), such as acetic acid, with saturated or unsaturated dicarboxylic acids (eg oxalic, malonic, succinic, maleic, fumaric, phthalic or tetraphthalic acid), with hydroxycarboxylic acids (eg ascorbic, glycolic, lactic, malic, tartaric or citric acid), with amino acids (eg aspartic or glutamic acid), with benzoic acid, or with organic sulfonic acids (eg ($C_1$-$C_4$)-alkyl- or aryl-sulfonic acids which are unsubstituted or substituted by, for example, halogen) such as methane- or p-toluene sulfonic acid).

The compounds of the present invention may be provided in their various crystalline forms, polymorphic forms and (an)hydrous forms. In this regard, it is well known to those skilled in the art that chemical compounds may be isolated in any of such forms by slightly varying the method of purification and or isolation from the solvents used in the synthetic preparation of such compounds.

The present invention further provides a method of synthesising a compound according to the present invention, or a pharmaceutically acceptable salt, solvate or prodrug thereof.

With regard to the description of the synthetic methods described below and in the referenced synthetic methods that are used to prepare starting materials, it will be understood by those skilled in the art that all proposed reaction conditions, including choice of solvent, reaction atmosphere, reaction temperature, duration of the experiment and workup procedures, can be readily selected. Moreover, it will be understood by those skilled in the art that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the examples hereinafter. Alternatively, necessary starting materials may be obtainable by analogous procedures to those illustrated which are within the ordinary skill of those skilled in the art. Further, it will be appreciated that during the synthesis of the compounds, in the processes described below, or during the synthesis of certain starting materials, it may be desirable to protect certain substituent groups to prevent their undesired reaction. Those skilled in the art will readily recognise when such protection is required, and how such protecting groups may be put in place, and later removed. Examples of protecting groups are described in, for example, Protective Groups in Organic Synthesis by Theodora Green (publisher: John Wiley & Sons). Protecting groups may be removed by any convenient method well known to those skilled in the art as appropriate for the removal of the protecting group in question, such methods being chosen so as to effect removal of the protecting group with the minimum disturbance of groups elsewhere in the molecule. Thus, if reactants include, for example, groups such as amino, carboxyl or hydroxyl, it may be desirable to protect the group in some of the reactions mentioned herein.

The compounds of the present invention may be prepared by, for example, the general synthetic methodologies described in International Patent Publication No WO 2013/156780, which is herein incorporated by reference.

In a further of the present invention, a method of synthesising a compound of the present invention (or a pharmaceutically acceptable salt, solvate or prodrug thereof) is provided wherein the method comprises:

a) reacting a compound of formula IV:

IV

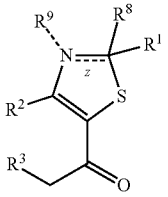

wherein z represents an optional bond such that the bond between N and the adjacent carbon atom can be a single or double bond; and $R^1$, $R^2$, $R^3$, $R^8$ and $R^9$ are as defined in the first aspect;

with a compound of formula V:

V

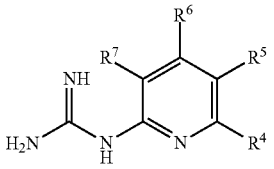

wherein $R^4$, $R^5$, $R^6$ and $R^7$ are as defined in the first aspect; and if necessary b) removing any protecting groups present, and/or forming a pharmaceutically acceptable salt, solvate or prodrug thereof.

The coupling reaction between the compound of formula IV and formula V may take place in the presence of a suitable solvent or solvent mixture. Those skilled in the art will be able to readily select a suitable solvent or solvent mixture for use in this reaction. Examples of suitable solvents include alcohols, acetonitrile, halogenated solvents, etc.

In addition, those skilled in the art will be able to select appropriate reaction conditions to use in the coupling reaction between the compound of formula IV and formula V. However, typically, the reaction will be carried out in anhydrous conditions and in the presence of an inert atmosphere, such as argon or nitrogen. The reaction may also be carried out an elevated temperature, such as, for example, within the range of 80 to 180 C for a suitable time period of, for example, 20 minutes to 48 hours. Suitably, the reaction is carried out under microwave heating, for example, at 80 to 180 C for 20 minutes to 1.5 hour.

The resultant compound can be isolated and purified using techniques well known to those skilled in the art.

The method of synthesising a compound of the present invention (or a pharmaceutically acceptable salt, solvate or prodrug thereof) may further comprise:

c) subjecting the compound of formula I to a salt exchange (particularly in situations where the compound is formed as a mixture of different salt forms).

The salt exchange may comprise immobilising the compound on a suitable solid support or resin, and eluting the compound with an appropriate acid to yield salt of the compound of formula I (II or III).

An example of a particularly suitable method for synthesising a compound of the present invention is shown as Scheme 1 below.

Scheme 1

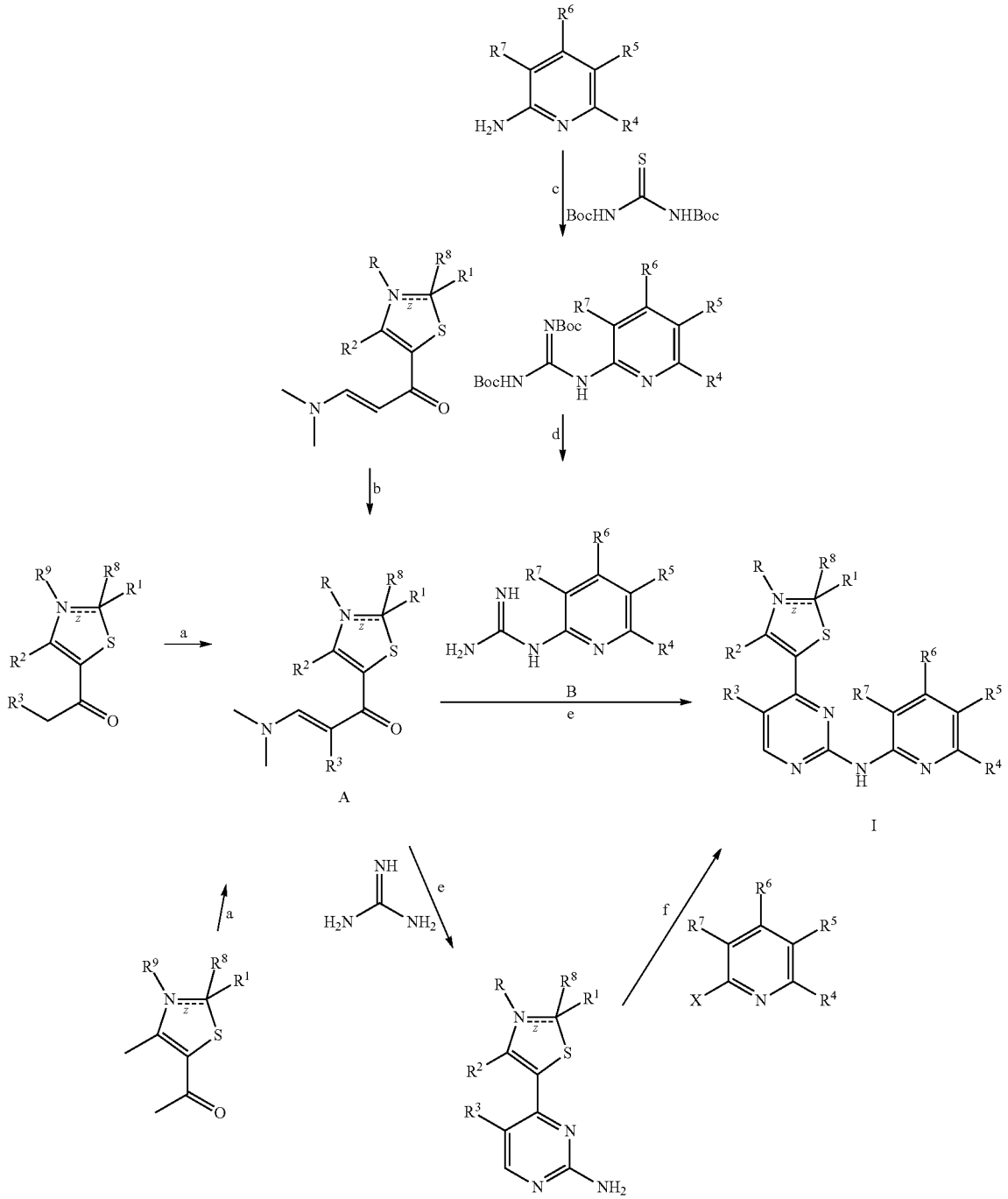

wherein the general reaction conditions are: (a) DMF-DMA or Bredereck's reagent, reflux; (b) Select Fluor, MeOH; (c) $Et_3N$, $HgCl_2$, DCM; (d) TFA/DCM (1:1), reflux; (e) A, B, NaOH, 2-methoxyethanol, microwave and (f) $Pd_2dba_3$, xantphose, t-BuONa, dioxane, microwave.

The invention is hereinafter described with reference to the following, non-limiting examples and accompanying figures.

EXAMPLES

Example 1

Synthesis

General $^1H$ and $^{13}C$ NMR spectra were recorded at 300 K on a Bruker AVANCE III 500 spectrometer ($^1H$ at 500 MHz and $^{13}C$ NMR at 125 MHz). $^1H$ and $^{13}C$ NMR spectra were referenced to $^1H$ signals of residual non-deuterated solvents (or tetramethylsilane) and $^{13}C$ signals of the deuterated solvents respectively. High resolution mass spectra were recorded on an AB SCIEX TripleTOF® 5600 mass spectrometer, and ionization of all samples was carried out using ESI. The purity of compounds was determined by analytical HPLC, and was greater than 95%. Analytic HPLC was carried out on a Shimadzu Prominence UFLC (UltraFast Liquid Chromatograph) system with a CBM-20A communications bus module, a DGU-20$A_{5R}$ degassing unit, an LC-20AD liquid chromatograph pump, an SIL-20$A_{HT}$ autosampler, an SPD-M20A photo diode array detector, a CTO-20A column oven and a Phenomenex Kinetex 5 u C18 100A 250 mm×4.60 mm column using Method A (gradient 5 to 95% MeOH containing 0.1% FA over 7 min, followed by 95% MeOH containing 0.1% FA over 13 min at a flow rate of 1 mL/min), Method B (gradient 5 to 95% MeCN containing 0.1% FA over 7 min followed by 95% MeCN containing 0.1% FA over 13 min, at a flow rate of 1 mL/min).

1-(4-(6-((4-(2,4-Dimethylthiazol-5-yl)pyrimidin-2-yl)amino)pyridin-3-yl)piperazin-1-yl)ethan-1-one (1)

To a solution of acetylpiperazine (5.00 g, 39.0 mmol) and 5-bromo-2-nitropyridine (5.00 g, 24.6 mmol) in DMSO (10 mL) was added triethylamine (10.2 mL, 73.9 mmol). The reaction mixture was heated at 120° C. for 16 h, cooled down to room temperature and triturated with EtOAc. The formed solid was filtered and washed with EtOAc (10 mL) and $H_2O$ (30 mL) to give the first portion of 1-(4-(6-nitropyridin-3-yl)piperazin-1-yl)ethan-1-one as a yellow solid. The filtrate and washing were combined and extracted with DCM (3×100mL). The organic extracts were combined, dried over $Na_2SO_4$ and concentrated under reduced pressure. The residue was purified by chromatography (silica gel, DCM ramping to DCM:MeOH=94:6) to give the second portion of 1-(4-(6-nitropyridin-3-yl)piperazin-1-yl) ethan-1-one. $^1H$ NMR ($CDCl_3$) δ 2.16 (s, 3H), 3.47 (t, 2H, J 5.5), 3.52 (t, 2H, J 5.5), 3.71 (t, 2H, J 5.5), 3.83 (t, 2H, 5.5), 7.23 (dd, 1H, J 9.5 & 3.0), 8.14 (d, 1H, 3.0), 8.20 (d, 1H, J 9.0). HRMS (ESI) 251.1130 ([M+H]$^+$); calcd. for $C_{11}H_{15}N_4O_3^+$ ([M+H]$^+$) 251.1139.

To a suspension of 1-(4-(6-nitropyridin-3-yl)piperazin-1-yl)ethan-1-one (2.51 g, 10.0 mmol) in MeOH (200 mL) was added 10% Pd/C (107 mg, 0.100 mmol, 1 mol %). The reaction mixture was bubbled with $H_2$ at room temperature for 5 h and filtered through a pad of Celite®. The solids were washed with MeOH (50 mL). The filtrate and washing were combined and concentrated under reduced pressure and in vacuo to give 1-(4-(6-aminopyridin-3-yl)piperazin-1-yl) ethan-1-one as a brownish solid (2.20 g, 100%), which was used in the next step without purification. HRMS (ESI): m/z 221.1390 [M+H]$^+$; calcd. for $C_{11}H_{17}N_4O^+$ [M+H]$^+$ 221.1397.

To a solution of 1-(4-(6-aminopyridin-3-yl)piperazin-1-yl)ethan-1-one (2.21 g, 10.0 mmol), N',N'-bis-Boc-S-methylisothiourea (3.50 g, 12.0 mmol) and triethylamine (4.90 mL, 35.1 mmol) in DCM (100 mL) on an ice bath was added $HgCl_2$ (5.45 g, 20.1 mmol). After stirring on an ice bath for 0.5 h, the reaction mixture was warmed to room temperature, stirred for 12 h and filtered through a pad of Celite®. The solids were washed with DCM (50 mL). The filtrate and washing were combined and concentrated under reduced pressure. The residue was purified by chromatography (silica gel, DCM:MeOH=95:5 ramping to 90:10) to give 1-acetyl-4-(6-(2,3-bis(tert-butoxyearbonyl)guanidino)pyridin-3-yl)piperazine as a light yellow solid (3.82 g, 82%). $^1H$ NMR ($CDCl_3$) δ 1.53 (s, 18 H), 2.14 (s, 3H), 3.13 (t, 2H, J 5.5), 3.18 (t, 2H, J 5.5), 3.63 (t, 2H, J 5.5), 3.78 (t, 2H, J 5.5), 7.29 (dd, 1H, J 9.0 & 3.0), 7.87 (d, 1H, J 7.5), 7.99 (d, 1H, J 2.5), 10.90 (br s, 1H) 11.58 (br s, 1H). HRMS (ESI): m/z 463.2668 [M+H]$^+$; calcd. for $C_{22}H_{35}N_6O_5^+$ [M+H]$^+$ 463.2663.

To a solution of 1-acetyl-4-(6-(2,3-bis(tert-butoxycarbonyl)guanidino)pyridin-3-yl)piperazine (724 mg, 1.56 mmol) in DCM (5 mL) was added TFA (5 mL). The reaction mixture was heated at reflux for 16 h and concentrated under reduced pressure. The residue was redissolved MeOH (50 mL), and a suspension of excess Ambersep®, 900 resin (hydroxide form, pre-swelled with $H_2O$ for 30 min and MeOH for 30 min) in MeOH (50 mL) was added. The mixture was stirred at room temperature overnight and filtered, and the solid was washed with MeOH (50 mL). The filtrate and washing were combined and concentrated under reduced pressure to give 1-(5-(4-acetylpiperazin-1-yl)pyridin-2-yl)guanidine as a beige solid (410 mg, 100%), which was directly used in the next step without further purification. MS (ESI): m/z 263.2 [M−TFA+H]$^+$.

To a mixture of crude 1-(5-(4-acetylpiperazin-1-yl)pyridin-2-yl)guanidine trifluoroacetate (1.08 g, 4.00 mmol) and (E)-3-(dimethylamino)-1-(2,4-dimethylthiazol-5-yl)prop-2-en-1-one (420 mg, 2.00 mmol) in 2-methoxy ethanol (6 mL) was added NaOH (160 mg, 4.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH=92:8) and recrystallised with DCM and hexane to give compound 1 as a yellow solid (100 mg, 12%). $^1H$ NMR ($CDCl_3$) δ 2.09 (s, 3H), 2.64 (s, 3H), 2.65 (s, 3H), 3.20 (m, 4H), 3.58 (t, 2H, J 5.0), 3.74 (t, 2H, J 5.0), 6.91 (d, 1H, J 5.5), 7.31 (dd, 1H, J 9.0 & 3.0), 7.98 (d, 1H, J 2.5), 8.14 (s, 1H), 8.25 (d, 1H, J 9.0), 8.42 (s, 1H, J 5.5). $^{13}C$ NMR ($CDCl_3$) δ 18.3, 19.6, 21.5, 41.4, 46.3, 50.2, 50.5, 109.4, 113.2, 127.4, 131.4, 137.5, 142.5, 146.9, 152.6, 158.7, 159.0, 159.1, 167.1, 169.1. HRMS (ESI): m/z 410.1763 [M+H]$^+$; calcd. for $C_{20}H_{24}N_7OS^+$ [M+H]$^+$ 410.1758 Anal. RP-HPLC Method A: $t_R$ 8.22 min, purity>99%, Method B: $t_R$ 2.81 min, purity>99%.

4-(2,4-Dimethylthiazol-5-yl)-N-(5-(piperazin-1-yl) pyridin-2-yl)pyrimidin-2-amine (2)

To a suspension of 1 (71.0 mg, 0.17 mmol) in methanol HCl (32%, 3 mL) was added and reflexed overnight. The reaction mixture was concentrated and purified by chromatography (silica gel, DCM ramping to DCM:MeOH: $NH_4OH$)=90:10:1) to give 2 as a yellow solid (49 mg, 77%). $^1H$ NMR (DMSO-$d_6$) δ 2.63 (s, 3H), 2.65 (s, 3H), 3.11 (t, 4H, J 5.5), 3.26 (t, 4H, J 4.5), 7.11 (d, 1H, J 5.0), 7.49 (dd, 1H, J 9.0 & 3.0), 8.05 (d, 1H, J 3.0), 8.10 (d, 1H, J 9.0), 8.53 (d, 1H, J 5.5), 9.70 (br, 1H). HRMS (ESI): m/z 368.1653 $[M+H]^+$; calcd. for $C_{18}H_{22}N_7S^+$ $[M+H]^+$368.1652 Anal. RP-HPLC Method A: $t_R$ 8.00 min, purity>98%, Method B: $t_R$ 2.88 min, purity>96%.

The following compounds were synthesised by an analogous route.

4-(2,4-dimethylthiazol-5-yl)-N-(5-(4-methylpiperazin-1-yl)pyridin-2-yl)pyrimidin-2-amine (3)

To a mixture of crude 1-(5-(4-methylpiperazin-1-yl)pyridine-2-yl)guanidine trifluoroacetate (468 mg, 2.00 mmol) and (E)-3-(dimethylamino)-1-(2,4-dimethylthiazol-5-yl) prop-2-en-1-one (210 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM: MeOH=92:8) and recrystallised with DCM and hexane to give 2 as a yellow solid (119 mg, 31%). m.p. 183-184° C. $^1H$ NMR ($CDCl_3$) δ 2.36 (s, 3H), 2.60 (t, 4H, J 5.0), 2.70 (s, 3H), 2.71 (s, 3H), 3.19 (t, 4H, J 5.0), 6.95 (d, 1H, J 5.0), 7.37 (dd, 1H, J 9.0 & 3.0), 8.05 (d, 1H, J 2.5), 8.23 (br, 1H), 8.27 (d, 1H, J 9.0), 8.48 (d, 1H, J 5.0). HRMS (ESI): m/z 382.1788 $[M+H]^+$; calcd. for $C_{19}H_{24}N_7S^+$ $[M+H]^+$ 382.1808. Anal. RP-HPLC Method A: $t_R$ 8.54 min, purity>99%, Method B: $t_R$ 3.23 min, purity>99%.

4-(2,4-Dimethylthiazol-5-yl)-2-((5-(piperazin-1-yl) pyridin-2-yl) amino) pyrimidine-5-carbonitrile (4)

To a mixture of crude 1-(5-(piperazin-1-yl)pyridin-2-yl) guanidine trifluoroacetate (441 mg, 2.00 mmol) and (E)-3-(dimethylamino)-2-(2,4-dimethylthiazole-5-carbonyl)acrylonitrile (235 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH=95:5) and recrystallised with DCM and hexane to give 4 as a yellow solid (90 mg, 23%). m.p. 110-113° C. $^1H$ NMR (DMSO-$d_6$) δ 2.91 (s, 4H, thiazole-$CH_3$ & piperazine-NH), 3.11 (s, 3H), 3.27 (t, 4H, J 4.5), 3.48 (t, 4H, J 4.0), 7.84 (dd, 1H, J 9.0 & 3.0), 8.31 (d, 1H, J 9.0), 8.48 (d, 1H, J 2.0) , 9.33 (s, 1H), 11.13 (s, 1H). HRMS (ESI): m/z 393.1597$[M+H]^+$; calcd. for $C_{19}H_{21}N_8S^+$ $[M+H]^+$ 393.1604. Anal. RP-HPLC Method A: $t_R$ 9.18 min, purity>95%; Method B: $t_R$ 7.68 min, purity>96%.

4-(2,4-Dimethylthiazol-5-yl)-2-((5-(4-methylpiperazin-1-yl)pyridin-2-yl)amino)pyrimidine-5-carbonitrile (5)

To a mixture of crude 1-(5-(4-methylpiperazin-1-yl)pyridine-2-yl)guanidine trifluoroacetate (468 mg, 2.00 mmol) and (E)-3-(dimethylamino)-2-(2,4-dimethylthiazole-5-carbonyl)acrylonitrile (235 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM: MeOH=90:10) and recrystallised with MeOH to give 5 as a brown solid (114 mg, 28%). m.p. 112-114° C. $^1H$ NMR ($CDCl_3$) (δ 2.37 (s, 3H), 2.60 (t, 4H, J 5.0), 2.63 (s, 3H), 2.76 (s, 3H), 3.21 (t, 4H, J 5.0), 7.33 (dd, 1H, J 9.0 & 3.0), 8.13 (s, 1H), 8.20 (d, 1H, J 9.0), 8.76 (s, 1H), 8.76 (s, 1H). HRMS (ESI): m/z 407.1772 $[M+H]^+$; calcd. for $C_{19}H_{21}N_8S^+$ $[M+H]^+$ 407.1761. Anal. RP-HPLC Method A: $t_R$ 9.58 min, purity 100%; Method B: $t_R$ 8.18 min, purity 100%.

2-((5-(4-Acetylpiperazin-1-yl) pyridin-2-yl) amino)-4-(2, 4-dimethylthiazol-5-yl) pyrimidine-5-carbonitrile (6)

To a mixture of crude 1-(5-(4-acetylpiperazin-1-yl)pyridin-2-yl)guanidine trifluoroacetate (524 mg, 2.00 mmol) and (E)-3-(dimethylamino)-2-(2,4-dimethylthiazole-5-carbonyl) acrylonitrile (235 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH=90:10) and recrystallised with DCM and hexane to give 6 as a yellow solid (150 mg, 34%). m.p. 99-101° C. $^1H$ NMR (DMSO-$d_6$) (δ 1.79 (s, 3H), 2.25 (s, 3H), 2.45 (s, 3H), 2.85 (d, 2H, J 4.0), 2.92 (s, 2H), 3.33 (d, 4H, J 4.0), 7.22 (dd, 1H, J 9.0 & 3.0), 7.67 (d, 1H, J 9.0), 7.85 (d, 1H, J 2.5), 8.68 (s, 1H), 10.47 (s, 1H). HRMS (ESI): m/z 435.1700 $[M+H]^+$; calcd. for $C_{22}H_{29}N_8S^+$ $[M+H]^+$ 435.1710. Anal. RP-HPLC Method A: $t_R$ 10.92 min, purity>97%; Method B: $t_R$ 8.69 min, purity>96%.

4-(2-Ethyl-4-methylthiazol-5-yl)-N-(5-(piperazin-1-yl)pyridin-2-yl)pyrimidin-2-amine (7)

To a mixture of crude 1-(5-(piperazin-1-yl)pyridin-2-yl) guanidine trifluoroacetate (441 mg, 2.00 mmol) and (E)-3-(dimethylamino)-1-(2-ethyl-4-methylthiazol-5-yl)prop-2-en-1-one (224 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH=91:9) and recrystallised with MeOH to give 7 as a yellow solid (35 mg, 9%). $^1H$ NMR (DMSO-$d_6$) δ 1.32 (t, 3H, J 7.5), 2.65 (s, 3H), 2.98 (q, 2H, J 7.5), 3.26 (t, 4H, J 2.5), 3.34 (app s, 4H), 7.13 (d, 1H, J 5.0), 7.52 (dd, 1H, J 9.5 & 3.5), 8.07 (d, 1H, J 3.0),), 8.11 (d, 1H, J 9.0), 8.53 (d, 1H, J 5.5), 8.66 (s, 1H), 9.65 (s, 1H). HRMS (ESI): m/z 382.1810 $[M+H]^+$; calcd. for $C_{19}H_{24}N_7S^+[M+H]^+$ 382.1808. Anal. RP-HPLC Method A: $t_R$ 12.55 min, purity>99%; Method B: $t_R$ 3.71 min, purity>98%.

4-(2-Ethyl -4-methylthiazol-5-yl)-N-(5-(4-methylpiperazin-1-yl)pyridin-2-yl)pyrimidin-2-amine (8)

To a mixture of crude 1-(5-(4-methylpiperazin-1-yl)pyridine-2-yl)guanidine trifluoroacetate (468 mg, 2.00 mmol) and (E)-3-(dimethylamino)-1-(2-ethyl-4-methylthiazol-5-yl)prop-2-en-1-one (224 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM: MeOH=91:9) and recrystallised with MeOH to give 8 as a yellow solid (50 mg, 13%).

$^1$H NMR ($CDCl_3$) δ 1.41 (t, 3H, J 7.5), 2.34 (s, 3H), 2.58 (t, 4H, J 5.0), 2.69 (s, 3H), 3.00 (q, 2H, J 7.5), 3.18 (t, 4H, J 5.0), 6.93 (d, 1H, J 5.0), 7.35 (dd, 1H, J 9.0 & 3.0), 8.12 (d, 1H, J 3.0), ), 8.28 (d, 1H, J 9.0), 8.52 (d, 1H, J 5.5), 8.97 (s, 1 H). HRMS (ESI): m/z 396.1980 $[M+H]^+$; calcd. for $C_{19}H_{24}N_7S^+[M+H]^+$396.1965. Anal. RP-HPLC Method A: $t_R$ 12.58 min, purity>99%; Method B: $t_R$ 3.86 min, purity>96%.

4-(2-Ethyl-4-methylthiazol-5-yl)-N-(5-(4-ethylpiperazin-1-yl)pyridin-2-yl)pyrimidin-2-amine (9)

To a mixture of crude 1-(5-(4-ethylpiperazin-1-yl)pyridin-2-yl)guanidine trifluoroacetate (497 mg, 2.00 mmol) and (E)-3-(dimethylamino)-1-(2-ethyl-4-methylthiazol-5-yl) prop-2-en-1-one (224 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM: MeOH=95:5) and recrystallised with MeOH to give 9 as a yellow solid (51 mg, 13%). $^1$H NMR ($CDCl_3$) δ 1.13 (t, 3H, J 7.5) 1.42 (t, 3H, J 7.5), 2.49 (q, 2H, J 7.0), 2.63 (t, 4H, J 5.0), 2.70 (s, 3H), 3.02 (q, 2H, J 8.0$_3$), 3.20 (t, 4H, J 5.0), 6.95 (d, 1H, J 5.0), 7.36 (dd, 1H, J 9.0 & 3.0), 8.07 (d, 1H, J 3.0), ), 8.28 (d, 1H, J 9.5), 8.40 (s, 1H), 8.49 (d, 1H, J 5.5). HRMS (ESI): m/z 410.2129 $[M+H]^+$; calcd. for $C_{21}H_{28}N_7S^+$ $[M+H]^+$ 410.2121. Anal. RP-HPLC Method A: $t_R$ 12.61 min, purity>99%; Method B: $t_R$ 3.82 min, purity>94%.

1-(4-(6-((4-(2-Ethyl-4-methylthiazol-5-yl)pyrimidin-2-yl)amino)pyridin-3-yl)piperazin-1-yl)ethan-1-one (10)

To a mixture of crude 1-(5-(4-acetylpiperazin-1-yl)pyridin-2-yl)guanidine trifluoroacetate (524 mg, 2.00 mmol) and (E)-3-(dimethylamino)-1-(2-ethyl-4-methylthiazol-5-yl) prop-2-en-1-one (224 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM: MeOH=95:5) and recrystallised with MeOH to give 10 as a yellow solid (175 mg, 41%). $^1$H NMR ($CDCl_3$) (δ 1.43 (t, 3H, J 7.5), 2.15 (s, 3H), 2.71 (d, 3H, J 2.5), 3.03 (q, 2H, J 8.0), 3.12 (t, 2H, J 5.0), 3.15 (t, 2H, J 5.0), 3.65 (s, 6H), 3.80 (t, 2H, J 5.0), 3.78 (t, 2H, J 5.0), 6.98 (d, J 5.5, 1H), 7.37 (dd, 1H, J 9.0 & 3.0), 8.03 (d, 1H, J 3.0), 8.05 (s, 1H), 8.32 (d, 1H, J 9.0), 8.48 (d, J 5.5, 1H). HRMS (ESI): m/z 424.1932 $[M+H]^+$; calcd. for $C_{21}H_{26}N_7OS^+$ $[M+H]^+$ 424.1914. Method A: $t_R$ 14.52 min, purity 100%; Method B: $t_R$ 10.33 min, purity 100%.

1-(4-(6-((5-Chloro-4-(2-ethyl-4-methylthiazol-5-yl) pyrimidin-2-yl)amino)pyridin-3-yl)piperazin-1-yl) ethan-1-one (11)

To a mixture of crude 1-(5-(4-acetylpiperazin-1-yl)pyridin-2-yl)guanidine trifluoroacetate (524 mg, 2.00 mmol) and (E)-2-chloro-3-(dimethylamino)-1-(2-ethyl-4-methylthiazol-5-yl)prop-2-en-1-one (259 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH=96:4) and recrystallised with MeOH to give 11 as yellow solid (30 mg, 7%).

$^1$H NMR ($CDCl_3$) δ 1.44 (t, 3H, J 7.5), 2.15 (s, 3H), 2.54 (s, 3H), 3.05 (q, 2H, J 7.5), 3.10 (t, 2H, J 5.0), 3.13 (t, 2H, J 5.0), 3.64 (t, 2H, J 4.5), 3.79 (t, 2H, J 5.0), 7.32 (dd, 1H, J 9.0 & 3.0), 8.03 (d, 1H, J 2.5), 8.22 (d, 1H, J 9.0), 8.31 (d, J 5.5, 1H), 8.49 (s, 1H, NH). HRMS (ESI): m/z 458.1525 $[M+H]^+$; calcd. for $C_{21}H_{25}ClN_7OS^+$ $[M+H]^+$ 458.1524. Anal. RP-HPLC Method A: $t_R$ 11.26 min, purity>99%; Method B: $t_R$ 8.76 min, purity>98%.

4-(2-Ethyl-4-methylthiazol-5-yl)-N-(5-morpholinopyridin-2-yl)pyrimidin-2-amine (12)

To a mixture of crude 1-(5-morpholinopyridin-2-yl)guanidine trifluoroacetate (442 mg, 2.00 mmol) and (E)-3-(dimethylamino)-1-(2-ethyl-4-methylthiazol-5-yl)prop-2-en-1-one (224 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH=94:6) and recrystallised with MeOH to give 12 as a yellow solid (61 mg, 16%). $^1$H NMR ($CDCl_3$) δ 1.43 (t, 3H, J 7.5), 2.71 (d, 3H, J 2.5), 3.03 (q, 2H, J 7.5), 3.14 (t, 4H, J 5.0), 3.89 (t, 4H, J 5.0), 6.97 (d, J 5.0, 1H), 7.35 (dd, 1H, J 9.0 & 3.0), 7.99 (s, 1H), 8.02 (d, 1H, J 2.5), 8.30 (d, 1H, J 9.0), 8.47 (d, J 5.5, 1H). HRMS (ESI): m/z 383.1656 $[M+H]^+$; calcd. for $C_{19}H_{23}N_6OS^+$ $[M+H]^+$ 383.1649. Anal. RP-HPLC Method A: $t_R$ 14.71 min, purity>98%; Method B: $t_R$ 10.48 min, purity>97%.

4-(2-Isopropyl-4-methylthiazol-5-yl)-N-(5-(piperazin-1-yl)pyridin-2-yl)pyrimidin-2-amine (13)

To a suspension of N-(5-(4-ethylpiperazin-1-yl)pyridin-2-yl)-4-(2-isopropyl-4-methylthiazol-5-yl)pyrimidin-2-amine (150 mg, 0.34 mmol) in methanol HCl (32%, 3 mL) was added and reflexed overnight. The reaction mixture was concentrated and purified by chromatography (silica gel, DCM ramping to DCM:MeOH:$NH_4OH$)=90:10:1) to give 13 as a yellow solid (108 mg, 80%). $R_F$ (DCM:MeOH=9:1+10 drops of 32% aqueous ammonia) 0.10. $^1$H NMR ($CDCl_3$) δ 1.43 (d, 6H, J 7.0), 1.65 (br, 1H), 2.71 (s, 3H), 3.07 (t, 4H, 2.0), 3.11 (t, 4H, J 3.0), 3.30 (m, 1H), 6.96 (d, 1H, J 5.5), 7.36 (dd, 1H, J 9.0 & 3.0), 7.97 (s, 1H), 8.02 (d, 1H, J 3.0), 8.28 (d, 1H, J 9.0), 8.46 (d, 1H, J 5.5). HRMS (ESI): m/z 396.1961 $[M+H]^+$; calcd. for $C_{20}H_{26}N_7S^+$ $[M+H]^+$ 396.1965. Anal. RP-HPLC Method A: $t_R$ 9.08 min, purity>98%; Method B: $t_R$ 7.44 min, purity 100%.

4-(2-Isopropyl-4-methylthi azol-5-yl)-N-(5-(4-methylpiperazin-1-yl)pyridin-2-yl)pyrimidin-2-amine (14)

To a mixture of crude 1-(5-(4-methylpiperazin-1-yl)pyridine-2-yl)guanidine trifluoroacetate (468 mg, 2.00 mmol) and (E)-3-(dimethylamino)-1-(2-isopropyl-4-methylthiazol-5-yl)prop-2-en-1-one (238 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM: MeOH=90:10) and recrystallised with MeOH to give 14 as a yellow solid (200 mg, 48.9). $^1$HNMR (DMSO-$d_6$) δ 1.34 (d, 6H, J 7), 2.21 (s, 1H), 2.45 (t, 4H, J 5), 2.63 (s, 3H), 3.11 (t, 4H, J 4.5), 3.25 (m, 1H), 7.09 (d, 1H, J 5.5), 7.44 (dd, 1H, J 9.5 & 3.0), 8.01 (d, 1H, J 3.0), 8.07 (d, 1H, J 9.5), 8.52 (d, 1H, J 5.5), 9.66 (s, 1H). HRMS (ESI): m/z 410.121 [M+H]$^+$; calcd. for $C_{21}H_{28}N_7S^+$ [M+H]$^+$ 410.2121. Anal. RP-HPLC Method A: $t_R$ 9.14 min, purity>97%; Method B: $t_R$ 7.53 min, purity 100%.

N-(5-(4-Ethylpiperazin-1-yl)pyridin-2-yl)-4-(2-isopropyl-4-methylthiazol-5-yl)pyrimidin-2-amine (15)

To a mixture of crude 1-(5-(4-ethylpiperazin-1-yl)pyridin-2-yl)guanidine trifluoroacetate (496.6 mg, 2.00 mmol) and (E)-3-(dimethylamino)-1-(2-isopropyl-4-methylthiazol-5-yl)prop-2-en-1-one (238 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM: MeOH=93:7) to give 15 as a light yellow solid (178 mg, 42%). $^1$H NMR ($CDCl_3$)δ 1.14 (t, 3H, J 7.0), 1.43 (d, 6H, J 7.0), 2.50 (q, 3H, J 7.0), 2.64 (t, 4H, J 5.0), 2.71 (s, 3H), 3.20 (t, 4H, J 5.0), 3.30 (m, 1H), 6.96 (d, 1H, J 5.5), 7.36 (dd, 1H, J 9.5 & 3.0), 8.05 (d, 1H, J 2.5), 8.17 (s, 1H), 8.33 (d, 1H, J 9.5), 8.47 (d, 1H, J 5.5). HRMS (ESI): m/z 424.2298 [M+H]$^+$; calcd. for $C_{22}H_{30}N_7S^+$ [M+H]$^+$ 424.2278. Anal. RP-HPLC Method A: $t_R$ 9.18 min, purity>99%; Method B: $t_R$ 7.15 min, purity>98%.

1-(4-(6-((4-(2-Isopropyl-4-methylthiazol-5-yl)pyrimidin-2-yl)amino)pyridin-3-yl)piperazin-1-yl) ethan-1-one (16)

To a mixture of crude 1-(5-(4-acetylpiperazin-1-yl)pyridin-2-yl)guanidine trifluoroacetate (524 mg, 2.00 mmol) and (L)-3-(dimethylamino)-1-(2-isopropyl-4-methylthiazol-5-yl)prop-2-en-1-one (238 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM: MeOH=93:7) to give 16 as a yellow solid (360 mg, 42%). $^1$H NMR (DMSO-$d_6$) δ 1.41 (d, 6H, J 7), 2.13 (s, 1H), 2.9 (s, 3H), 3.11 (app m, 4H), 3.28 (m, 1H), 3.62 (t, 2H, J 5.0), 3.78 (t, 2H, J 5.0), 6.96 (d, 1H, J 5.5), 7.35 (dd, 1H, J 9.5 & 3.0), 8.14 (d, 1H, J 2.5), 8.33 (d, 1H, J 9.5), 8.55 (d, 1H, J 5.0), 9.24 (s, 1H). HRMS (ESI): m/z 438.2088 [M+H]$^+$; calcd. for $C_{22}H_{28}N_7OS^+$ [M+H]$^+$ 438.2071. Anal. RP-HPLC Method A: $t_R$ 10.50 min, purity>98%; Method B: $t_R$ 8.45 min, purity>98%.

4-(2-Isopropyl-4-methylthiazol-5-yl)-N-(5-morpholinopyridin-2-yl)pyrimidin-2-amine (17)

To a mixture of crude 1-(5-morpholinopyridin-2-yl)guanidine trifluoroacetate (331.7 mg, 1.50 mmol) and (E)-3-(dimethylamino)-1-(2-isopropyl-4-methylthiazol-5-yl)prop-2-en-1-one (238 mg, 1.00 mmol) in 2-methoxy ethanol (3 mL) was added NaOH (60.0 mg, 1.50 mmol). The reaction mixture was heated at 180° C. under microwave irradiation for 1 h, cooled to room temperature and concentrated under reduced pressure. The residue was purified by chromatography (silica gel, DCM ramping to DCM:MeOH=97:3) to give 17 as a white solid (238 mg, 60%). $^1$H NMR ($CDCl_3$) δ 1.43 (d, 6H, J 7.0), 2.71 (s, 3H), 3.14 (t, 4H, J 5.0), 3.32 (m, 1H), 3.89 (t, 4H, J 5.0), 6.97 (d, 1H, J 5.0), 7.35 (dd, 1H, J 9.0 & 3.0), 8.09 (d, 1H, J 3.0), 8.10 (s, 1H), 8.31 (d, 1H, J 9), 8.46 (d, 1H, J 5.0). HRMS (ESI): m/z 397.1797 [M+H]$^+$; calcd. for $C_{20}H_{25}N_6OS^+$ [M+H]$^+$ 397.1805. Anal. RP-HPLC Method A: $t_R$ 10.97 min, purity>99%; Method B: $t_R$ 8.68 min, purity 100%.

N-(5-((4-Ethylpiperazin-1-yl)methyl)pyridin-2-yl)-4-(2-isopropyl-4-methylthiazol-5-yl)pyrimidin-2-amine (18)

To a mixture of 1-((6-bromopyridin-3-yl)methyl)-4-ethylpiperazine (341 mg, 1.20 mmol) and 4-(2-isopropyl-4-methylthiazol-5-yl)pyrimidin-2-amine (234.3 mg, 1.00 mmol) in dioxane (3 mL) were added $Pd_2dba_3$ (45.8 mg, 0.05 mmol), xantphose (57.9 mg, 0.1 mmol) and t-BuONa (144.2 mg, 1.50 mmol). The reaction mixture was heated at 150° C. under microwave irradiation for 1 h, cooled to room temperature and concentrated under reduced pressure. The residue was purified by chromatography (silica gel, DCM ramping to DCM:MeOH=98:2) to give 18 as a white solid (210 mg, 48%). $^1$H NMR (DMSO-$d_6$) δ 0.97 (t, 3H, J 7.5), 1.36 (d, 6H, J 7.0), 2.28 (q, 2H, J 7.5), 2.36 (s br, 8H), 2.67 (s, 3H), 3.24-3.30 (m, 1H), 3.42 (s, 1H), 7.17 (d, 1H, J 5.5), 7.70 (dd, 1H, J 8.5 & 2.0), 8.20 (d, 1H, J 2.0), 8.22 (d, 1H, J 8.5), 8.58 (d, 2H, J 5.5), 9.92 (s, 1H). HRMS (ESI): m/z 438.2435 [M+H]$^+$; calcd. for $C_{23}H_{32}N_7S^+$ [M+H]$^+$ 438.2434. Anal. RP-HPLC Method A: $t_R$ 9.43 min, purity>97%; Method B: $t_R$ 8.66 min, purity>98%.

4-(2-Methoxy-4-methylthi azol-5-yl)-N-(5-(4-methylpiperazin-1-yl)pyridin-2-yl)pyrimidin-2-amine (19)

To a mixture of crude 1-(5-(4-methylpiperazin-1-yl)pyridine-2-yl)guanidine trifluoroacetate (374 mg, 1.60 mmol) and (E)-3-(dimethylamino)-1-(2-methoxy-4-methylthiazol-5-yl)prop-2-en-1-one (183 mg, 0.80 mmol) in 2-methoxy ethanol (3 mL) was added NaOH (64.0 mg, 1.60 mmol). The reaction mixture was heated at 180° C. under microwave irradiation for 1 h, cooled to room temperature and concentrated under reduced pressure. The residue was purified by chromatography (silica gel, DCM ramping to DCM: MeOH=94:6) to give 19 as a yellow solid (52 mg, 13%). m.p. 190-192° C. $^1$H NMR ($CDCl_3$) 2.37 (s, 3H), 2.58 (s, 3H), 2.60 (t, 4H, J 5.0), 3.19 (t, 4H, J 5.0), 3.37 (s, 3H), 6.73 (d, 1H, J 5.0), 7.34 (dd, 1H, J 9.0 & 3.0), 7.97 (s, 1H), 8.01 (d, 1H, J 3.0), 8.21 (d, 1H, J 9.0), 9.40 (d, 1H, J 5.0). HRMS (ESI): m/z 398.1779 [M+H]$^+$; calcd. for $C_{19}H_{24}N_7OS^+$ [M+H]$^+$ 398.1758. Anal. RP-HPLC Method A: $t_R$ 8.36 min, purity>97%; Method B: $t_R$ 3.59 min, purity>99%.

4-(4-Methyl-2-(methylthio)thiazol-5-yl)-N-(5-(piperazin-1-yl)pyridin-2-yl)pyrimidin-2-amine (20)

To a suspension of 1-(4-(6-((4-(4-Methyl-2-(methylthio) thiazol-5-yl)pyrimidin-2-yl)amino)pyridin-3-yl)piperazin-1-yl)ethan-1-one (100 mg, 0.23 mmol) in methanol HCl (32%, 3 mL) was added and reflexed overnight. The reaction mixture was concentrated and purified by chromatography (silica gel, DCM ramping to DCM:MeOH: $NH_4OH$)=90:

10:1) to give 20 as a yellow solid (77 mg, 85%). $^1$H NMR (DMSO-$d_6$) δ 2.64 (s, 3H), 2.74 (s, 3H), 3.23 (t, 2H, J 5.5), 3.36 (app s, 4H), 7.12 (d, 1H, J 5.5), 7.54 (dd, 1H, J 9.0 & 3.0), 8.06 (d, 1H, J 3.0), 8.08 (d, 1H, J 9.0), 8.53 (s, 1H, J 5.5), 8.82 (s, 1H), 9.69 (s, 1H). HRMS (ESI): m/z 400.1390 [M+H]$^+$; calcd. for $C_{18}H_{22}N_7S_2^+$ [M+H]$^+$ 400.1373 Anal. RP-HPLC Method A: $t_R$ 8.85 min, purity>98%, Method B: $t_R$ 7.44 min, purity>99%.

4-(4-Methyl-2-(methylthio)thiazol-5-yl)-N-(5-(4-methylpiperazin-1-yl)pyridin-2-yl)pyrimidin-2-amine (21)

To a mixture of crude 1-(5-(4-methylpiperazin-1-yl)pyridine-2-yl)guanidine trifluoroacetate (468 mg, 2.00 mmol) and (E)-3-(dimethylamino)-1-(4-methyl-2-(methylthio)thiazol-5-yl)prop-2-en-1-one (242 mg, 1.00 mmol) in acetonitrile (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM: MeOH=94:6) to give 21 as a yellow solid (200 mg, 48%). m.p. 206-207° C. $^1$H NMR ($CDCl_3$) 2.37 (s, 3H), 2.61 (t, 4H, J 5.0), 2.69 (s, 3H), 2.73 (s, 3H), 3.19 (t, 4H, J 5.0), 6.93 (d, 1H, J 5.0), 7.36 (dd, 1H, J 9.0 & 3.0), 8.05 (d, 1H, J 3.0), 8.20 (s, 1H), 8.24 (d, 1H, J 9.0), 8.46 (d, 1H, J 5.0). HRMS (ESI): m/z 414.1552 [M+H]$^+$; calcd. for $C_{19}H_{24}N_7S_2^+$ [M+H]$^+$ 414.1529. Anal. RP-HPLC Method A: $t_R$ 9.36 min, purity>99%; Method B: $t_R$ 7.83 min, purity>99%.

1-(4-(6-((4-(4-Methyl-2-(methylthio)thiazol-5-yl) pyrimidin-2-yl)amino)pyridin-3-yl)piperazin-1-yl) ethan-1-one (22)

To a mixture of crude to a mixture of crude 1-(5-(4-acetylpiperazin-1-yl)pyridin-2-yl)guanidine trifluoroacetate (524 mg, 2.00 mmol) (468 mg, 2.00 mmol) and (E)-3-(dimethylamino)-1-(4-methyl-2-(methylthio)thiazol-5-yl) prop-2-en-1-one (242 mg, 1.00 mmol) in acetonitrile (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH=95:5) to give 22 as a yellow solid (141 mg, 32%). $^1$H NMR ($CDCl_3$) δ 2.15 (s, 3H), 2.69 (s, 3H), 2.73 (s, 3H), 3.13 (app m, 4H), 3.64 (t, 2H, J 5.0), 3.80 (t, 2H, J 5.0), 6.95 (d, 1H, J 5.5), 7.37 (dd, 1H, J 9.0 & 3.0), 8.08 (d, 1H, J 3.0), 8.29 (d, 1H, J 9.0), 8.49 (s, 1H, J 5.0), 8.53 (s, 1H). HRMS (ESI): m/z 442.1478 [M+H]$^+$; calcd. for $C_{20}H_{24}N_7OS_2^+$ [M+H]$^+$ 442.1486 Anal. RP-HPLC Method A: $t_R$ 8.23 min, purity>97%, Method B: $t_R$ 2.81 min, purity 100%.

4-(2-(Isopropylthio)-4-methylthiazol-5-yl)-N-(5-(piperazin-1-yl)pyridin-2-yl)pyrimidin-2-amine (23)

To a suspension of 1-(4-(6-((4-(2-(isopropylthio)-4-methylthiazol-5-yl)pyrimidin-2-yl)amino)pyridin-3-yl)piperazin-1-yl)ethan-1-one (100 mg, 0.21 mmol) in methanol HCl (32%, 3 mL) was added and reflexed overnight. The reaction mixture was concentrated and purified by chromatography (silica gel, DCM ramping to DCM:MeOH: $NH_4OH$)=90:10:1) to give 23 as a yellow solid (82 mg, 90%). $^1$H NMR ($CDCl_3$) 1.47 (s, 3H), 1.48 (s, 3H), 2. 7 (s, 3H), 3.06 (t, 4H, J 4.5), 3.13 (t, 4H, J 5.0), 3.89 (m, 1H), 6.94 (d, 1H, J 5.0), 7.36 (dd, 1H, J 9.0 & 3.0), 8.03 (d, 1H, J 3.0), 8.04 (s, 1H), 8.25 (d, 1H, J 9.0) 8.46 (d, 1H, J 5.0). HRMS (ESI): m/z 428.1696 [1M+H]$^+$; calcd. for $C_{20}H_{26}N_7S_2^+$ [M+H]$^+$ 428.1686. Anal. RP-HPLC Method A: $t_R$ 9.86 min, purity>93%; Method B: $t_R$ 7.96 min, purity>96%.

4-(2-(Isopropylthio)-4-methylthiazol-5-yl)-N-(5-(4-methylpiperazin-1-yl)pyridin-2-yl)pyrimidin-2-amine (24)

To a mixture of crude 1-(5-(4-methylpiperazin-1-yl)pyridine-2-yl)guanidine trifluoroacetate (468 mg, 2.0 mmol) and (E)-3-(dimethylamino)-1-(2-(isopropylthio)-4-methylthiazol-5-yl)prop-2-en-1-one (270 mg, 1.00 mmol) in acetonitrile (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM: MeOH=90:10) to give 24 as a yellow solid (97 mg, 22%). m.p. 198-200° C. $^1$H NMR ($CDCl_3$) 1.46 (s, 3H), 1.47 (s, 3H), 2.37 (s, 3H), 2.61 (t, 4H, J 5.0), 2.69 (s, 3H), 3.19 (t, 4H, J 5.0), 3.88 (m, 1H), 6.93 (d, 1H, J 5.0), 7.36 (dd, 1H, J 9.0 & 3.0), 8.08 (s, 1H), 8.25 (d, 1H, J 9.0), 8.49 (d, 1H, J 5.0), 8.62 (s, 1H). HRMS (ESI): m/z 442.1865 [M+H]$^+$; calcd. for $C_{21}H_{28}N_7S_2^+$ [M+H]$^+$ 442.1842. Anal. RP-HPLC Method A: $t_R$ 10.34 min, purity>96%; Method B: $t_R$ 8.36 min, purity>98%.

1-(4-(6-(4-(2-(Isopropylthio)-4-methylthiazol-5-yl) pyrimidin-2-yl)amino)pyridin-3-yl)piperazin-1-yl) ethan-1-one (25)

To a mixture of crude 1-(5-(4-acetylpiperazin-1-yl)pyridin-2-yl)guanidine trifluoroacetate (524 mg, 2.00 mmol) and (E)-3-(dimethylamino)-1-(2-(isopropylthio)-4-methylthiazol-5-yl)prop-2-en-1-one (270 mg, 1.00 mmol) in acetonitrile (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM: MeOH=94:6) to give 25 as a yellow solid (193 mg, 41%). $^1$H NMR ($CDCl_3$) δ 1.47 (s, 3H), 1.48 (s, 3H), 2.15 (s, 3H), 2.70 (s, 3H), 3.13 (app m, 4H), 3.65 (t, 2H, J 5.0), 3.80 (t, 2H, J 5.0), 3.89 (m, 1H), 6.95 (d, 1H, J 5.5), 7.37 (dd, 1H, J 9.0 & 3.0), 8.05 (d, 1H, J 3.0), 8.29 (app br d, 2H), 8.48 (d, 1H, J 5.0). HRMS (ESI): m/z 470.1787 [M+H]$^+$; calcd. for $C_{22}H_{28}N_7OS_2^+$ [M+H]$^+$ 470.1791 Anal. RP-HPLC Method A: $t_R$ 8.23 min, purity>93%, Method B: $t_R$ 2.81 min, purity>95%.

N,4-Dimethyl-5-(2-((5-piperazin-1-yl)pyridine-2-yl) amino)pyrimidin-4-yl)thiazol-2-amine (26)

To a solution of crude 1-(5-(piperazin-1-yl)pyridin-2-yl) guanidine trifluoroacetate (264 mg, 1.20 mmol) in 2-methoxyethanol (4 mL) were added (E)-3-(dimethylamino)-1-(4-methyl-2-(methylamino)thiazol-5-yl)prop-2-en-1-one (225 mg, 1.00 mmol) and NaOH (82.0 mg, 2.40 mmol). The reaction mixture was heated at 180° C. for 90 min under microwave irradiation, cooled down to room temperature, and then concentrated under reduced pressure. The residue was purified by chromatography (silica gel, chloroform ramping to chloroform:MeOH=91:9 with consecutive addition of 32% aqueous ammonia, up to 10%). The solid was washed with DCM and MeOH, then filtered to give 26 as a pale yellow solid (94.0 mg, 24%). $^1$H NMR (DMSO-$d_6$) δ 2.47 (s, 3H), 2.83 (t, 4H, J 5.0), 2.87 (d, 3H, J 4.5), 3.01 (t, 4H, J 5.0), 6.91 (d, 1H, J 5.5), 7.38 (dd, 1H, J 9.0 & 3.0), 7.97 (d, 1H, J 3.0), 8.04-8.07 (m, 2H), 8.33 (d, 1H, J 4.0), 9.25 (s, 1H). MS (ESI): m/z 383.1674 $[M+H]^+$; calcd. for $C_{18}H_{23}N_8S^+[M+H]^+$ 383.1761. Anal. RP-HPLC Method A: $t_R$ 8.37 min, purity>99%; Method B: $t_R$ 7.10 min, purity>99%.

4-(4-Methyl-2-(methylamino)thiazol-5-yl)-2-((5-(piperazin-1-yl)pyridin-2-yl)amino)pyrimidine-5-carbonitrile (27)

To a solution of crude 1-(5-(piperazin-1-yl)pyridin-2-yl) guanidine trifluoroacetate (264 mg, 1.20 mmol) in 2-methoxyethanol (4 mL) were added tert-butyl (E)-(5-(2-cyano-3-(dimethylamino)acryloyl)-4-methylthiazol-2-yl) (methyl)carbamate (350 mg, 1.00 mmol) and NaOH (82.0 mg, 2.40 mmol). The reaction mixture was heated at 180° C. for 90 min under microwave irradiation, cooled down to room temperature, and then concentrated under reduced pressure. The residue was purified by chromatography (silica gel, chloroform ramping to chloroform:MeOH=91:9 with consecutive addition of 32% aqueous ammonia, up to 3 mL). The solid was washed with DCM and MeOH, and then filtered to give 27 as a pale yellow solid (131 mg, 32%). $^1$H NMR (DMSO-$d_6$) δ 2.41 (s, 3H), 2.88-2.89 (m, 7H), 3.07 (t, 4H, J 5.5), 7.41 (dd, 1H, J 9.0 & 3.0), 7.88 (d, 1H, J 9.0), 8.03 (d, 1H, J 3.0), 8.26 (q, 1H, J 4.5), 8.75 (s, 1H), 10.30 (s, 1H). MS (ESI): m/z 408.1660 $[M+H]^+$; calcd. for $C_{19}H_{22}N_9S^+$ $[M+H]^+$ 408.1713.

5-(5-Fluoro-2-((5-(piperazin-1-yl)pyridin-2-yl) amino)pyrimidin-4-yl)-N,4-dimethylthiazol-2-amine (28)

To a suspension of 1-(4-(6-((5-fluoro-4-(4-methyl-2-(methylamino)thiazol-5-yl)pyrimidin-2-yl)amino)pyridin-3-yl)piperazin-1-yl)ethan-1-one (200 mg, 0.45 mmol) in methanol HCl (32%, 3 mL) was added and reflexed overnight. The reaction mixture was concentrated and purified by chromatography (silica gel, DCM ramping to EtOAc: MeOH:$NH_4OH$)=90:10:1) to give 28 as a yellow solid (140 mg, 77%). $^1$H NMR (DMSO-$d_6$) δ 2.47 (d, 3H, J 2.0), 2.83 (t, 4H, J 4.5), 2.87 (d, 3H, J 4.5), 3.00 (t, 4H, J 5.0), 7.37 (dd, 1H, J 9.0 & 2.5), 7.94 (d, 1H, J 9.0), 7.96 (d, 1H, J 3.0), 8.11 (app d, 1H, J 4.5), 8.41 (d, 1H, J 3.0), 9.48 (s, 1H). HRMS (ESI): m/z 401.1678 $[M+H]^+$; calcd. for $C_{18}H_{22}FN_8S^+$ $[M+H]^+$ 401.1667. Anal. RP-HPLC Method A: $t_R$ 8.14 min, purity>95%; Method B: $t_R$ 2.80 min, purity 100%.

N,4-Dimethyl-5-(2-((5-(4-methylpiperazin-1-yl) pyridine-2-yl)amino)pyridine-4-yl)thiazol-2-amine (29)

To a solution of crude 1-(5-(4-methylpiperazin-1-yl)pyridine-2-yl)guanidine trifluoroacetate (200 mg, 0.854 mmol) in 2-methoxyethanol (4.0 mL) was added (E)-3-(dimethylamino)-1-(4-methyl-2-(methylamino)thiazol-5-yl)prop-2-en-1-one and NaOH (58.1 mg, 1.71 mmol). The reaction mixture was heated at 160° C. for 30 min, cooled down to room temperature and concentrated under reduced pressure. The residue was purified by chromatography (silica gel, DCM ramping to DCM:MeOH=91:9) and washed with DCM and MeOH to give 29 as a pale yellow solid (91.0 mg, 27%,). $^1$H NMR (DMSO-$d_6$) δ 2.22 (s, 3H), 2.45-2.47 (m, 7H), 2.87 (d, 3H, J 4.5), 3.11 (t, 4H, J 5.0), 6.91 (d, 1H, J 5.5), 7.40 (dd, 1H, J 9.0 & 3.0), 7.99 (d, 1H, J 3.0), 8.06-8.08 (m, 2H), 8.33 (d, 1H, J 5.5), 9.24 (s, 1H). MS (ESI): m/z 397.1958 $[M+H]^+$; calcd. for $C_{20}H_{25}N_7S^+$ $[M+H]^+$ 397.1917.Anal. RP-HPLC Method A: $t_R$ 8.27 min, purity>90%; Method B: $t_R$ 7.09 min, purity>94%.

4-(4-Methyl-2-(methylamino)thiazol-5-yl)-2-((5-(4-methylpiperazin-1-yl)pyridin-2-yl)amino)pyrimidine-5-carbonitrile (30)

To a solution of crude 1-(5-(4-methylpiperazin-1-yl)pyridine-2-yl)guanidine trifluoroacetate (468 mg, 2.00 mmol) in 2-methoxyethanol (4 mL) were added tert-butyl (E)-(5-(2-cyano-3-(dimethylamino)acryloyl)-4-methylthiazol-2-yl) (methyl)carbamate (350 mg, 1.00 mmol) and NaOH (136 mg, 4.00 mmol). The reaction mixture was heated at 180° C. for 60 min, cooled down to room temperature and concentrated under reduced pressure. The residue was purified by chromatography (silica gel, DCM ramping to DCM: MeOH=91:9) and washed with DCM and MeOH, to give 30 as a pale yellow solid (363 mg, 43%). $^1$H NMR (DMSO-$d_6$) δ 2.43 (s, 3H), 2.74 (s, 3H), 2.89 (d, 4H, J 5.0),3.17 (d, 4H, J 5.0),7.50 (dd, 1H, J 9.0 & 3.0), 7.93 (d, 1H, J 9.0), 8.11 (d, 1H, J 3.0), 8.28 (d, 1H, J 4.5), 8.77 (s, 1H), 10.39 (s, 1H). MS (ESI): m/z 422.1808 $[M+H]^+$; calcd. for $C_{20}H_{24}N_9S^+$ $[M+H]^+$ 422.1870.Anal. RP-HPLC Method A: $t_R$ 8.72 min, purity>99%; Method B: $t_R$ 7.36 min, purity>99%.

5-(5-Fluoro-2-((5-(4-methylpiperazin-1-yl)pyridin-2-yl)amino)pyrimidin-4-yl)-N,4-dimethylthiazol-2-amine (31)

To a solution of crude 1-(5-(4-methylpiperazin-1-yl)pyridine-2-yl)guanidine trifluoroacetate (468 mg, 2.00 mmol) in 2-methoxyethanol (3 mL) were added (E)-3-(dimethylamino)-2-fluoro-1-(4-methyl-2-(methylamino)thiazol-5-yl) prop-2-en-1-one (243 mg, 1.00 mmol) and NaOH (80.0 mg, 2.00 mmol). The reaction mixture was heated at 180° C. for 60 min, cooled down to room temperature and concentrated under reduced pressure. The residue was purified by chromatography (silica gel, DCM ramping to DCM:MeOH: $NH_4OH$=92:8:1) and washed with DCM and MeOH, to give 31 as a reddish brown solid (124 mg, 30%).$^1$H NMR (DMSO-$d_6$) δ 2.22 (s, 3H), 2.45 (t, 4H, J 4.5), 2.47 (app d, 3H, J 2), 2.87 (d, 3H, J 5), 3.10 (t, 4H, J 5), 7.40 (dd, 1H, J 9.0 & 3.0), 7.95 (d, 1H, J 9.0), 7.97 (d, 1H, J 3.0), 8.11 (q, 1H, J 4.5), 8.42 (d, 1H, J 3.5), 9.53 (s, 1H). HRMS (ESI): m/z 415.1846 $[M+H]^+$; calcd. for $C_{19}H_{24}FN_8S^+$ $[M+H]^+$ 415.1823. Anal. RP-HPLC Method A: $t_R$ 8.09 min, purity>95%; Method B: $t_R$ 2.83 min, purity 99%.

5-(2-((5-(4-Ethylpiperazin-1-yl)pyridin-2-yl)amino)-5-fluoropyrimidin-4-yl)-N,4-dimethylthiazol-2-amine (32)

To a solution of crude 1-(5-(4-ethylpiperazin-1-yl)pyridin-2-yl)guanidine trifluoroacetate (496.6 mg, 2.00 mmol) in 2-methoxyethanol (3 mL) were added (E)-3-(dimethylamino)-2-fluoro-1-(4-methyl-2-(methylamino)thiazol-5-yl) prop-2-en-1-one (243 mg, 1.00 mmol) and NaOH (80.0 mg, 2.00 mmol). The reaction mixture was heated at 180° C. for 60 min, cooled down to room temperature and concentrated under reduced pressure. The residue was purified by chromatography (silica gel, DCM ramping to DCM:MeOH=90: 10) to give 32 as a yellow solid (146 mg, 34%). $^1$H NMR (DMSO-$d_6$) δ 1.03 (t, 3H, J 7.0), 2.36 (q, 3H, J 7.0), 2.48 (app d, 3H, J 2.0), 2.50 (br, 4H), 2.87 (d, 3H, J 5.0), 3.10 (t, 4H, J 5.0), 7.39 (dd, 1H, J 9.0 & 3.0), 7.96 (d, 1H, J 9.0), 7.99 (d, 1H, J 3.0), 8.13 (q, 1H, J 4.5), 8.43 (d, 1H, J 3.5), 9.55 (s, 1H). HRMS (ESI): m/z 429.1982 $[M+H]^+$; calcd. for $C_{20}H_{26}FN_8S^+$ $[M+H]^+$ 429.1980. Anal. RP-HPLC Method A: $t_R$ 8.30 min, purity 100%; Method B: $t_R$ 2.80 min, purity 100%.

1-(4-(6-((4-(4-Methyl-2-(methylamino)thiazol-5-yl) pyrimidin-2-yl)amino)pyridin-3-yl)piperazin-1-yl) ethan-1-one (33)

To a solution of crude 1-(5-(4-acetylpiperazin-1-yl)pyridin-2-yl)guanidine trifluoroacetate (525 mg, 2.00 mmol) in 2-methoxyethanol (3 mL) were added (E)-3-(dimethylamino)-1-(4-methyl-2-(methylamino)thiazol-5-yl)prop-2-en-1-one (225 mg, 1.00 mmol) and NaOH (80.0 mg, 2.00 mmol). The reaction mixture was heated at 180° C. for 1 h under microwave irradiation, cooled down to room temperature, and then concentrated under reduced pressure. The residue was purified by chromatography (silica gel, DCM ramping to DCM:MeOH=90:10+0.5 ml of 32% ammonia) to give 33 as a yellow solid (100 mg, 24%). $^1$H NMR ($CDCl_3$) δ 2.15 (s, 3H), 2.56 (s, 3H), 3.05 (s, 3H), 3.10 (t, 2H, J 4.5), 3.14 (t, 2H, J 4.5), 3.64 (t, 2H, J 4.5), 3.79 (t, 2H, J 4.5), 5.73 (s, 1H), 6.88 (d, 1H, J 5.5), 7.35 (dd, 1H, J 9.0 & 2.5), 7.89 (s, 1H), 8.01 (d, 1H, J 2.0), 8.31 (d, 1H, J 9.0), 8.35 (d, 1H, J 5.0). HRMS (ESI): m/z 425.1878 $[M+H]^+$; calcd. for $C_{20}H_{25}N_8OS^+$ $[M+H]^+$ 425.1867. Anal. RP-HPLC Method A: $t_R$ 9.92 min, purity 100%; Method B: $t_R$ 8.00 min, purity 100%.

2-((5-(4-acetylpiperazin-1-yl)pyridin-2-yl)amino)-4-(4-methyl-2-(methylamino)thiazol-5-yl)pyrimidine-5-carbonitrile (34)

To a solution of crude 1-(5-(4-acetylpiperazin-1-yl)pyridin-2-yl)guanidine trifluoroacetate (315 mg, 1.20 mmol) in 2-methoxyethanol (4 mL) were added tort-butyl (E)-(5-(2-cyano-3-(dimethylamino)acryloyl)-4-methylthiazol-2-yl) (methyl)carbamate (350 mg, 1.00 mmol) and NaOH (82.0 mg, 2.40 mmol). The reaction mixture was heated at 180° C. for 90 min under microwave irradiation, cooled down to room temperature, and then concentrated under reduced pressure. The residue was purified by chromatography (silica gel, DCM ramping to DCM:MeOH=90:10 with consecutive addition of 32% aqueous ammonia, up to 3%). The solid was washed with DCM and McOH, then filtered to give 34 as a pale yellow solid (157 mg, 35%). $^1$H NMR (DMSO-$d_6$) δ 2.04 (s, 3H), 2.40 (s, 3H), 2.87 (s, 3H), 3.10 (t, 2H, J 5.0), 3.16 (t, 2H, J 5.0), 3.58 (t, 4H, J 5.0), 7.46 (dd, 1H, J 9.5 & 3.0), 7.90 (d, 1H, J 9.0), 8.06 (d, 1H, J 3.0), 8.26 (q, 1H, J 3.0), 8.75 (s, 1H), 10.33 (s, 1H). HRMS (ESI): m/z 450.1844 $[M+H]^+$; calcd. for $C_{21}H_{24}N_9OS^+$ $[M+H]^+$ 450.1819. Anal. RP-HPLC Method A: $t_R$ 10.34 min, purity>97%; Method B: $t_R$ 8.769 min, purity>98%.

1-(4-(6-((5-Fluoro-4-(4-methyl-2-(methylamino) thiazol-5-yl)pyrimidin-2-yl)amino)pyridin-3-yl)piperazin-1-yl)ethan-1-one (35)

To a solution of crude 1-(5-(4-acetylpiperazin-1-yl)pyridin-2-yl)guanidine trifluoroacetate (1.08 g, 2.06 mmol) in 2-methoxyethanol (6 mL) were added (E)-3-(dimethylamino)-2-fluoro-1-(4-methyl-2-(methylamino)thiazol-5-yl) prop-2-en-1-one (500 mg, 2.06 mmol) and NaOH (164.4 mg, 4.11 mmol). The reaction mixture was heated at 180° C. for 150 min under microwave irradiation, cooled down to room temperature, and then concentrated under reduced pressure. The residue was purified by chromatography (silica gel, DCM ramping to DCM:MeOH=90:10 with consecutive addition of 32% aqueous ammonia, up to 1%). The solid was washed with DCM and MeOH, then filtered to give 35 as a reddish brown solid (400 mg, 44%). $^1$H NMR (DMSO-$d_6$) δ 2.04 (s, 3H,), 2.47 (d, 3H, J 2.5), 2.87 (d, 3H, J 4.5), 3.05 (t, 2H, J 5.0), 3.11 (t, 2H, J 5.0), 3.58 (app q, 4H, J 6.0), 7.43 (dd, 1H, J 9.0 & 3.0), 7.98 (d, 1H, J 9.0), 8.02 (d, 1H, J 3.0), 8.12 (q, 1H, J 4.5), 8.43 (d, 1H, J 3.5), 9.59 (s, 1H). HRMS (ESI) m/z 443.1800 $[M+H]^+$; calcd. for $C_{20}H_{24}FN_8OS^+$ $[M+H]^+$ 443.1772. Anal. RP-HPLC Method A: $t_R$ 9.75 min, purity>95%; Method B: $t_R$ 7.77 min, purity>95%.

N,4-dimethyl-5-(2-((5-morpholinopyridin-2-yl) amino)pyrimidin-4-yl)thiazole-2-amine (36)

To a solution of crude 1-(5-(4-aminopiperidin-1-yl)pyridin-2-yl)guanidine trifluoroacetate (266 mg, 1.20 mmol) in 2-methoxyethanol (4 mL) were added (E)-3-(dimethylamino)-1-(4-methyl-2-(methylamino)thiazol-5-yl)prop-2-en-1-one (225 mg, 1.00 mmol) and NaOH (82.0 mg, 2.40 mmol). The reaction mixture was heated at 180° C. for 90 min under microwave irradiation, cooled down to room temperature, and then concentrated under reduced pressure. The residue was purified by chromatography (silica gel, DCM ramping to DCM:MeOH=96:4). The solid was washed with DCM and MeOH, and then filtered to give 36 as a pale yellow solid (69.0 mg, 18%). $^1$H NMR, DMSO-$d_6$) δ 2.47 (s, 3H), 2.86 (d, 2H, J 5.0), 3.08 (t, 4H, J 5.0), 3.74 (t, 4H, J 5.0), 6.92 (d, 1H, J 5.0), 7.41 (dd, 1H, J 9.0 &3.0), 7.99 (d, 1H, J 3.0), 8.06 (q, 1H, J 5.0 & 4.5), 8.08 (d, 1H, J 9.0), 8.33 (d, 1H, J 5.0), 9.26 (s, 1H). MS (ESI): m/z 384.1674 $[M+H]^+$; calcd. for $C_{18}H_{21}N_7OS^+$ $[M+H]^+$ 384.1601.Anal. RP-HPLC Method A: $t_R$ 10.08 min, purity>99%; Method B: $t_R$ 7.98 min, purity>99%.

4-(4-Methyl-2-(methylamino)thiazol-5-yl)-2-((5-morpholinopyridin-2-yl)amino)pyrimidine-5-carbonitrile (37)

To a solution of crude 1-(5-(4-aminopiperidin-1-yl)pyridin-2-yl)guanidine trifluoroacetate (222 mg, 1.00 mmol) in 2-methoxyethanol (4 mL) were added tert-butyl (E)-(5-(2-cyano-3-(dimethylamino)acryloyl)-4-methylthiazol-2-yl) (methyl)carbamate (350 mg, 1.00 mmol) and NaOH (68.0 mg, 2.00 mmol). The reaction mixture was heated at 180° C. for 90 min under microwave irradiation, cooled down to room temperature, and then concentrated under reduced pressure. The residue was purified by chromatography (silica gel, DCM ramping to DCM:MeOH=97:3), washed with DCM and MeOH, then filtered to give 37 as a pale yellow solid (126 mg, 31%). $^1$H NMR (DMSO-$d_6$) δ 2.42 (s, 3H), 2.89 (d, 3H, J 4.5), 3.12 (t, 4H, J 5.0), 3.75 (t, 4H, J 5.0), 7.42 (dd, 1H, J 9.0 & 3.0), 7.93 (d, 1H, J 9.0), 8.04 (d, 1H, J 3.0), 8.23 (dd, 1H, J 9.0 & 4.5), 8.73 (s, 1H), 10.28 (s, 1H). HRMS (ESI): m/z 409.1549 $[M+H]^+$; calcd. for $C_{19}H_{20}N_8OS^+$ $[M+H]^+$ 409.1554.Anal. RP-HPLC Method A: $t_R$ 10.88 min, purity>98%; Method B: $t_R$ 8.60 min, purity>97%.

5-(5-Fluoro-2-((5-morpholinopyridin-2-yl)amino) pyrimidin-4-yl)-N,4-dimethylthiazol-2-amine (38)

To a solution of crude 1-(5-(4-aminopiperidin-1-yl)pyridin-2-yl)guanidine trifluoroacetate (332 mg, 1.5 mmol) in 2-methoxyethanol (4 mL) were added (E)-3-(dimethylamino)-2-fluoro-1-(4-methyl-2-(methylamino)thiazol-5-yl) prop-2-en-1-one (243 mg, 1.00 mmol) and NaOH (60.0 mg, 1.5 mmol). The reaction mixture was heated at 180° C. for 90 min under microwave irradiation, cooled down to room temperature, and then concentrated under reduced pressure. The residue was purified by chromatography (silica gel, DCM ramping to DCM:MeOH=94:6) to give 38 as a purple solid (138 mg, 34%). $^1$H NMR (DMSO-$d_6$) δ 2.48 (d, 3H, J 2.0), 2.87 (d, 3H, J 4.5), 3.08 (t, 4H, J 5), 3.75 (t, 4H, J 5.0), 7.39 (dd, 1H, J 9.0 & 3.0), 7.97 (d, 1H, J 9.0), 7.99 (d, 1H, J 3.0), 8.12 (q, 1H, J 4.5), 8.42 (d, 1H, J 3.5), 9.52 (s, 1H). HRMS (ESI): m/z 402.1524 [M+H]$^+$; calcd. for $C_{18}H_{21}FN_7OS^+$ [M+H]$^+$ 402.1507. Anal. RP-HPLC Method A: $t_R$ 9.95 min, purity 100%; Method B: $t_R$ 7.97 min, purity 100%.

5-(2-((5-(4-Benzylpiperazin-1-yl)pyridin-2-yl) amino)pyrimidin-4-yl)-N,4-dimethylthiazol-2-amine (39)

To a solution of crude 1-(5-(4-benzylpiperazin-1-yl)pyridin-2-yl)guanidine trifluoroacetate trifluoroacetate (640 mg, ≤0.999 mmol) in 2-methoxyethanol (3 mL) were added (E)-3-(Dimethylamino)-1-(4-methyl-2-(methylamino)thiazol-5-yl)prop-2-en-1-one (390 mg, 1.20 mmol) and NaOH (80.0 mg, 2.03 mmol). The reaction mixture was heated at 140° C. under microwave irradiation for 45 min, cooled down to room temperature and filtered. The solids were washed with MeOH (15 mL) and DCM (30 mL), and purified by chromatography (silica gel, DCM ramping to DCM:MeOH=95:5) to give 39 as a yellow solid (64.0 mg, 14%, an overall yield for two steps). m.p. 275-276° C. $^1$H NMR (DMSO-$d_6$) δ 2.46 (s, 3H), 2.52 (t, 4H, J 4.0), 2.86 (d, 3H, J 4.0), 3.12 (t, 4H, J 3.6), 3.53 (s, 2H), 6.91 (d, 1H, J 4.4), 7.24-7.28 (m, 1H), 7.33-7.36 (m, 4H), 7.38 (dd, 1H, J 7.2 & 2.4), 7.96 (d, 1H, J 2.4), 8.03 (q, 1H, J 4.0), 8.06 (d, 1H, J 7.6), 8.32 (d, 1H, J 4.4), 9.18 (s, 1H). HRMS (ESI): 473.2252 ([M+H]$^+$); calcd. for $C_{25}H_{29}N_8S^+$ ([M+H]$^+$) 473.2230. Anal. RP-HPLC Method A: $t_R$ 7.51 min, purity>99%; Method B: $t_R$ 6.26 min, purity>99%.

2-((5-(4-Benzylpiperazin-1-yl)pyridin-2-yl)amino)-4-(4-methyl-2-(methylamino)thiazol-5-yl)pyrimidine-5-carbonitrile (40)

To a solution of crude 1-(5-(4-benzylpiperazin-1-yl)pyridin-2-yl)guanidine trifluoroacetate (640 mg, ≤0.999 mmol) in 2-methoxyethanol (3 mL) were added teat-butyl (E)-(5-(2-cyano-3-(dimethylamino)acryloyl)-4-methylthiazol-2-yl) (methyl)carbamate (350 mg, 0.999 mmol) and NaOH (80.0 mg, 2.03 mmol). The reaction mixture was heated at 140° C. under microwave irradiation for 45 min, cooled down to room temperature and filtered. The solids were washed with MeOH (15 mL) and DCM (30 mL), and purified by chromatography (silica gel, DCM ramping to DCM:MeOH=95:5) to give 40 as a yellow solid (177 mg, 36%, an overall yield for two steps and calculated based on 6). m.p. 255-256° C. $^1$H NMR (DMSO-$d_6$) δ 2.40 (s, 3H), 2.51 (t, 4H, J 3.6), 2.87 (d, 3H, J 3.2), 3.14 (t, 4H, J 3.6), 3.51 (s, 2H), 7.23-7.28 (m, 1H), 7.32-7.35 (m, 4H), 7.40 (dd, 1H, J 7.2 & 2.4), 7.87 (d, 1H, J 7.2), 8.03 (d, 1H, J 2.4), 8.23 (q, 1H, J 3.2), 8.73 (s, 1H), 10.29 (s, 1H). HRMS (ESI): 498.2188 [M+H]$^+$; calcd. for $C_{26}H_{28}N_9S^+$ [M+H]$^+$ 498.2183. Anal. RP-HPLC Method A: $t_R$ 8.38 min, purity>95%; Method B: $t_R$ 6.75 min, purity>96%.

5-(2-((4-(4-Benzylpiperazin-1-yl)phenyl)amino) pyrimidin-4-yl)-N,4-dimethylthiazol-2-amine (41)

To a solution of crude 1-(4-(4-benzylpiperazin-1-yl)phenyl)guanidine trifluoroacetate (530 mg, ≤1.71 mmol) in 2-methoxyethanol (3 mL) were added (E)-3-(dimethylamino)-1-(4-methyl-2-(methylamino)thiazol-5-yl)prop-2-en-1-one (200 mg, 0.888 mmol) and NaOH (73.0 mg, 1.82 mmol). The reaction mixture was heated at 160° C. under microwave irradiation for 30 min, cooled down to room temperature and concentrated under reduced pressure. The residue was purified by chromatography (silica gel, DCM ramping to DCM:MeOH=95:5) to give 41 as a yellow solid (60.0 mg, 14%). m.p. 212-213° C.

$^1$H NMR (DMSO-$d_6$) δ 2.44 (s, 3H), 2.50 (t, 4H, J 4.0), 2.85 (d, 3H, J 3.6), 3.05 (t, 4H, J 4.0), 3.51 (s, 2H), 6.81 (d, 1H, J 4.4), 6.85 (d, 2H, J 7.6), 7.23-7.29 (m, 1H), 7.31-7.35 (m, 4H), 7.57 (d, 2H, J 7.2), 7.98 (q, 1H, J 4.0), 8.26 (d, 1H, J 4.4), 9.13 (s, 1H). HRMS (ESI): 472.2295 [M+H]$^+$; calcd. for $C_{26}H_{30}N_7S^+$ [M+H]$^+$ 472.2278. Anal. RP-HPLC Method A: $t_R$ 8.11 min, purity>99%; Method B: $t_R$ 6.62 min, purity>99%.

2-((4-(4-Benzylpiperazin-1-yl)phenyl)amino)-4-(4-methyl-2-(methylamino)thiazol-5-yl)pyrimidine-5-carbonitrile (42)

To a solution of crude 1-(4-(4-benzylpiperazin-1-yl)phenyl)guanidine trifluoroacetate (353 mg, ≤1.14 mmol) in 2-methoxyethanol (3 mL) were added tort-butyl (E)-(5-(2-cyano-3-(dimethylamino)acryloyl)-4-methylthiazol-2-yl) (methyl)carbamate (200 mg, 0.571 mmol) and NaOH (45.7 mg, 1.14 mmol). The reaction mixture was heated at 160° C. under microwave irradiation for 30 min, cooled down to room temperature and concentrated under reduced pressure. The residue was purified by chromatography (silica gel, DCM ramping to DCM:EtOAc=1:3) and recrystallized with DCM and MeOH to give 42 as a yellow solid (80.0 mg, 28%). m.p. 220-221° C. $^1$H NMR (DMSO-$d_6$) δ 2.34 (s, 3H), 2.50 (t, 4H, J 4.0), 2.86 (d, 3H, J 3.6), 3.08 (t, 4H, J 4.0), 3.51 (s, 2H), 6.89 (d, 2H, J 7.2), 7.23-7.29 (m, 1H), 7.31-7.35 (m, 4H), 7.48 (d, 2H, J 6.4), 8.17 (q, 1H, J 3.6), 8.67 (d, 1H, J 4.0), 10.03 (s, 1H). HRMS (ESI): 497.2206 [M+H]$^+$; calcd. for $C_{27}H_{29}N_8S^+$ [M+H]$^+$ 1497.2230. Anal. RP-HPLC Method A: $t_R$ 8.36 min, purity>96%; Method B: $t_R$ 10.18 min, purity>95%.

N,N,4-Trimethyl-5-(2-((5-(piperazin-1-yl)pyridin-2-yl)amino)pyrimidin-4-yl)thiazol-2-amine (43)

To a suspension of 1-(4-(6-((4-(2-(Dimethylamino)-4-methylthiazol-5-yl)pyrimidin-2-yl)amino)pyridin-3-yl)piperazin-1-yl)ethan-1-one (100 mg, 0.23 mmol) in methanol HCl (32%, 3 mL) was added and reflexed overnight. The reaction mixture was concentrated and purified by chromatography (silica gel, DCM ramping to EtOAc:MeOH:$NH_4OH$)=90:10:1) to give 43 as a yellow solid (83 mg, 92%). m.p. 210-211° C. $^1$H NMR (DMSO-$d_6$) δ 1.74 (br, 1H), 2.57 (s, 3H), 3.06 (t, 4H, J 5.5), 3.11 (t, 4H, J 3.5), 3.18 (s, 6$H_2$), 6.84 (d, 1H, J 5.5), 7.33 (dd, 1H, J 9.0 & 3.0), 7.79 (s, 1H), 7.99 (d, 1H, J 3.0), 8.28 (d, 1H, J 9.5), 8.31 (d, 1H, J 5.5). HRMS (ESI): m/z 397.1925 [M+H]$^+$; calcd. for $C_{19}H_{25}N_8S^+$ [M+H]$^+$ 397.1917. Anal. RP-HPLC Method A: $t_R$ 8.39 min, purity>95%; Method B: $t_R$ 7.42 min, purity 100%.

5-(5-Fluoro-2-((5-(piperazin-1-yl)pyridin-2-yl)amino)pyrimidin-4-yl)-N,N,4-trimethylthiazol-2-amine (44)

To a suspension of 1-(4-(6-((4-(2-(dimethylamino)-4-methylthiazol-5-yl)-5-fluoropyrimidin-2-yl)amino)pyridin-3-yl)piperazin-1-yl)ethan-1-one (100 mg, 0.22 mmol) in methanol HCl (32%, 3 mL) was added and reflexed overnight. The reaction mixture was concentrated and purified by chromatography (silica gel, DCM ramping to DCM:MeOH:$NH_4OH$=90:10:1) to give 44 as a yellow solid (45.4 mg, 50%). $^1$H NMR ($CDCl_3$) δ 2.58 (d, 3H, J 2.0,), 3.05 (t, 4H, J 6.0), 3.09 (t, 4H, J 6.0), 3.17 (s, 6H), 7.30 (dd, 1H, J 9.0 & 3.0), 7.98 (br s, 1H), 8.00 (s, 1H), 8.19 (d, 1H, J 9.0), 8.23 (d, 1H, J 1.5). HRMS (ESI): m/z 415.1821 $[M+H]^+$; calcd. for $C_{19}H_{24}FN_8S^+$ $[M+H]^+$ 415.1823. Anal. RP-HPLC Method A: $t_R$ 9.00 min, purity>98%; Method B: $t_R$ 7.30 min, purity>99%.

N,N,4-trimethyl-5-(2-((5-(4-methylpiperazin-1-yl)pyridin-2-yl)amino)pyrimidin-4-yl)thiazol-2-amine (45)

To a solution of crude 1-(5-(4-methylpiperazin-1-yl)pyridine-2-yl)guanidine trifluoroacetate (468 mg, 2.00 mmol) in 2-methoxyethanol (3 mL) were added (E)-3-(dimethylamino)-1-(2-(dimethylamino)-4-methylthiazol-5-yl)prop-2-en-1-one (239 mg, 1.00 mmol) and NaOH (80.0 mg, 2.00 mmol). The reaction mixture was heated at 180° C. for 1 h under microwave irradiation, cooled down to room temperature, and then concentrated under reduced pressure. The residue was purified by chromatography (silica gel, DCM ramping to DCM:MeOH=90:10 with constant addition of 0.5 ml of 32% ammonia) to give 45 as a yellow solid (40.0 mg, 10%). $^1$H NMR ($CDCl_3$) δ 2.36 (s, 3H), 2.57 (s, 3H), 2.59 (t, 4H, J 5.0), 3.17 (br s, 10H), 6.84 (d, 1H, J 5.5), 7.33 (dd, 1H, J 9.0 & 3.0), 7.96 (s, 1H), 8.02 (d, 1H, J 3.0), 8.28 (d, 1H, J 9.0), 8.33 (d, 1H, J 5.5). HRMS (ESI): m/z 411.2048 $[M+H]^+$; calcd. for $C_{20}H_{27}N_8S^+$ $[M+H]^+$ 411.2074. Anal. RP-HPLC Method A: $t_R$ 8.77 min, purity>99%; Method B: $t_R$ 3.24 min, purity>95%

5-(5-Fluoro-2-((5-(4-methylpiperazin-1-yl)pyridin-2-yl)amino)pyrimidin-4-yl)-N,N,4-trimethylthiazol-2-amine (46)

To a solution of crude 1-(5-(4-methylpiperazin-1-yl)pyridine-2-yl)guanidine trifluoroacetate (468 mg, 2.00 mmol) in 2-methoxyethanol (3 mL) were added (E)-3-(dimethylamino)-1-(2-(dimethylamino)-4-methylthiazol-5-yl)prop-2-en-1-one (257 mg, 1.00 mmol) and NaOH (80.0 mg, 2.00 mmol). The reaction mixture was heated at 180° C. for 1 h under microwave irradiation, cooled down to room temperature, and then concentrated under reduced pressure. The residue was purified by chromatography (silica gel, DCM ramping to DCM:MeOH=95:5 with constant addition of 0.5 ml of 32% ammonia) to give 46 as a reddish brown solid (61.0 mg, 14%). $^1$H NMR ($CDCl_3$) δ 2.36 (s, 3H), 2.57 (d, 3H, J 2.5), 2.59 (t, 4H, J 5.0), 3.17 (s, 10H), 7.30 (dd, 1H, J 9.0 & 3.0), 8.33 (d, 1H, J 2.0), 8.18 (d, 1H, J 9.0), 8.23 (d, 1H, J 3.5). HRMS (ESI): m/z 429.1981 $[M+H]^+$); calcd. for $C_{20}H_{26}FN_8S$ $[M+H]^+$ 429.1980. Anal. RP-HPLC Method A: $t_R$ 8.99 min, purity>96%; Method B: $t_R$ 7.30 min, purity>98%.

5-(2-((5-(4-(dimethylamino)piperidin-1-yl)pyridin-2-yl)amino)-5-fluoropyrimidin-4-yl)-N,4-dimethylthiazol-2-amine (47)

To a solution of crude 1-(5-(4-(dimethylamino)piperidin-1-yl)pyridin-2-yl)guanidine trifluoroacetate (524 mg, 2.00 mmol) in 2-methoxyethanol (3 mL) were added ((E)-3-(dimethylamino)-2-fluoro-1-(4-methyl-2-(methylamino)thiazol-5-yl)prop-2-en-1-one (243 mg, 1.00 mmol) and NaOH (80.0 mg, 2.00 mmol). The reaction mixture was heated at 180° C. for 1 h under microwave irradiation, cooled down to room temperature, and then concentrated under reduced pressure. The residue was purified by chromatography (silica gel, DCM ramping to DCM:MeOH=90:10 with constant addition of 0.5 ml of 32% ammonia) to give 47 as a brown solid (76 mg, 17.2%). $^1$H NMR (DMSO-$d_6$) δ 1.50 (q, 2H, J 11.0), 1.84 (d, 3H, J 11.0), 2.21 (s, 7H), 2.47 (s, 3H, thiazole-$CH_3$), 2.64 (t, 2H, J 11.0), 2.86 (t, 3H, J 3.5), 3.63 (d, 1H, J 11.0), 7.39 (app d, 1H, J 7.0), 7.92 (d, 1H, J 9.0), 7.98 (s, 1H), 8.10(1H, J 4.0), 8.41 (s, 1H), 9.43 (s, 1H). HRMS (ESI): m/z 443.2136 $[M+H]^+$; calcd. for $C_{21}H_{28}FN_8S^+$ $[M+H]^+$ 443.2133. Anal. RP-HPLC Method A: $t_R$ 9.12 min, purity>95%; Method B: $t_R$ 2.84 min, >99%.

1-(4-(6-((4-(2-(Dimethylamino)-4-methylthiazol-5-yl)pyrimidin-2-yl)amino)pyridin-3-yl)piperazin-1-yl)ethan-1-one (48)

To a solution of crude 1-(5-(4-acetylpiperazin-1-yl)pyridin-2-yl)guanidine trifluoroacetate (525 mg, 2.00 mmol) in 2-methoxyethanol (3 mL) were added (E)-3-(dimethylamino)-1-(2-(dimethylamino)-4-methylthiazol-5-yl)prop-2-en-1-one (239 mg, 1.00 mmol) and NaOH (80.0 mg, 2.00 mmol). The reaction mixture was heated at 180° C. for 1 h min under microwave irradiation, cooled down to room temperature, and then concentrated under reduced pressure. The residue was purified by chromatography (silica gel, EtOAc ramping to PE:EtOAc=100%) to give 48 as a yellow solid (100 mg, 10%). m.p. 234-235° C. $^1$H NMR ($CDCl_3$) δ 2.12 (s, 3H), 2.55 (s, 3H), 3.08 (t, 2H, J 5.0), 3.11 (t, 2H, J 5.0), 3.15 (s, 6H), 3.61 (t, 2H, J 5.0), 3.77 (t, 2H, J 4.5), 6.83 (d, 1H, J 5.5), 7.32 (dd, 1H, J 9.0 & 3.0), 8.08 (d, 1H, J 3.0), 8.32 (d, 1H, J 9.0), 8.37 (d, 1H, J 5.5), 8.73 (s, 1H). HRMS (ESI): m/z 439.2040 $[M+H]^+$; calcd. for $C_{21}H_{27}N_8OS^+$ $[M+H]^+$ 439.2023. Anal. RP-HPLC Method A: $t_R$ 10.06 min, purity>97%; Method B: $t_R$ 8.62 min, purity>96%

1-(4-(6-((4-(2-(Dimethylamino)-4-methylthiazol-5-yl)-5-fluoropyrimidin-2-yl)amino)pyridin-3-yl)piperazin-1-yl)ethan-1-one (49)

To a solution of crude 1-(5-(4-acetylpiperazin-1-yl)pyridin-2-yl)guanidine trifluoroacetate (525 mg, 2.00 mmol) in 2-methoxyethanol (3 mL) were added (E)-3-(dimethylamino)-1-(2-(dimethylamino)-4-methylthiazol-5-yl)-2-fluoroprop-2-en-1-one (257 mg, 1.00 mmol) and NaOH (80.0 mg, 2.00 mmol). The reaction mixture was heated at 180° C. for 1 h min under microwave irradiation, cooled down to room temperature, and then concentrated under reduced pressure. The residue was purified by chromatography (silica gel, DCM ramping to DCM:MeOH=95:5 with constant addition of 0.5 ml of 32% ammonia) to give 49 as a reddish brown solid (148 mg, 32%). $^1$H NMR ($CDCl_3$) δ 2.14 (s, 3H), 2.57 (d, 3H, J 2.5), 3.08 (t, 2H, J 10.0), 3.11 (t, 2H, J 10.0), 3.17 (s, 6H), 3.63 (t, 2H, J 10.0), 3.78 (t, 2H, J 10.0), 7.31 (dd, 1H, J 9.0 & 3.0), 8.04 (d, 1H, J 3.0), 8.23 (d, 1H, J 9.0), 8.25 (app d, J 3.0, 1H), 8.31 (s, 1H, NH). HRMS (ESI): m/z 457.1925 $[M+H]^+$; calcd. for $C_{21}H_{26}FNOS^+$ $[M+H]^+$ 457.1929. Anal. RP-HPLC Method A: $t_R$ 10.43 min, purity>95%; Method B: $t_R$ 8.29 min, purity>95%.

5-(5-Fluoro-2-((5-morpholinopyridin-2-yl)amino)pyrimidin-4-yl)-N,N,4-trimethylthiazol-2-amine (50)

To a solution of crude 1-(5-morpholinopyridin-2-yl) guanidine trifluoroacetate trifluoroacetate (443 mg, 2.00 mmol)

in 2-methoxyethanol (3 mL) were added (E)-3-(dimethylamino)-1-(2-(dimethylamino)-4-methylthiazol-5-yl)-2-fluoroprop-2-en-1-one (257 mg, 1.00 mmol) and NaOH (80.0 mg, 2.00 mmol). The reaction mixture was heated at 180° C. for 1 h min under microwave irradiation, cooled down to room temperature, and then concentrated under reduced pressure. The residue was purified by chromatography (silica gel, DCM ramping to DCM:MeOH=95:5 with constant addition of 0.5 ml of 32% ammonia) to give 50 as a reddish brown solid (166 mg, 40%). $^1$H NMR ($CDCl_3$) δ 2.58 (s, 3H), 3.11 (t, 4H, J 5.0), 3.17 (s, 6H), 3.89 (t, 4H, J 4.5), 7.29 (dd, 1H, J 9.0 & 2.5), 8.01 (d, 1H, J 3.0), 8.05 (s, 1H), 8.21 (d, 1H, J 9.0), 8.23 (d, 1H, J 3.5). HRMS (ESI): m/z 416.1665 [M+H]$^+$; calcd. for $C_{19}H_{23}FN_7OS^+$ [M+H]$^+$ 416.1663. Anal. RP-HPLC Method A: $t_{ir}$ 10.60 min, purity>95%; Method B: $t_R$ 8.52 min, purity>97%.

5-(5-fluoro-2-((5-(piperidin-1-yl)pyridin-2-yl)amino) pyrimidin-4-yl)-N,4-di methylthiazol-2-amine (51)

To a solution of crude 1-(5-(piperidin-1-yl)pyridin-2-yl) guanidine (439 mg, 2.00 mmol) in 2-methoxyethanol (3 mL) were added ((E)-3-(dimethylamino)-2-fluoro-1-(4-methyl-2-(methylamino)thiazol-5-yl)prop-2-en-1-one (243 mg, 1.00 mmol) and NaOH (80.0 mg, 2.00 mmol). The reaction mixture was heated at 180° C. for 1 h under microwave irradiation, cooled down to room temperature, and then concentrated under reduced pressure. The residue was purified by chromatography (silica gel, DCM ramping to DCM: MeOH=94:6) to give 51 as a reddish brown solid (66 mg, 17%). $^1$H NMR (DMSO-$d_6$) δ 1.52 (m, 2H), 1.63 (m, 4H), 2.47 (s, 3H), 2.87 (d, 3H, J 5.0), 3.07 (t, 4H, J 5.0), 7.38 (dd, 1H, J 9.0 & 2.5), 7.93 (d, 1H, J 9.0), 7.97 (d, 1H, J 2.5), 8.10 (d, 1H, J 5.0), 8.41 (d, 1H, J 3.5), 9.45 (s, 1H). HRMS (ESI): m/z 400.1710 [M+H]$^+$; calcd. for $C_{19}H_{23}FN_7S^+$ [M+H]$^+$ 400.1714. Anal. RP-HPLC Method A: $t_R$ 12.08 min, purity>95%; Method B: $t_R$ 8.70 min, >98%.

5-(5-fluoro-2-((5-(4-(methylsulfonyl)piperazin-1-yl) pyridin-2-yl)amino)pyrimidin-4-yl)-N,4-dimethylthiazol-2-amine (52)

To a solution of crude 1-(5-(4-(methylsulfonyl)piperazin-1-yl)pyridin-2-yl)guanidine (596 mg, 2.00 mmol) in 2-methoxyethanol (3 mL) were added ((E)-3-(dimethylamino)-2-fluoro-1-(4-methyl-2-(methylamino)thiazol-5-yl) prop-2-en-1-one (243 mg, 1.00 mmol) and NaOH (80.0 mg, 2.00 mmol). The reaction mixture was heated at 180° C. for 1 h under microwave irradiation, cooled down to room temperature, and then concentrated under reduced pressure. The residue was purified by chromatography (silica gel, DCM ramping to DCM:MeOH=94:6) to give 52 as a reddish brown solid (29 mg, 6%). $^1$H NMR (DMSO-$d_6$) δ 2.88 (d, 3H, J 4.5), 2.94 (s, 3H), 3.23 (t, 4H, J 5.0), 3.27 (t, 4H, J 5.5), 3.33 (s, 3H), 7.52 (app d, 1H, J 8.0), 7.6 (d, 1H, J 9.0), 8.02 (d, 1H, J 2.5), 8.15 (d, 1H, J 4.5), 8.44 (d, 1H, J 3.5), 9.69 (s, 1H). HRMS (ESI): m/z 479.1441 [M+H]$^+$; calcd. for $C_{19}H_{24}FN_8O_2S^+$ [M+H]$^+$ 479.1442. Anal. RP-HPLC Method A: 10.60 min, purity>94%; Method B: $t_R$ 8.08 min, >97%.

5-(2-((5-(1,4-diazepan-1-yl)pyridin-2-yl)amino)-5-fluoropyrimidin-4-yl)-N,4-dimethylthiazol-2-amine (53)

To a solution of crude 1-(5-(1,4-diazepan-1-yl)pyridin-2-yl)guanidine di(2,2,2-trifluoroacetate) (469 mg, 2.00 mmol) in 2-methoxyethanol (3 mL) were added ((E)-3-(dimethylamino)-2-fluoro-1-(4-methyl-2-(methylamino)thiazol-5-yl) prop-2-en-1-one (243 mg, 1.00 mmol) and NaOH (80.0 mg, 2.00 mmol). The reaction mixture was heated at 180° C. for 1 h under microwave irradiation, cooled down to room temperature, and then concentrated under reduced pressure. The residue was purified by chromatography (silica gel, DCM ramping to DCM:MeOH=90:10) to give 53 as an orange solid (40 mg, 10%). $^1$H NMR (DMSO-$d_6$) δ 1.75-1.80 (m, 2H), 2.45 (d, 3H, 1 2.0), 2.62 (t, 2H, J 6.0), 2.85 (t, 2H, J 5.5), 3.45 (t, 2H, J 5.0),3.53 (t, 2H, J 6.0), 7.13 (dd, 1H, J 9.0 & 3.0), 7.78 (s, 1H), 7.79 (d, 1H, J 4.5), 8.08(q, 1H, J 4.5), 8.37 (d, 1H, J 3.5), 9.21 (s, 1H). HRMS (ESI): m/z 415.1821 [M+H]$^+$; calcd. for $C_{19}H_{24}FN_8S^+$ [M+H]$^+$ 415.1823. Anal. RP-HPLCMethod A: $t_R$ 8.72 min, purity>98%; Method B: $t_R$ 2.84 min, 100%.

5-(5-fluoro-2-(pyridin-2-ylamino)pyrimidin-4-yl)-N, 4-dimethylthiazol-2-amine (54)

To a solution of crude 1-(pyridin-2-yl)guanidine 2,2,2-trifluoroacetate (409 mg, 3.00 mmol) in 2-methoxyethanol (8 mL) were added ((L)-3-(dimethylamino)-2-fluoro-1-(4-methyl-2-(methylamino)thiazol-5-yl)prop-2-en-1-one (487 mg, 2.00 mmol) and NaOH (160 mg, 4.00 mmol). The reaction mixture was heated at 180° C. for 1 h under microwave irradiation, cooled down to room temperature, and then concentrated under reduced pressure. The residue was purified by chromatography (silica gel, DCM ramping to DCM:MeOH=98:2) to give 54 as an orange solid (70 mg, 22%). $^1$H NMR (DMSO-$d_6$) 2.89 (d, 3H, J 4.5), 3.34 (s, 1H), 6.99 (m, 2H), 7.75 (t, 1H, J 7.5), 8.14 (m, 2H), 8.29 (d, 1H, J 3.0), 8.50 (d, 1H, J 3.0), 9.79 (s, 1H). HRMS (ESI): m/z 317.0989 [M+H]$^+$; calcd. for $C_{14}H_{14}FN_6S^+$ [M+H]$^+$ 317.0979. Anal. RP-HPLC Method A: $t_r$ 10.45 min, purity>97%; Method B: $t_R$ 9.24 min, purity>98%.

N-isopropyl-4-methyl-5-(2-((5-(piperazin-1-yl)pyridin-2-yl)amino)pyrimidin-4-yl)thiazol-2-amine (55)

To a suspension of 1-(4-(6-((4-(2-(isopropylamino)-4-methylthiazol-5-yl)pyrimidin-2-yl)amino)pyridin-3-yl)piperazin-1-yl)ethan-1-one (143 mg, 0.32 mmol) in methanol HCl (32%, 3 mL) was added and reflexed overnight. The reaction mixture was concentrated and purified by chromatography (silica gel, DCM ramping to DCM:MeOH: $NH_4OH$=90:10:1) to give 55 as a yellow solid (120 mg, 92%,). $^1$H NMR (DMSO-$d_6$) δ 1.19 (d, 6H, J 6.5, $CH(CH_3)_2$), 2.46 (s, 3H), 2.87 (t, 4H, J 5.0), 3.03 (t, 4H, J 5.5), 3.80-3.87 (m, 1H, CH), 6.90 (d, 1H, J 5.5), 7.37 (dd, 1H, J 9.0 & 3.0), 8.00 (d, 1H, J 3.0), 8.05 (d, 2H, J 7.5), 8.08 (d, 1H, J 9.0), 8.33 (d, 1H, J 5.5), 9.29 (s, 1H). HRMS (ESI): m/z 411.2072 [M+H]$^+$; calcd. for $C_{20}H_{27}N_8S^+$ [M+H]$^+$ 411.2074.Anal. RP-HPLC Method A: $t_R$ 8.43 min, purity>96%; Method B: $t_R$ 7.61 min, purity 99%.

N-isopropyl-4-methyl-5-(2-((5-(4-methylpiperazin-1-yl)pyridin-2-yl)amino)pyrimidin-4-yl)thiazol-2-amine (56)

To a solution of crude 1-(5-(4-methylpiperazin-1-yl)pyridine-2-yl)guanidine trifluoroacetate (468 mg, 2.00 mmol) in 2-methoxyethanol (3 mL) were added (E)-3-(dimethylamino)-1-(2-(isopropylamino)-4-methylthiazol-5-yl)prop-2-en-1-one (253 mg, 1.00 mmol) and NaOH (80.0 mg, 2.00 mmol). The reaction mixture was heated at 180° C. for 1 h min under microwave irradiation, cooled down to room temperature, and then concentrated under reduced pressure. The residue was purified by chromatography (silica gel, DCM ramping to DCM:MeOH=94:6) to give 56 as a yellow solid (131 mg, 31%). $^1$H NMR (DMSO-$d_6$) δ 1.19 (d, 6H, J 6.5,), 2.22 (s, 3H), 2.46 (s br, 7H), 3.11 (t, 4H, J 5.0), 3.81-3.85 (m, 1H), 6.90 (d, 1H, J 5.5), 7.38 (dd, 1H, J 9.0 & 3.0), 8.00 (d, 1H, J 3.0), 8.04 (d, 2H, J 7.5), 8.08 (d, 1H, J 9.0), 8.34 (d, 1H, J 5.5), 9.32 (s, 1H). HRMS (ESI): m/z 425.2235 [M+H]$^+$; calcd. for $C_{21}H_{29}N_8S^+$ [M+H]$^+$ 425.2230.Anal. RP-HPLC Method A: $t_R$ 8.563 min, purity 100%; Method B: $t_R$ 7.73 min, purity 100%.

1-(4-(6-((4-(2-(isopropylamino)-4-methylthiazol-5-yl)pyrimidin-2-yl)amino)pyridin-3-yl)piperazin-1-yl) ethan-1-one (57)

To a solution of crude 1-(5-(4-acetylpiperazin-1-yl)pyridin-2-yl)guanidine trifluoroacetate (525 mg, 2.00 mmol) in 2-methoxyethanol (3 mL) were added (E)-3-(dimethylamino)-1-(2-(isopropylamino)-4-methylthiazol-5-yl)prop-2-en-1-one (253 mg, 1.00 mmol) and NaOH (80.0 mg, 2.00 mmol). The reaction mixture was heated at 180° C. for 1 h min under microwave irradiation, cooled down to room temperature, and then concentrated under reduced pressure. The residue was purified by chromatography (silica gel, DCM ramping to DCM:MeOH=96:4) to give 57 as an orange solid (80 mg, 18%,). $^1$H NMR (DMSO-$d_6$) δ 1.19 (d, 6H, J 6.5), 2.05 (s, 3H), 2.46 (s, 3H), 3.06 (t, 2H, J 5.0), 3.13 (t, 2H, J 5.0), 3.59 (q, 4H, J 5.5), 3.81-3.85 (m, 1H), 6.91 (d, 1H, J 5.5), 7.40 (dd, 1H, J 9.0 & 3.0), 8.02 (d, 1H, J 3.0), 8.05 (m, 2H, J 7.5), 8.10 (d, 1H, J 9.0), 8.33 (d, 1H, J 5.5), 9.31 (s, 1H). HRMS (ESI): m/z 453.2187 [M+H]$^+$; calcd. for $C_{22}H_{29}N_8OS^+$[M+H]$^+$ 453.2180. Anal. RP-HPLC Method A: $t_R$ 10.03 min, purity 100%; Method B: $t_R$ 8.85 min, purity>99%.

N-isopropyl-4-methyl-5-(2-((5-morpholinopyridin-2-yl)amino)pyrimidin-4-yl)thiazol-2-amine (58)

To a solution of crude 1-(5-morpholinopyridin-2-yl)guanidine trifluoroacetate (443 mg, 2.00 mmol) in 2-methoxyethanol (3 mL) were added (E)-3-(dimethylamino)-1-(2-(isopropylamino)-4-methylthiazol-5-yl)prop-2-en-1-one (253 mg, 1.00 mmol) and NaOH (80.0 mg, 2.00 mmol). The reaction mixture was heated at 180° C. for 1 h min under microwave irradiation, cooled down to room temperature, and then concentrated under reduced pressure. The residue was purified by chromatography (silica gel, DCM ramping to DCM:MeOH=96:4) to give 58 as a yellow solid (200 mg, 48%,). $^1$H NMR (DMSO-$d_6$) δ 1.19 (d, 6H, J 6.5), 2.45 (s, 3H), 3.09 (t, 4H, J 4.0), 3.76 (t, 4H, J 4.0), 3.81-3.85 (m, 1H), 6.90 (d, 1H, J 5.5), 7.39 (dd, 1H, J 9.0 & 3.0), 7.01 (d, 1H, J 2.5), 8.05 (d, 2H, J 7.5), 8.10 (d, 1H, J 9.0), 8.34 (d, 1H, J 5.5), 9.33 (s, 1H). HRMS (ESI): m/z 412.1912 [M+H]$^+$; calcd. for $C_{20}H_{26}N_7OS^+$ [M+H]$^+$ 412.1914.Anal. RP-HPLC Method A: $t_R$ 10.21 min, purity 100%; Method B: $t_R$ 9.08 min, purity>99%.

5-(2-((5-(1,4-diazepan-1-yl)pyridin-2-yl)amino)pyrimidin-4-yl)-N-isopropyl-4-methylthiazol-2-amine (59)

To a solution of crude 1-(5-(1,4-diazepan-1-yl)pyridin-2-yl)guanidine di(2,2,2-trifluoroacetate) (469 mg, 2.00 mmol) in 2-methoxyethanol (3 mL) were added (E)-3-(dimethylamino)-1-(2-(isopropylamino)-4-methylthiazol-5-yl)prop-2-en-1-one (253 mg, 1.00 mmol) and NaOH (80.0 mg, 2.00 mmol). The reaction mixture was heated at 180° C. for 1 h min under microwave irradiation, cooled down to room temperature, and then concentrated under reduced pressure. The residue was purified by chromatography (silica gel, DCM ramping to DCM:MeOH=90:10) to give 59 as an range solid (114 mg, 34%). $^1$H NMR (DMSO-$d_6$) δ 1.19 (d, 6H, J 6.5), 2.04-2.09 (m, 2H), 2.47 (s, 3H), 3.16 (s, 1H, J 5.5), 3.27 (s, 2H, J 5.0), 3.50 (d, 2H, J 6.0), 3.70 (t, 2H, J 5.0), 3.80-3.86 (m, 1H), 6.87 (d, 1H, J 5.5), 7.24 (dd, 1H, J 9.0 & 3.0), 7.89 (d, 1H, J 3.0), 8.03 (d, 2H, J 5.5), 8.05 (d, 1H, J 4.0), 8.31 (d, 1H, J 5.5), 8.75 (s, 1H). 9.15 (s, 1H). HRMS (ESI): m/z 425.2231 [M+H]$^+$; calcd. for $C_{21}H_{29}N_8S^+$ [M+H]$^+$ 425.2230 Anal. RP-HPLC Method A: $t_R$ 8.48 min, purity>95%; Method B: $t_R$ 7.69 min, >98%.

N-Cyclopentyl-4-methyl-5-(2-((5-(piperazin-1-yl) pyridin-2-yl) amino) pyrimidin-4-yl) thiazol-2-amine (60)

To a mixture of crude 1-(5-(piperazin-1-yl)pyridin-2-yl) guanidine trifluoroacetate (441 mg, 2.00 mmol) and (E)-1-(2-(cyclopentylamino)-4-methylthiazol-5-yl)-3-(dimethylamino) prop-2-en-1-one (279 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM: MeOH=92:8) and recrystallised with DCM and MeOH to give 60 as a dark yellow solid (70.0 mg, 16%). m.p. 210-213° C. $^1$H NMR (DMSO-$d_6$) 1.49-1.68 (m, 7H), 1.89-1.94 (m, 2H), 2.46 (s, 3H), 2.85 (t, 4H, J 4.5), 3.02 (t, 4H, J 5.0), 3.98 (m, 1H), 6.90 (d, 1H, J 5.5), 7.36 (dd, 1H, J 9.0 & 3.0), 7.98 (d, 1H, J 3.0), 8.07 (d, 1H, J 9.0), 8.18 (d, 1H, J 7.0), 8.33 (d, 1H, J 5.5), 9.33 (s, 1H). HRMS (ESI): m/z 437.2222 [M+H]$^+$; calcd. for $C_{22}H_{29}N_8S^+$ [M+H]$^+$ 437.2230. Anal. RP-HPLC Method A: $t_R$ 10.10 min, purity>99%; Method B: $t_R$ 7.78 min, purity>99%.

N-cyclopentyl-5-(5-fluoro-2-((5-(piperazin-1-yl) pyridin-2-yl)amino)pyrimidin-4-yl)-4-methylthiazol-2-amine (61)

To a mixture of crude 1-(5-(piperazin-1-yl)pyridin-2-yl) guanidine trifluoroacetate (441 mg, 2.00 mmol) and ((E)-1-(2-(cyclopentylamino)-4-methylthiazol-5-yl)-3-(dimethylamino)-2-fluoroprop-2-en-1-one (297 mg, 1.00 mmol) in 2-methoxyethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH:$NH_4OH$=90:10:1) to give 61 as a yellow solid (101 mg, 22%). $^1$H NMR (DMSO-$d_6$) 1.54-1.57 (m, 4H), 1.66-1.69 (m, 2H), 1.92-1.95 (m, 2H), 2.47 (s, 3H), 3.26 (t, 4H, J 2.5), 3.31 (t, 4H, J 2.5), 3.95 (m, 1H, cyclopentane-CH), 7.46 (dd, 1H, J 9.0 & 3.0), 8.00 (d, 1H, J 9.0), 8.05 (d, 1H, J 3.0), 8.25 (d, 1H, J 7.0), 8.42 (d, 1H, J 3.5), 8.84 (d, 1H, J 3.5), 9.57 (s, 1H). HRMS (ESI): m/z 455.2139 [M+H]$^+$; calcd. for $C_{22}H_{28}FN_8S^+$ [M+H]$^+$ 455.2136. Anal. RP-HPLC Method A: $t_R$ 9.55 min, purity 100%; Method B: $t_R$ 7.86 min, purity 100%.

N-cyclopentyl-5-(2-((5-(piperazin-1-yl)pyridin-2-yl) amino)pyrimidin-4-yl)-4-(trifluoromethyl)thiazol-2-amine (62)

To a mixture of crude 1-(5-(piperazin-1-yl)pyridin-2-yl) guanidine trifluoroacetate (441 mg, 2.00 mmol) and (E)-1-

(2-(cyclopentylamino)-4-(trifluoromethyl)thiazol-5-yl)-3-(dimethylamino)prop-2-en-1-one (333 mg, 1.00 mmol) in 2-methoxyethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH:$NH_4OH$=90:10:1) to give 62 as an orange solid (260 mg, 53%). $^1$H NMR (DMSO-$d_6$) δ 1.50-1.59 (m, 4H), 1.65-1.70 (m, 2H), 1.92-1.97 (m, 2H), 2.26 (s, 1H), 2.84 (t, 4H, J 5.0), 3.02 (t, 4H, J 5.0), 3.96 (m, 1H), 6.96 (d, 1H, J 6.0), 7.37 (dd, 1H, J 9.0 & 3.0), 7.98 (d, 1H, J 4.0), 7.99 (d, 1H, J 1.0), 8.50 (d, 1H, J 5.5), 8.59 (d, 1H, J 6.5), 9.59 (s, 1H,). HRMS (ESI): m/z 491.1952 [M+H]$^+$; calcd. for $C_{22}H_{26}F_3N_8S^+$ [M+H]$^+$ 491.1948. Anal. RP-HPLC Method A: $t_R$ 10.31 min, purity 100%; Method B: $t_R$ 8.30 min, >98%.

N-Cyclopentyl-4-methyl-5-(2-((5-(4-methylpiperazin-1-yl)pyridin-2-yl)amino)pyrimidin-4-yl)thiazol-2-amine (63)

To a mixture of crude 1-(5-(4-methylpiperazin-1-yl)pyridine-2-yl)guanidine trifluoroacetate (468 mg, 2.00 mmol) and (E)-1-(2-(cyclopentylamino)-4-methylthiazol-5-yl)-3-(dimethylamino) prop-2-en-1-one (279 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH=93:7) and recrystallised with DCM and MeOH to give 63 as a yellow solid (100 mg, 22%). m.p. 202-205° C. $^1$H NMR ($CDCl_3$) δ 1.51-1.71 (m, 6H), 1.99-2.05 (m, 2H), 2.35 (s, 3H), 2.48 (s, 3H), 2.62 (t, 4H, J 5.0), 3.14 (t, 4H, J 5.0), 3.79 (br, 1H),), 6.03 (br, 1H), 6.78 (d, 1H, J 5.0), 7.27 (dd, 1H, J 9.0 & 3.0), 7.96 (d, 1H, J 3.0), 8.10 (s, 1H), 8.21 (d, 1H, J 9.0), 8.29 (d, 1H, J 5.0). HRMS (ESI): m/z 451.2396 [M+H]$^+$; calcd. for $C_{23}H_{31}N_8S^+$ [M+H]$^+$ 451.2387. Anal. RP-HPLC Method A: $t_R$ 9.56 min, purity>99%; Method B: $t_R$ 9.50 min, purity>98%.

N-cyclopentyl-5-(5-fluoro-24(5-(4-methylpiperazin-1-yl)pyridin-2-yl)amino)pyrimidin-4-yl)-4-methylthiazol-2-amine (64)

To a mixture of crude 1-(5-(4-methylpiperazin-1-yl)pyridine-2-yl)guanidine trifluoroacetate (234 mg, 1.00 mmol) and (E)-1-(2-(cyclopentylamino)-4-methylthiazol-5-yl)-3-(dimethylamino)-2-fluoroprop-2-en-1-one (148 mg, 0.50 mmol) in 2-methoxy ethanol (3 mL) was added NaOH (40.0 mg, 1.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH:$NH_4OH$=94:6:0.5) and recrystallised with $Et_2O$ to give 64 as a dark brown solid (100 mg, 5%). m.p. 207-209° C. $^1$H NMR ($CDCl_3$) δ 1.52-1.79 (m, 6H), 1.06-2.12 (m, 2H), 2.38 (s, 3H), 2.55 (s, 3H), 2.63 (t, 4H, J 5.0), 3.18 (t, 4H, J 5.0), 3.84 (m, 1H), 5.56 (d, J 6.0, 1H), 7.31 (dd, 1H, J 9.0 & 3.0), 7.82 (s, 1H), 7.99 (d, 1H, J 3.0), 8.18 (d, 1H, J 9.0), 8.23 (d, 1H, J 3.5). HRMS (ESI): m/z 469.2287 [M+H]$^+$; calcd. for $C_{23}H_{30}N_8S^+$[M+H]$^+$ 469.2293. Anal. RP-HPLC Method A: $t_R$ 10.37 min, purity>97%; Method B: $t_R$ 8.42 min, purity>98%.

N-cyclopentyl-5-(2-((5-(4-methylpiperazin-1-yl)pyridin-2-yl)amino)pyrimidin-4-yl)-4-(trifluoromethyl)thiazol-2-amine (65)

To a mixture of crude 1-(5-(4-methylpiperazin-1-yl)pyridine-2-yl)guanidine trifluoroacetate (468 mg, 2.00 mmol) and (E)-1-(2-(cyclopentylamino)-4-(trifluoromethyl)thiazol-5-yl)-3-(dimethylamino)-2-fluoroprop-2-en-1-one (148 mg, 0.50 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH=94:6) to give 65 as a brown solid (30 mg, 6%).$^1$H NMR (DMSO-$d_6$) δ 1.56-1.59 (m, 4H), 1.67-1.69 (m, 2H), 1.93-1.97 (m, 2H), 2.21 (s, 1H), 2.46 (t, 4H, J 5.0), 3.12 (t, 4H, J 5.0), 3.96 (m, 1H), 6.96 (d, 1H, J 6.0), 7.39 (dd, 1H, J 9.0 & 3.0), 8.00 (d, 1H, J 9.0), 8.01 (d, 1H, J 3.0), 8.50 (d, 1H, J 5.5), 8.59 (d, 1H, J 7.0), 9.62(s, 1H). HRMS (ESI): m/z 505.2103 [M+H]$^+$; calcd. for $C_{23}H_{28}F_3N_8S^+$ [M+H]$^+$ 505.2104. Anal. RP-HPLC Method A: $t_R$ 10.49 min, purity 96%; Method B: $t_R$ 9.46 min, >97%.

N-Cyclopentyl-5-(2-((5-(4-ethylpiperazin-1-yl)pyridin-2-yl)amino)pyrimidin-4-yl)-4-methylthiazol-2-amine (66)

To a mixture of crude 1-(5-(4-ethylpiperazin-1-yl)pyridin-2-yl)guanidine trifluoroacetate (496 mg, 2.00 mmol) and (E)-1-(2-(cyclopentylamino)-4-methylthiazol-5-yl)-3-(dimethylamino) prop-2-en-1-one (279 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH=96:4) and recrystallised from MeOH to give 66 as a yellow solid (117 mg, 25%). $^1$H NMR ($CDCl_3$) δ 1.14 (t, 3H, J 7.0), 1.56-1.76 (m, 6H), 2.06-2.12 (m, 2H), 2.49 (q, 2H, J 7.5), 2.54 (s, 3H), 2.64 (s, 3H), 3.19 (t, 4H, J 4.5), 3.14 (t, 4H, J 5.0), 3.86 (app s, 1H), 5.77 (s, 1H), 6.84 (d, 1H, J 5.0), 7.34 (dd, 1H, J 9.0 & 3.0), 7.94 (d, 1H, J 3.0), 7.94 (s, 1H), 8.01 (d, 1H, J 3.0), 8.26 (d, 1H, J 9.0), 8.33 (d, 1H, J 5.5). HRMS (EST): m/z 465.2541 [M+H]$^+$; calcd. for $C_{24}H_{33}N_8S^+$ [M+H]$^+$ 465.2543. Anal. RP-HPLC Method A: $t_R$ 13.24 min, purity>98%; Method B: $t_R$ 8.96 min, purity 100%.

N-cyclopentyl-5-(2-((5-(4-ethylpiperazin-1-yl)pyridin-2-yl)amino)-5-fluoropyrimidin-4-yl)-4-methylthiazol-2-amine (67)

To a mixture of crude 1-(5-(4-ethylpiperazin-1-yl)pyridin-2-yl)guanidine trifluoroacetate (497 mg, 2.00 mmol) and ((E)-1-(2-(cyclopentylamino)-4-methylthiazol-5-yl)-3-(dimethylamino)-2-fluoroprop-2-en-1-one (297 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH=95:5) to give 67 as a yellow solid (74 mg, 15%). $^1$H NMR (DMSO-$d_6$) δ 1.03 (t, 3H, J 7.0), 1.50-1.57 (m, 4H), 1.66-1.69 (m, 2H), 1.90-1.95 (in, 2H), 2.37 (q, 2H, J 7.0), 2.46 (d, 3H, J 2.5), 3.11 (t, 4H, J 5.0), 3.32 (s, 4H), 3.96 (app s, 1H), 7.39 (dd, 1H, J 9.0 & 3.0), 7.94 (d, 1H, J 9.0), 7.97 (d, 1H, J 3.0), 8.23 (d, 1H, J 7.0), 8.40 (d, 1H, J 3.5), 9.44 (s, 1H). HRMS (ESI): m/z 483.2442 [M+H ]$^+$; calcd. for $C_{24}H_{32}FN_8S^+$ [M+H]$^+$ 483.2449. Anal. RP-HPLC Method A: $t_R$ 9.78 min, purity>98%; Method B: $t_R$ 7.88 min, purity 100%.

1-(4-(6-((4-(2-(Cyclopentylamino)-4-methylthiazol-5-yl) pyrimidin-2-yl) amino) pyridin-3-yl) piperazin-1-yl) ethan-1-one (68)

To a mixture of crude 1-(5-(4-acetylpiperazin-1-yl)pyridin-2-yl)guanidine trifluoroacetate (524 mg, 2.00 mmol) and (E)-1-(2-(cyclopentylamino)-4-methylthiazol-5-yl)-3-(dimethylamino) prop-2-en-1-one (279 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by using chromatography (silica gel, DCM ramping to DCM:MeOH=90:10) to give 68 as a light yellow solid (153 mg, 32%). m.p. 207-210° C. $^1$H NMR ($CDCl_3$) δ 1.57-1.75 (m, 6H), 2.05-2.11 (m, 2H), 2.14 (s, 3H), 2.54 (s, 3H), 3.08-3.14 (m, 4H), 3.63 (t, 2H, J 5.0), 3.79 (t, 2H, J 5.0), 3.87 (m, 1H), 5.70 (s, 1H), 6.86 (d, 1H, J 5.0), 7.33 (dd, 1H, J 9.0 & 3.0), 8.03 (d, 1H, J 2.0), 8.19 (br s, 1H,), 8.31 (d, 1H, J 9.0), 8.35 (d, 1H, J 5.0). HRMS (ESI): m/z 479.2340 [M+H]$^+$; calcd. for $C_{24}H_{31}N_8OS^+$ [M+H]$^+$ 479.2336 Anal. RP-HPLC Method A: $t_R$ 10.86 min, purity>99%.; Method B: $t_R$ 8.51 min, purity>98%.

1-(4-(6-((4-(2-(cyclopentylamino)-4-methylthiazol-5-yl)-5-fluoropyrimidin-2-yl)amino)pyridin-3-yl) piperazin-1-yl)ethan-1-one (69)

To a mixture of crude 1-(5-(4-acetylpiperazin-1-yl)pyridin-2-yl)guanidine trifluoroacetate (524 mg, 2.00 mmol) and (E)-1-(2-(cyclopentylamino)-4-methylthiazol-5-yl)-3-(dimethylamino)-2-fluoroprop-2-en-1-one (297 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by using chromatography (silica gel, DCM ramping to DCM:MeOH=90:10) to give 69 as a light yellow solid (153 mg, 32%). Yellow solid (53 mg, 11%). $^1$H NMR (DMSO-$d_6$) δ 1.51-1.75 (m, 4H), 1.66-1.68 (m, 2H), 1.92-1.95 (m, 2H), 2.04 (s, 3H), 2.47 (d, 3H, J 2.0), 3.06 (t, 2H, J 5.0), 3.12 (t, 2H, J 5.0), 3.58 (t, 4H, J 5.0), 3.96 (t, 1H), 7.43 (dd, 1H, J 9.0 & 3.0), 7.98 (d, 1H, J 9.0), 8.01 (d, 1H, J 3.0), 8.24 (d, 1H, J 7.0), 8.42 (d, 1H, J 3.5), 9.51 (br s, 1H). HRMS (ESI): m/z 497.2245 [M+H]$^+$; calcd. for $C_{24}H_{30}FN_8OS^+$ [M+H]$^+$ 497.2242 Anal. RP-HPLC Method A: $t_R$ 11.02 min, purity>97%.; Method B: $t_R$ 9.91 min, purity>96%.

1-(4-(6-((4-(2-(cyclopentylamino)-4-(trifluoromethyl)thiazol-5-yl)pyrimidin-2-yl)amino)pyridin-3-yl)piperazin-1-yl)ethan-1-one (70)

To a mixture of crude 1-(5-(4-acetylpiperazin-1-yl)pyridin-2-yl)guanidine trifluoroacetate (524 mg, 2.00 mmol) and (E)-1-(2-(cyclopentylamino)-4-(trifluoromethyl)thiazol-5-yl)-3-(dimethylamino)prop-2-en-1-one (333 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by using chromatography (silica gel, DCM ramping to DCM:MeOH=96:4) to give 70 as a brown solid (50 mg, 9%). $^1$H NMR (DMSO-$d_6$) δ 1.53-1.59 (m, 4H), 1.67-1.69 (m, 2H,), 1.94-1.97 (m, 2H), 2.05 (s, 3H), 3.08 (t, 2H, J 4.5), 3.14 (t, 2H, J 4.5), 3.59 (app d, 4H, J 4.5), 3.95 (m, 1H), 6.97 (d, 1H, J 5.0), 7.43 (dd, 1H, J 9.0 & 3.0), 8.02 (s, 1H), 8.04 (d, 1H, J 3.0), 8.50 (d, 1H, J 5.5), 8.59 (d, 1H, J 6.5), 9.66 (s, 1H). HRMS (ESI): m/z 533.2053 [M+H]$^+$; calcd. for $C_{24}H_{27}F_3N_8OS^+$ [M+H]$^+$ 533.2058. Anal. RP-HPLC Method A: $t_R$ 12.56 min, purity>97%; Method B: $t_R$ 9.39 min, >95%.

N-cyclopentyl-4-methyl-5-(2-((5-morpholinopyridin-2-yl)amino)pyrimidin-4-yl)thiazol-2-amine (71)

To a mixture of crude 1-(5-morpholinopyridin-2-yl)guanidine trifluoroacetate (442 mg, 2.00 mmol) and (E)-1-(2-(cyclopentylamino)-4-methylthiazol-5-yl)-3-(dimethylamino) prop-2-en-1-one (279 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH=94:6) and recrystallised with $Et_2O$ to give 71 as a dark brown solid (130 mg, 30%). m.p. 262-263° C. $^1$H NMR ($CDCl_3$) δ 1.57-1.74 (m, 6H), 2.06-2.12 (m, 2H), 2.55 (s, 3H), 3.13 (t, 4H, J 4.5), 3.88 (t, 4H, J 4.5), 5.67 (d, J 4.5, 1H), 6.85 (d, 1H, J 5.5), 7.32 (dd, 1H, J 9.0 & 3.0), 8.02 (d, 1H, J 3.0), 8.16 (s, 1H), 8.30 (d, 1H, J 9.5), 8.35 (d, 1H, J 5.5). HRMS (ESI): m/z 438.2088[M+H]$^+$; calcd. for $C_{22}H_{28}N_7OS^+$ [M+H]$^+$ 438.2071. Anal. RP-HPLC Method A: $t_R$ 10.92 min, purity 100%; Method B: $t_R$ 9.51 min, purity>99%.

N-cyclopentyl-5-(2-((5-morpholinopyridin-2-yl) amino)pyrimidin-4-yl)-4-(trifluoromethyl)thiazol-2-amine (72)

To a mixture of crude 1-(5-morpholinopyridin-2-yl)guanidine trifluoroacetate (442 mg, 2.00 mmol) and (E)-1-(2-(cyclopentylamino)-4-methylthiazol-5-yl)-3-(dimethylamino)-2-fluoroprop-2-en-1-one (297 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH=96:4) and recrystallised with DCM and MeOH to give 72 as a brown solid (120 mg, 26%). $^1$H NMR (DMSO-$d_6$) δ 1.50-1.57 (m, 4H), 1.66-1.69 (m, 2H), 1.90-1.95 (m, 2H), 2.47 (d, 1H, J 2.5), 3.09 (t, 4H, J 5.0), 3.75 (t, 4H, J 5.0), 3.96 (m, 1H), 7.42 (dd, 1H, J 9.0 & 3.0), 7.96 (d, 1H, J 9.0), 7.98 (d, 1H, J 3.0), 8.24 (d, 1H, J 7.0), 8.41 (d, 1H, J 7.0), 9.52(s, 1H). HRMS (ESI): m/z 456.1976 [M+H]$^+$; calcd. for $C_{22}H_{25}F_3N_7OS^+$ [M+H]$^+$ 456.1967. Anal. RP-HPLC Method A: $t_R$ 11.28 min, purity 96%; Method B: $t_R$ 8.93 min, 100%.

N-cyclop entyl-5-(2-((5-morpholinopyridin-2-yl) amino)pyrimidin-4-yl)-4-(trifluoromethyl)thiazol-2-amine (73)

To a mixture of crude 1-(5-morpholinopyridin-2-yl)guanidine trifluoroacetate (442 mg, 2.00 mmol) and (E)-1-(2-(cyclopentylamino)-4-(trifluoromethyl)thiazol-5-yl)-3-(dimethylamino)prop-2-en-1-one(333 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, PE ramping to PE:EtOAc=60:40) to give 73 as an orange solid (200 mg, 41%). $^1$H NMR (DMSO-$d_6$) δ 1.52-1.59 (m, 4H), 1.64-1.69 (m, 2H), 1.92-1.99 (m, 2H), 3.09 (t, 4H, J 4.5), 3.75 (t, 4H, J 4.5), 3.95 (m, 1H), 6.97 (d, 1H, J 5.0), 7.41 (dd, 1H, J 9.0 & 3.0), 8.01 (s, 1H), 8.02 (d, 1H, J 2.5), 8.51(d, 1H, J 5.5), 8.59 (d, 1H, J 6.5), 9.64 (s, 1H). HRMS (ESI): m/z 492.1786 [M+H]$^+$; calcd. for $C_{22}H_{24}F_3N_7OS^+$ [M+H]$^+$ 498.1788. Anal. RP-HPLC Method A: $t_R$ 12.90 min, purity>97%; Method B: $t_R$ 9.69 min, >99%.

5-(2-((5-(4-Aminopiperidin-1-yl)pyridin-2-yl)amino) pyrimidin-4-yl)-N-cyclopentyl-4-methylthiazol-2-amine (74)

To a mixture of crude 1-(5-(4-aminopiperidin-1-yl)pyridin-2-yl)guanidine trifluoroacetate (702 mg, 3.00 mmol) and (E)-1-(2-(cyclopentylamino)-4-methylthiazol-5-yl)-3-(dimethylamino) prop-2-en-1-one (558 mg, 2.00 mmol) in 2-methoxy ethanol (5 mL) was added NaOH (160.0 mg, 4.00 mmol). The reaction mixture was heated at 180° C. under microwave irradiation for 2 h, cooled to room temperature and concentrated under reduced pressure. The residue was purified by chromatography (silica gel, DCM ramping to DCM:MeOH:$MH_4OH$=90:10:1) and recrystallised with n-hexane and DCM to give 74 as a dark yellow solid (90 mg, 10%). m.p. 185-186° C. $^1$H NMR ($CDCl_3$) δ 1.50-1.77 (m, 10H), 1.95 (d, 2H, J 10.5), 2.07-2.13 (m, 2H), 2.54 (s, 3H), 2.75-2.85 (m, 3H), 3.53-3.56 (m, 2H), 3.85-3.91 (m, 1H), 5.43 (d, J 5.0, 1H), 6.84 (d, 1H, J 5.5), 7.34 (dd, 1H, J 9.0 & 3.0), 7.75 (s, 1H), 8.00 (d, 1H, J 3.0), 8.25 (d, 1H, J 9.0), 8.32 (d, 1H, J 5.5). HRMS (ESI): m/z 451.2415 [M+H]$^+$; calcd. for $C_{23}H_{31}N_8S^+$ [M+H]$^+$ 451.2387. Anal. RP-HPLC Method A: $t_R$ 9.34 min, purity>95%; Method B: $t_R$ 8.06 min, purity>95%.

N-cyclopentyl-4-methyl-5-(2-((5-(piperidin-1-yl) pyridin-2-yl)amino)pyrimidin-4-yl)thiazol-2-amine (75)

To a mixture of crude 1-(5-(piperidin-1-yl)pyridin-2-yl) guanidine (439 mg, 2.00 mmol) and (E)-1-(2-(cyclopentylamino)-4-methylthiazol-5-yl)-3-(dimethylamino) prop-2-en-1-one (279 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH=92:8) and recrystallised with DCM and MeOH to give 75 as yellow solid (250 mg, 57%). $^1$H NMR (DMSO-$d_6$) δ 1.53 (s br, 6H), 1.64 (s br, 6H), 1.93 (s br, 2H), 2.46 (s, 3H), 3.07 (t, 4H, J 10.0), 3.98 (s br, H), 6.89 (d, 1H, J 5.0), 7.37 (app d, 1H, J 9.0), 7.99 (s, 1H), 8.06 (d, 1H, J 9.0), 8.18 (s, 1H), 8.33 (d, 1H, J 5.0), 9.26 (s, 1H). HRMS (ESI): m/z 436.2280 [M+H]$^+$; calcd. for $C_{23}H_{30}N_7S^+$ [M+H]$^+$ 436.2278. Anal. RP-HPLC Method A: $t_R$ 12.08 min, purity>99%; Method B: $t_R$ 9.36 min, >99%.

N-cyclopentyl-4-methyl-5-(2-(pyridin-2-ylamino) pyrimidin-4-yl)thiazol-2-amine (78)

To a mixture of crude 1-(pyridin-2-yl)guanidine 2,2,2-trifluoroacetate (272 mg, 2.00 mmol) and (E)-1-(2-(cyclopentylamino)-4-methylthiazol-5-yl)-3-(dimethylamino) prop-2-en-1-one (279 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM: MeOH=97:3) to give 78 as an orange solid (150 mg, 43%). $^1$H NMR (DMSO-$d_6$) 1.50-1.57 (m, 4H), 1.66-1.69 (m, 2H), 1.91-1.95 (m, 2H), 2.48 (s, 3H), 3.98 (m, 1H), 6.99 (m, 2H), 7.74 (m, 1H), 8.23 (d, 1H, J 7.0), 8.26 (d, 1H, J 8.5), 8.29 (m, 1H), 8.39 (d, 1H, J 5.5), 9.59 (s, 1H). HRMS (ESI): m/z 353.1555 [M+H]$^+$; calcd. for $C_{18}H_{21}N_6S^+$ [M+H]$^+$ 353.1543. Anal. RP-HPLC Method A: $t_R$ 10.45 min, purity>97%; Method B: $t_R$ 9.24 min, purity>98%.

4-(6-((4-(2-(cyclopentylamino)-4-(trifluoromethyl) thiazol-5-yl)pyrimidin-2-yl)amino)pyridin-3-yl)piperazine-1-carbaldehyde (79)

Compound 79 was obtained as beige solid (25 mg, 7%) by-product in the process of synthesising and purifying N-cyclopentyl-5-(2-((5-(piperazin-1-yl)pyridin-2-yl)amino) pyrimidin-4-yl)-4-(trifluoromethyl)thiazol-2-amine. $^1$H NMR (DMSO-$d_6$) δ 1.53-1.59 (m, 4H), 1.67-1.69 (m, 2H), 1.94-1.97 (m, 2H), 3.08 (t, 2H,15.0), 3.14 (t, 2H, J 5.0), 3.59 (m, 4H), 3.96 (m, 1H), 6.97 (d, 1H, J 4.5), 7.45 (dd, 1H, J 9.0 & 3.0), 8.03 (d, 1H, J 9.0), 8.05 (d, 1H, J 3.0), 8.09 (s, 1H), 8.50 (d, 1H, J 5.5), 8.59 (d, 1H, J 7.0), 9.67 (s, 1H). HRMS (ESI): m/z 519.1897 [M+H]$^+$; calcd. for $C_{23}H_{26}F_3N_8OS^+$ [M+H]$^+$ 519.1906. Anal. RP-HPLC Method A: $t_R$ 11.57 min, purity>91%; Method B: $t_R$ 9.39 min, >95%.

N-cyclopentyl-5-(2-((5-(4-(dimethylamino)piperidin-1-yl)pyridin-2-yl)amino)-5-fluoropyrimidin-4-yl)-4-methylthiazol-2-amine (80)

To a mixture of crude 1-(5-(4-(dimethylamino)piperidin-1-yl)pyridin-2-yl)guanidine trifluoroacetate (524 mg, 2.00 mmol) and (E)-1-(2-(cyclopentylamino)-4-methylthiazol-5-yl)-3-(dimethylamino)-2-fluoroprop-2-en-1-one (297 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH:NH4OH=90:10:1) to give 80 as yellow solid (134 mg, 27%). $^1$H NMR (DMSO-$d_6$) δ 1.49-1.56 (m, 6H), 1.64-1.70 (m, 2H), 1.84 (d, 3H, J 11.5), 1.90-1.96 (m, 2H), 2.20 (s, 7H), 2.46 (s, 3H), 2.65 (t, 2H, J 11.0), 3.63 (d, 1H, J 12.0), 3.92-3.99 (m, 1H), 7.39 (dd, 1H, J 9.0 & 3.0), 7.93 (d, 1H, J 9.0), 7.98 (d, 1H, J 2.5), 8.23(1H, J 7.0), 8.40 (d, 1H, J 3.0), 9.41 (s, 1H). HRMS (ESI): m/z 497.2608 [M+H]$^+$; calcd. for $C_{25}H_{34}FN_8S^+$ [M+H]$^+$ 497.2606. Anal. RP-HPLC Method A: $t_R$ 9.81 min, purity>95%; Method B: $t_R$ 8.75 min, >99%.

5-(2-((5-(1,4-diazepan-1-yl)pyridin-2-yl)amino)-5-fluoropyrimidin-4-yl)-N-cyclopentyl-4-methylthiazol-2-amine (81)

To a mixture of crude 1-(5-(1,4-diazepan-1-yl)pyridin-2-yl)guanidine di(2,2,2-trifluoroacetate) (469 mg, 2.00 mmol) and (E)-1-(2-(cyclopentylamino)-4-methylthiazol-5-yl)-3-(dimethylamino)-2-fluoroprop-2-en-1-one (297 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH=90:10) to give 81 as a yellow solid (100 mg, 21%). $^1$H NMR (DMSO-$d_6$) δ 1.49-1.59 (m, 4H), 1.64-1.72 (m, 2H), 1.92-1.95 (m, 2H), 2.05-2.09 (m, 2H), 2.47 (d, 3H, J 2.0), 2.55 (s, 1H), 3.16 (s br, 2H), 3.27 (d, 2H, J 4.0), 3.70 (t, 2H, J 5.0), 3.94-3.98 (m, 1H), 7.32 (dd, 1H, J 9.0 & 3.0), 7.87 (d, 1H, J 2.5), 7.89 (d, 1H, J 3.0), 8.27 (d, 1H, J 7.0), 8.40 (d, 1H, J 3.5), 8.9 (s br, 1H), 9.54 (s, 1H). HRMS (ESI): m/z 469.2297 [M+H]$^+$; calcd. for $C_{23}H_{30}FN_8S^+$ [M+H]$^+$ 469.2293. Anal. RP-HPLC Method A: $t_R$ 9.53 min, purity>97%; Method B: $t_R$ 8.53 min, 100%.

N-cyclopentyl-5-(5-fluoro-2-((5-(4-(methylsulfonyl) piperazin-1-yl)pyridin-2-yl)amino)pyrimidin-4-yl)-4-methylthiazol-2-amine (82)

To a mixture of crude 1-(5-(4-(methylsulfonyl)piperazin-1-yl)pyridin-2-yl)guanidine (596 mg, 2.00 mmol) and (E)-1-(2-(cyclopentylamino)-4-methylthiazol-5-yl)-3-(dimethylamino)-2-fluoroprop-2-en-1-one (297 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH=96:4) to give 82 as yellow solid (53 mg, 10%). $^1$H NMR (DMSO-$d_6$) 1.51-1.57 (m, 4H), 1.66-1.68 (m, 2H), 1.91-1.95 (m, 2H), 2.47 (s, 3H), 2.94 (s, 3H), 3.22 (t, 4H, J 5.0), 3.26 (t, 4H, J 5.0), 3.95-3.97 (m, 1H), 7.46 (dd, 1H, J 9.0 & 2.5), 7.98 (d, 1H, J 9.0), 8.02 (d, 1H, J 2.5), 8.24 (d, 1H, J 7.0), 8.42 (d, 1H, J 3.5), 9.57 (s, 1H). HRMS (ESI): m/z 533.1916 [M+H]$^+$; calcd. for $C_{23}H_{30}FN_8O_2S_2^+$ [M+H]$^+$ 533.1912. Anal. RP-HPLC Method A: $t_R$ 10.96 min, purity>99%; Method B: $t_R$ 10.25 min, purity>98%.

N-cyclopentyl-5-(2-((5-((4-ethylpiperazin-1-yl) methyl)pyridin-2-yl)amino)pyrimidin-4-yl)-4-methylthiazol-2-amine (83)

To a solution of 5-(2-aminopyrimidin-4-yl)-N-cyclopentyl-4-methylthiazol-2-amine (275 mg, 1.00 mmol) in dioxane (3 mL) were added 1-((6-bromopyridin-3-yl) methyl)-4-ethylpiperazine (341 mg, 1.2 mmol), $Pd_2dba_3$ (45.8 mg, 0.05 mmol), xantphose (58 mg, 0.1 mmol) and t-BuONa (144 mg, 1.5 mmol) and heated under microwave irradiation at 150° C. for 1 h. The reaction mixture was cooled to room temperature and concentrated under reduced pressure. The residue was purified by chromatography (silica gel, DCM ramping to DCM:MeOH:$NH_4OH$=9:1:0.3) and recrystallised with DCM and MeOH to give 83 as a white solid (200 mg, 42%). $^1$H NMR ($CDCl_3$) δ 1.09 (t, 3H, J 7.0), 1.58-1.76 (m, 6H), 2.08-2.14 (m, 2H), 2.43 (q, 2H, J 7.0, $CH_2CH_3$), 2.55 (s br, 11H), 3.48 (s, 2H), 3.86-3.92 (m, 1H), 5.42 (d, 2H, J 7.0), 6.90(d, 1H, J 5.5), 7.68 (dd, 1H, J 9.0 & 2.5), 7.89 (s, 1H), 8.19 (d, 1H, J 2.0), 8.35-8.38 (m, 2H). HRMS (ESI): m/z 479.2703 [M+H]$^+$; calcd. for $C_{25}H_{35}N_8S^+$ [M+H]$^+$ 479.2700. Anal. RP-HPLC Method A: $t_R$ 9.89 min, purity>96%; Method B: $t_R$ 8.66 min, purity>96%.

N-cyclopentyl-5-(2-((5-((4-ethylpiperazin-1-yl) methyl)pyridin-2-yl)amino)-5-fluoropyrimidin-4-yl)-4-methylthiazol-2-amine (84)

To a solution of 5-(2-amino-5-fluoropyrimidin-4-yl)-N-cyclopentyl-4-methylthiazol-2-amine (200 mg, 0.68 mmol) in dioxane (3 mL) were added 1-((6-bromopyridin-3-yl) methyl)-4-ethylpiperazine (233 mg, 0.82 mmol), Pd2dba3 (31 mg, 0.034 mmol), xantphose (41 mg, 0.07 mmol) and t-BuONa (98 mg, 1.02 mmol) and heated under microwave irradiation at 150° C. for 1 h. The reaction mixture was cooled to room temperature and concentrated under reduced pressure. The residue was purified by chromatography (silica gel, DCM ramping to DCM:MeOH=93:7) to give 84 as an orange solid (100 mg, 29%). $^1$H NMR (DMSO-$d_6$) δ 0.99 (t, 3H, J 7.0), 1.49-1.59 (m, 4H), 1.64-1.72 (m, 2H), 1.90-1.97 (m, 2H), 2.38 (s br, 10H), 2.48 (d, 3H, J 2.5), 3.42 (s, 2H), 3.95-3.98 (m, 1H), 7.64 (dd, 1H, J 8.5 & 2.0), 8.10 (d, 1H, J 8.5), 8.16 (d, 1H, J 2.0), 8.27 (d, 1H, J 7.0), 8.46 (d, 1H, J 3.5), 9.77 (s, 1H). HRMS (ESI): m/z 497.2601 [M+H]$^+$; calcd. for $C_{25}H_{34}FN_8S^+$ [M+H]$^+$ 497.2606. Anal. RP-HPLC Method A: $t_R$ 9.89 min, purity>96%; Method B: $t_R$ 8.66 min, purity>96%.

N-Cyclopentyl-N,4-dimethyl-5-(2-((5-(piperazin-1-yl)pyridin-2-yl)amino)pyrimidin-4-yl)thiazol-2-amine (85)

To a mixture of crude 1-(5-(piperazin-1-yl)pyridin-2-yl) guanidine trifluoroacetate (319 mg, 1.45 mmol) and (E)-1-(2-(cyclopentyl(methyl)amino)-4-methylthiazol-5-yl)-3-(dimethylamino)prop-2-en-1-one (250 mg, 0.85 mmol) in 2-methoxy ethanol (3 mL) was added NaOH (68.0 mg, 1.70 mmol). The reaction mixture was heated at 180° C. under microwave irradiation for 1 h, cooled to room temperature and concentrated under reduced pressure. The residue was purified by chromatography (silica gel, DCM ramping to DCM:MeOH=93:7) and recrystallised with hexane to give 85 as a reddish brown solid (113 mg, 25%). m.p. 166-169° C. $^1$H NMR ($CDCl_3$) δ 1.58-1.79 (m, 6H), 1.96-2.02 (m, 2H), 2.11 (br, 1H), 2.56 (s, 3H), 3.01 (s, 3H), 3.06 (t, 4H, J 6.), 3.10 (t, 4H, J 6.0), 4.55 (m, 1H), 6.82 (d, 1H, J 5.5), 7.32 (dd, 1H, J 9.0 & 3.0), 8.02 (d, 1H, J 3.0), 8.13 (br, 1H), 8.28 (d, 1H, J 9.0), 8.32 (d, 1H, J 5.5). HRMS (ESI): m/z 451.2387 [M+H]$^+$; calcd. for $C_{23}H_{31}N_8S^+$ [M+H]$^+$ 451 2387. Anal. RP-HPLC Method A: $t_R$ 10.28 min, purity>95%; Method B: $t_R$ 8.69 min, purity>95%.

N-Cyclopentyl-N,4-dimethyl-5-(2-((5-(4-methylpiperazin-1-yl)pyridin-2-yl)amino)pyrimidin-4-yl)thiazol-2-amine (86)

To a mixture of crude 1-(5-(4-methylpiperazin-1-yl)pyridine-2-yl)guanidine trifluoroacetate (468 mg, 2.00 mmol) and (E)-1-(2-(cyclopentyl(methyl)amino)-4-methylthiazol-5-yl)-3-(dimethylamino)prop-2-en-1-one (293 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH:$NH_4OH$=93:7:0.5) and recrystallised with MeOH to give 86 as a yellow solid (149 mg, 32%). m.p. 169-170° C. $^1$H NMR ($CDCl_3$) δ 1.65-1.76 (m, 6H), 1.99-2.02 (m, 2H), 2.56 (s, 3H), 2.75 (s, 3H), 2.75 (s, 3H), 3.16 (br, 4H), 3.47 (t, 4H, J 5.0), 4.58 (m, 1H), 6.86 (d, 1H, J 5.5), 7.36 (dd, 1H, J 9.0 & 3.0), 8.05 (d, 1H, J 3.0), 8.07 (s, 1H), 8.32 (d, 1H, J 5.5), 8.35 (d, 1H, J 9.0). HRMS (ESI): m/z 465.2530 [M+H]$^+$; calcd. for $C_{24}H_{33}N_8S^+$ [M+H]$^+$ 465.2543. Anal. RP-HPLC Method A: $t_R$ 10.15 mm, purity>96%; Method B: $t_R$ 8.47 min, purity>96%.

1-(4-(6-((4-(2-(Cyclopentyl(methyl)amino)-4-methylthiazol-5-yl)pyrimidin-2-yl)amino)pyridin-3-yl) piperazin-1-yl)ethan-1-one (87)

To a mixture of crude 1-(5-(4-acetylpiperazin-1-yl)pyridin-2-yl)guanidine trifluoroacetate (525 mg, 2.00 mmol) and (E)-1-(2-(cyclopentyl(methyl)amino)-4-methylthiazol-5-yl)-3-(dimethylamino)prop-2-en-1-one (293 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH=96:4) and recrystallised with Et2O to give 87 as a yellow solid (300 mg, 61%). m.p. 153-154° C. $^1$H NMR ($CDCl_3$) δ 1.61-1.76 (m, 6H), 1.97-2.02 (m, 2H), 2.15 (s, 3H), 2.57 (s, 3H), 3.01 (s, 3H), 3.09 (t, 2H, J 5.0), 3.13 (t, 2H, J 5.0), 3.63 (t, 2H, J 5.0), 3.79 (t, 2H, J 5.0), 4.56 (m, 1H), 6.85 (d, 1H, J 5.5), 7.34 (dd, 1H, J 9.0 & 3.0), 7.93 (s, 1H), 8.00 (d, 1H, J 3.0), 8.31 (s, 1H), 8.32 (d, 1H, J 5.0). HRMS (ESI): m/z 493.2482 $[M+H]^+$; calcd. for $C_{25}H_{33}N_8OS^+$ $[M+H]^+$ 493.2493. Anal. RP-HPLC Method A: $t_R$ 11.55 min, purity>96%; Method B: $t_R$ 9.57 min, purity>96%.

N,N-Dicyclopentyl-4-methyl-5-(2-((5-(piperazin-1-yl)pyridin-2-yl)amino)pyrimidin-4-yl)thiazol-2-amine (88)

To a mixture of crude 1-(5-(piperazin-1-yl)pyridin-2-yl) guanidine trifluoroacetate (441 mg, 2.00 mmol) and (E)-1-(2-(Dicyclopentylamino)-4-methylthiazol-5-yl)-3-(dimethylamino) prop-2-en-1-one (200 mg, 0.58 mmol) in 2-methoxy ethanol (3 mL) was added NaOH (80.0 mg, 2.00 mmol). The reaction mixture was heated at 180° C. under microwave irradiation for 2 h, cooled to room temperature and concentrated under reduced pressure. The residue was purified by chromatography (silica gel, DCM ramping to DCM:MeOH=90:10) and recrystallised with DCM and MeOH to give 88 yellow solid (60 mg, 21%). $^1$H NMR ($CDCl_3$) 1.53-1.59 (m, 8H), 1.74-1.76 (m, 4H), 1.85-1.89 (m, 2H), 1.91-1.98 (m, 2H), 2.42-2.47 (m, 1H), 2.58 (s, 3H), 3.05 (t, 4H, J 3.0), 3.10 (t, 4H, J 3.0), 3.41-3.44 (m, 1H), 4.47-4.54 (m, 1H), 6.61 (d, 1H, J 5.5), 7.32 (dd, 1H, J 9.0 & 3.0), 7.70 (s, 1H), 7.98 (d, 1H, J 3.0), 8.25 (d, 1H, J 9.0), 8.28 (d, 1H, J 5.5). HRMS (ESI): m/z 505.2873 $[M+H]^+$; calcd. for $C_{27}H_{37}N_8S^+$ $[M+H]^+$ 505.2856. Anal. RP-HPLC Method A: $t_R$ 8.57 min, purity>98%; Method B: $t_R$ 7.33 min, purity>96%.

4-Methyl-N-phenyl-5-(2-((5-(piperazin-1-yl)pyridin-2-yl)amino)pyrimidin-4-yl)thiazol-2-amine (89)

To a mixture of crude 1-(5-(piperazin-1-yl)pyridin-2-yl) guanidine trifluoroacetate (468 mg, 2.00 mmol) and (E)-3-(dimethylamino)-1-(4-methyl-2-(phenylamino)thiazol-5-yl) prop-2-en-1-one (287 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH: $NH_4OH$=90:10:0.5) to give 89 as a light yellow solid (178 mg, 40%). m.p. 228-230° C. $^1$H NMR (DMSO-$d_6$) δ 2.58 (s, 4H), 2.86 (t, 4H, J 4.5), 3.03 (t, 4H, J 4), 7.00 (m, 2H), 7.35 (m, 3H), 7.65 (d, 2H, J 8.0), 8.00 (d, 1H, J 2.5), 8.06 (d, 1H, J 9.0), 8.41 (d, 1H, J 5.0), 9.46 (s, 1H), 10.53 (s, 1H). HRMS (ESI): m/z 445.1918 $[M+H]^+$; calcd. for $C_{23}H_{25}N_8S^+$ $[M+H]^+$ 445.1917. Anal. RP-HPLC Method A: $t_R$ 10.01 min, purity 100%; Method B: $t_R$ 8.17 min, purity 100%.

4-Methyl-5-(2-((5-(4-methylpiperazin-1-yl)pyridin-2-yl)amino)pyrimidin-4-yl)-N-phenylthiazol-2-amine (90)

To a mixture of crude 1-(5-(4-methylpiperazin-1-yl)pyridine-2-yl)guanidine trifluoroacetate (468 mg, 2.00 mmol) and (E)-3-(dimethylamino)-1-(4-methyl-2-(phenylamino) thiazol-5-yl)prop-2-en-1-one (287 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH=90:8) and recrystallised with DCM to give 90 as a light yellow (220 mg, 48%). mp. 210-211° C. $^1$H NMR (DMSO-$d_6$) δ 2.23 (s, 3H), 2.58 (s, 3H), 3.12 (br, 4H), 3.38 (t, 4H), 7.00 (m, 2H), 7.37 (m, 3H), 7.65 (d, 2H, J 8.0), 8.01 (d, 1H, J 2.0), 8.07 (d, 1H, J 9.0), 8.41 (d, 1H, J 5.0), 9.46 (s, 1H), 10.54 (s, 1H). HRMS (ESI): m/z 459.2063 $[M+H]^+$; calcd. for $C_{24}H_{27}N_8S^+$ $[M+H]^+$ 459.2074. Anal. RP-HPLC Method A: $t_R$ 9.93 min, purity 100%; Method B: $t_R$ 9.17 min, purity 100%.

N,4-Dimethyl-5-(2-((5-(4-methylpiperazin-1-yl) pyridin-2-yl)amino)pyrimidin-4-yl)-N-phenylthiazol-2-amine (91)

To a mixture of crude 1-(5-(4-methylpiperazin-1-yl)pyridine-2-yl)guanidine trifluoroacetate (468 mg, 2.00 mmol) and (E)-3-(dimethylamino)-1-(4-methyl-2-(methyl(phenyl) amino)thiazol-5-yl)prop-2-en-1-one (301 mg, 1.00 mmol) in 2-methoxy ethanol (3 mL) was added NaOH (80.0 mg, 2.00 mmol). The reaction mixture was heated at 180° C. under microwave' irradiation for 1 h, cooled to room temperature and concentrated under reduced pressure. The residue was purified by chromatography (silica gel, DCM ramping to DCM:MeOH=92:8) and recrystallised with hexane to give 91 as a reddish brown solid (184 mg, 39%). m.p. 212-215° C. $^1$H NMR ($CDCl_3$) δ 2.36 (s, 3H), 2.59 (app br, 7H), 3.14 (t, 4H, J 5.0), 3.57 (s, 3H), 6.80 (d, 1H, J 5.5), 7.19 (dd, 1H, J 9.0 & 3.0), 7.32 (m, 1H), 7.44 (m, 4H), 8.00 (d, 1H, J 3.0), 8.04 (s, 1H), 8.16 (d, 1H, J 9.0), 8.32 (d, 1H, J 5.5). HRMS (ESI): m/z 473.2220 $[M+H]^+$; calcd. for $C_{25}H_{29}N_8S^+$ $[M+H]^+$ 473.2230. Anal. RP-HPLC Method A: $t_R$ 9.57 min, purity>98%; Method B: $t_R$ 7.90 min, purity>98%.

4-Methyl-5-(2-((5-(4-methylpiperazin-1-yl)pyridin-2-yl)amino)pyrimidin-4-yl)thiazol-2(3H)-one (92)

Compound 92 was obtained as a grey solid (31 mg, 10%) by-product in the process of synthesising and purifying 4-(2-Methoxy-4-methylthiazol-5-yl)-N-(5-(4-methylpiperazin-1-yl)pyridin-2-yl)pyrimidin-2-amine. m.p. 228-230° C. $^1$H NMR (DMSO-$d_6$) 2.23 (s, 3H), 2.42 (s, 3H), 2.47 (t, 4H, J 4.5), 3.12 (t, 4H, J 4.5), 6.90 (d, 1H, J 5.0), 7.45 (dd, 1H, J 9.0 & 3.0), 7.99 (d, 1H, J 3.0), 8.02 (d, 1H, J 9.0), 8.41 (d, 1H, J 5.0), 9.53 (s, 1H). HRMS (ESI): m/z 384.1596 $[M+H]^+$; calcd. for $C_{18}H_{22}N_7OS^+$ $[M+H]^+$ 384.1601. Anal. RP-HPLC Method A: $t_R$ 8.59 min, purity>97%; Method B: $t_R$ 3.59 min, purity>99%.

3,4-Dimethyl-5-(2-((5-(4-methylpiperazin-1-yl)pyridin-2-yl)amino)pyrimidin-4-yl)thiazol-2(3H)-one (93)

To a mixture of crude 1-(5-(4-methylpiperazin-1-yl)pyridine-2-yl)guanidine trifluoroacetate (468 mg, 2.00 mmol)

and (E)-5-(3-(dimethylamino)acryloyl)-3,4-dimethylthiazol-2(3H)-one (226 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM:MeOH: $NH_4OH$=94:6:0.5) and recrystallised with hexane to give 93 as a yellow solid (72 mg, 18%). m.p. 243-244° C. $^1$H NMR ($CDCl_3$) 2.37 (s, 3H), 2.59 (s, 3H), 2.61 (t, 4H, J 4.0), 3.19 (t, 4H, J 4.0), 3.37 (s, 3H), 6.73 (d, 1H, J 5.0), 7.34 (dd, 1H, J 9.0 & 3.0), 7.87 (s, 1H), 8.00 (d, 1H, J 3.0), 8.21 (d, 1H, J 9.0), 8.406 (d, 1H, J 5.0). HRMS (ESI): m/z 398.1769 $[M+H]^+$; calcd. for $C_{19}H_{24}N7OS^+$ $[M+H]^+$ 398.1758. Anal. RP-HPLC Method A: $t_R$ 8.25 min, purity 100%; Method B: $t_R$ 3.31 min, purity 100%.

3-Ethyl-4-methyl-5-(2-((5-(4-methylpiperazin-1-yl) pyridin-2-yl)amino)pyrimidin-4-yl)thiazol-2(3H)-one (94)

To a mixture of crude 1-(5-(4-methylpiperazin-1-yl)pyridine-2-yl)guanidine trifluoroacetate (468 mg, 2.00 mmol) and (E)-5-(3-(dimethylamino)acryloyl)-3-ethyl-4-methylthiazol-2(3H)-one (240 mg, 1.00 mmol) in 2-methoxy ethanol (3 mL) was added NaOH (80.0 mg, 2.00 mmol). The reaction mixture was heated at 180° C. under microwave irradiation for 1 h, cooled to room temperature and concentrated under reduced pressure. The residue was purified by chromatography (silica gel, DCM ramping to DCM: MeOH=94:6) to give 94 as a yellow solid (108 mg, 26%). m.p. 181-182° C. $^1$H NMR ($CDCl_3$) 1.31 (t, 3H, J 7.0), 2.37 (s, 3H), 2.59 (s, 3H), 2.61 (t, 4H, J 5.0), 3.19 (t, 4H, J 5.0), 3.87 (q, 3H, J 7.0), 6.73 (d, 1H, J 5.0), 7.34 (dd, 1H, J 9.0 & 3.0), 8.03 (s, 1H), 8.22 (s, 1H), 8.22 (d, 1H, J 9.0), 8.40 (d, 1H, J 5.0). HRMS (ESI): m/z 412.1888 $[M+H]^+$; calcd. for $C_{20}H_{26}N_7OS^+$ $[M+H]^+$ 412.1914. Anal. RP-HPLC Method A: $t_R$ 8.36 mm, purity>99%; Method B: $t_R$ 3.23 mm, purity>95%.

5-(2-((5-(4-Acetylpiperazin-1-yl)pyridin-2-yl)amino) pyrimidin-4-yl)-4-methylthiazol-2(3H)-one (95)

Compound 95 was obtained as a brown solid (30 mg, 7%) by-product in the process of synthesising and purifying 1-(4-(6-((4-(4-methyl-2-(methylthio)thiazol-5-yl)pyrimidin-2-yl)amino)pyridin-3-yl)piperazin-1-yl)ethan-1-one. $^1$H NMR (DMSO-$1_6$) 2.04 (s, 3H), 2.42 (s, 3H), 3.07 (t, 2H, J 5.0), 3.14 (t, 2H, J 5.0), 3.58 (app m, 4H), 6.91 (d, 1H, J 5.5), 7.50 (dd, 1H, J 9.0 & 3.0), 8.02 (d, 1H, J 3.0), 8.05 (d, 1H, J 9.0), 8.42 (d, 1H, J 5.0), 9.56 (s, 1H). HRMS (ESI): m/z 412.1560 $[M+H]^+$; calcd. for $C_{19}H_{22}N_7O_2S^+$ $[M+H]^+$ 412.1550. Anal. RP-HPLC Method A: $t_R$ 9.03 min, purity>99%; Method B: $t_R$ 7.58 min, purity 100%.

3-Cyclopentyl-4-methyl-5-(2-((5-(piperazin-1-yl) pyridin-2-yl)amino)pyrimidin-4-yl)thiazol-2(3H)-one (96)

To a suspension of 5-(2-((5-(4-acetylpiperazin-1-yl)pyridin-2-yl)amino)pyrimidin-4-yl)-3-cyclopentyl-4-methylthiazol-2(3H)-one (100 mg, 0.21 mmol) in methanol HCl (32%, 3 mL) was added and reflexed overnight. The reaction mixture was concentrated and purified by FlashMaster Personal chromatography (silica gel, DCM ramping to DCM: MeOH)=9:1) to give 96 as a yellow solid (73 mg, 80%). $^1$H NMR ($CDCl_3$) δ 1.61-1.64 (m, 2H), 1.90-1.99 (m, 4H), 2.26-2.30 (m, 2H), 2.58 (s, 3H), 3.07 (t, 4H, J 2.5), 3.11 (t, 4H, J 3.0), 4.43 (m, 1H), 6.70 (d, 1H, J 5.5), 7.34 (dd, 1H, J 9.0 & 3.0), 7.90 (s, 1H), 8.00 (d, 1H, J 3.0), 8.22 (d, 1H, J 9.0), 8.39 (d, 1H, J 5.5). HRMS (ESI): m/z 438.2073 $[M+H]^+$; calcd. for $C_{22}H_{28}N_7OS^+$ $[M+H]^+$ 438.2071 Anal. RP-HPLC Method A: $t_R$ 13.52 min, purity>94%, Method B: $t_R$ 10.0 min, purity>99%.

4-Methyl-5-(2-((5-(piperazin-1-yl)pyridin-2-yl) amino)pyrimidin-4-yl)thiazol-2(3H)-one (97)

To a suspension of 5-(2-((5-(4-acetylpiperazin-1-yl)pyridin-2-yl)amino)pyrimidin-4-yl)-4-methylthiazol-2(3H)-one (50 mg, 0.13mmol) in methanol HCl (32%, 3 mL) was added and reflexed overnight. The reaction mixture was concentrated and purified by FlashMaster Personal chromatography (silica gel, DCM ramping to DCM:MeOH: $NH._4OH$)=9:1:1) to give 97 as a grey solid (41 mg, 91%). $^1$H NMR (DMSO-$d_6$) 2.42 (s, 3H), 3.00 (t, 4H, J 5.0), 3.16 (t, 4H, J 5.0), 6.91 (d, 1H, J 5.5), 7.47 (dd, 1H, J 9.0 & 3.0), 8.01 (d, 1H, J 3.0), 8.04 (d, 1H, J 9.0), 8.41 (d, 1H, J 5.5), 9.54 (s, 1H). HRMS (ESI): m/z 370.1433 $[M+H]^+$; calcd. for $C_{17}H_{20}N_7OS^+$ $[M+H]^+$ 370 1445. Anal. RP-HPLC Method A: $t_R$ 7.42 min, purity>97%; Method B: $t_R$ 3.59 min, purity>99%.

Example 2

Biological Activity

Kinase Assays

Eurofins Pharma Discovery or Reaction Biology Corporation Kinase Profiler services were used to measure inhibition of CDKs and other kinases by radiometric assay. Inhibition of CDK4/D1, CDK6/D3 and CDK9/T1 were also determined in-house using ADP Glo Kinase assays (Promega Corporation, Madison, USA). Briefly, the kinase reaction for CDK4/D1 and CDK6/D3 was performed with kinase reaction buffer (40 nM Tris base pH 7.5, 20 mM MgCl2, 0.4 mM DTT), 0.1 mg/ml BSA and RB-CTF substrate (retinoblastoma protein1 C-terminal fraction). For CDK9/CyclinT1, the kinase reaction was performed with standard assay buffer and Kinase Dilution Buffer and RBER-IRStide substrate. Serial dilutions of 1:3 were prepared for test compounds for 10 concentrations (from 10 μM to 0.5 nM). The kinase reactions were started by addition of ATP, incubated for 40 min at 37° C. and then stopped by adding 10 μL of ADP Glo reagent. After incubation at room temperature in the dark for 40 min, 20 μL of kinase detection reagent was added per well and incubated for 40 min. Luminescence was measured using an EnVision Multilabel plate reader (PerkinElmer, Buckinghamshire, UK). Positive and negative controls were perfonned in the presence and absence of CDK kinases, respectively. Half-maximal inhibition ($IC_{50}$) values were calculated using a 4-parameter logistic non-linear regression model with Graphpad prism (Version 6.0). Apparent inhibition constants ($K_i$) values were calculated from $K_m$ (ATP) and $IC_{50}$ values for the respective kinases. The results are shown in Table 2.

Cell Viability Assay

Compounds from Example 1 were subjected to a standard MTT (3-(4,5-dimethylthiazol-2-yl)-2,5-diphenyltetrazolium bromide) and resazurin assays on solid tumour cell lines and leukemia cell lines, respectively, as previously reported (Wang S et al., J Med Chem 47:1662-1675, 2004 and Diab S. et al. CheMedChem 9:962-972, 2014). Compound concentrations required to inhibit 50% of cell growth ($GI_{50}$)

were calculated using non-linear regression analysis. The results are shown in Tables 3 and 4.

Cell Cycle Analysis and Apoptosis

Cell cycle analysis and apoptosis studies were performed as described previously (Diab S. et al. CheMedChem 9:962-972, 2014; Teo T., et al. Cancer Letters, 357(2):612-623, 2015). Briefly, human acute myeloid leukaemia MV4-11 cells ($1\times10^5$) were seeded and incubated overnight at 37° C. and 5% $CO_2$. Cells were centrifuged at 300×g for 5 min upon treatment with inhibitor. Cell pellets were collected and fixed with 70% ethanol on ice for 15 min, followed by centrifugation at 300×g for 5 min. The collected pellets were incubated with staining solution (50 μg/mL PI, 0.1 mg/mL ribonuclease A, 0.05% Triton X-100) at 37° C. for an hour and analysed with Gallios flow cytometer. $1\times10^5$ of the remaining cells were then used in an apoptotic assay with Annexin V-FITC Apoptosis Detection Kit. The samples were analysed by FACS within one hour of staining. Data were analysed using Kaluza v1.2.

Figure 2:
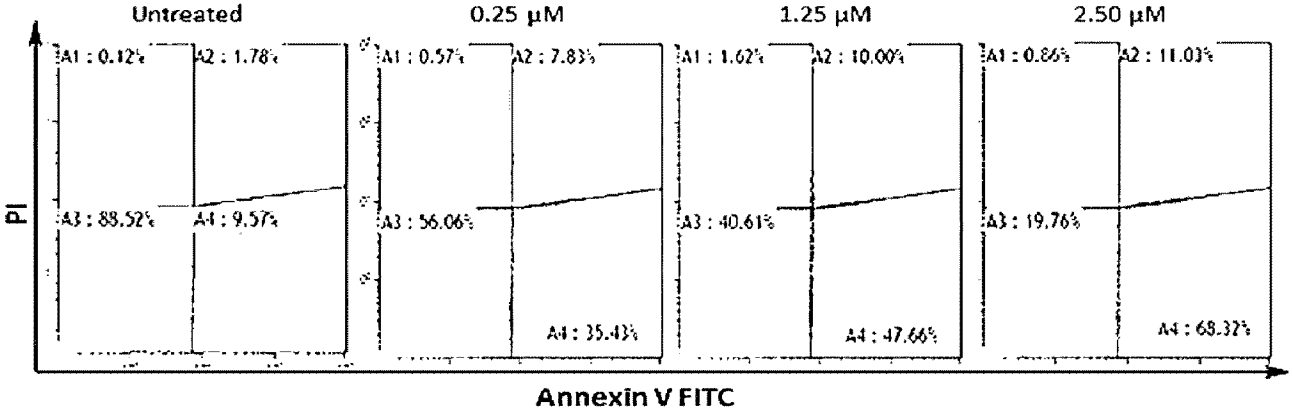
FIG. 2 provides graphical results obtained from an apoptotic assay using a representative compound of the present invention (ie compound 47 described herein), wherein MV4-11 cells were treated for 24 hours with 47 at concentrations of 0.25 μM, 1.25 μM and 2.50 μM.

In an example shown in FIG. 1, MV4-11 cells were treated with compound 60 for 24 hat the concentrations shown. It was found that compound 60 arrested cells in the G1 phase of the cell-cycle in a dose-dependent manner, confirming its inhibitory activity against cellular CDK4/6. Treatment of cancer cells with compounds resulted in apoptosis as represented by the sum of early (annexin-V+/PI−) and late (annexin-V+/PI+) apoptosis. A representative example is shown in FIG. 2.

Example 3

Pharmacokinetics

For pharmacokinetic measurements, healthy male adult Balb/C mice (weighing 20-25 g) or Wistar Rat (weighing 250-350 g) were split into weight matched groups of 3 per group. Compound was administered IV (2 mg/kg for mice, 5 mg/kg for rats) via the tail vein or by oral gavage (20 mg/kg). Blood samples were collected from animals by jugular vein cannula (rats) or under anaesthesia by cardiac puncture (mice) at time zero and at intervals up to 24 h. Harvested blood was centrifuged at 7000×G for 2 minutes, and the plasma aspirated and frozen at −20° C. until analysis. Quantitative analysis of compound in plasma was carried out using LC-MS/MS methods. Pharmacokinetic data derived using Phoenix WinNonlin 6.4® non-compartmental analysis. Oral bioavailability (% F) was calculated by taking the ratio of dose-normalised AUC values from oral versus parenteral (IV) dosing. Pharmacokinetic profiles of example compounds are shown in Table 5.

TABLE 2

Inhibition of cyclin-dependant kinases

| | CDK inhibition $K_i$ (μM) or % remaining enzymatic activity at 10 μM | | | | | |
|---|---|---|---|---|---|---|
| Compound | CDK1B | CDK 2A | CDK4D1 | CDK6D3 | CDK7H | CDK9T1 |
| 1 | >5 | >5 | 0.081 | 0.590 | >5 | >5 |
| 2 | >5 | >5 | 0.055 | 0.245 | >5 | >5 |
| 3 | >5 | 1.935 | 0.030 | 0.170 | >5 | >5 |
| 4 | >5 | >5 | 0.031 | 0.117 | >5 | 2.037 |
| 5 | >5 | >5 | 0.070 | 0.027 | >5 | >5 |
| 6 | >5 | >5 | 0.119 | 0.201 | >5 | >5 |
| 7 | >5 | 1.71 | 0.059 | 0.237 | >5 | >5 |
| 8 | >5 | 1.82 | 0.024 | 0.980 | >5 | >5 |
| 9 | >5 | 1.80 | 0.010 | 1.670 | >5 | >5 |
| 10 | >5 | >5 | 0.290 | ND* | >5 | >5 |
| 11 | >5 | >5 | 0.250 | ND | >5 | >5 |
| 12 | >5 | 2.34 | 0.180 | ND | >5 | >5 |
| 13 | 3.740 | 0.241 | 0.011 | 0.030 | >5 | >5 |
| 14 | 3.410 | 0.287 | 0.010 | 0.029 | >5 | 4.180 |
| 15 | 3.095 | 0.465 | 0.005 | 0.025 | >5 | >5 |
| 16 | 4.850 | 0.246 | 0.062 | 0.209 | >5 | >5 |
| 17 | 1.440 | 0.060 | 0.001 | 0.004 | 4.690 | 1.725 |
| 18 | >5 | 0.775 | 0.028 | 0.394 | >5 | >10 |
| 19 | >5 | 3.645 | 0.310 | 0.935 | >5 | 4.764 |
| 20 | >5 | 0.720 | 0.005 | 0.020 | >5 | 4.530 |
| 21 | >5 | 2.700 | 0.007 | 0.042 | >5 | >5 |
| 22 | >5 | 4.760 | 0.190 | 1.955 | 86% | 80% |
| 23 | >5 | 0.180 | 0.030 | 0.200 | >5 | >5 |
| 24 | 3.990 | 0.180 | 0.001 | 0.015 | >5 | 4.610 |
| 25 | >5 | 0.075 | 0.005 | 0.020 | >5 | >5 |
| 26 | >5 | 0.889 | 0.006 | 0.114 | >5 | 2.850 |
| 27 | 56% | 34% | 0.001 | 0.040 | 39% | 11% |
| 28 | 1.360 | 0.236 | 0.004 | 0.032 | >5 | 0.784 |
| 29 | 3.205 | 0.650 | 0.005 | 0.050 | >5 | 1.820 |
| 30 | 66% | 36% | 0.004 | 0.032 | 43% | 9% |
| 31 | >5 | 0.365 | 0.002 | 0.010 | >5 | 1.905 |
| 32 | >5 | 0.665 | 0.005 | 0.020 | >5 | 2.925 |
| 33 | 3.101 | 0.310 | 0.578 | 3.032 | >5 | >5 |
| 34 | >5 | 4.466 | 0.004 | 0.030 | >5 | >5 |
| 35 | 1.820 | 0.178 | 0.017 | 0.046 | >5 | 4.070 |
| 36 | >5 | 0.459 | 0.020 | 0.610 | >5 | >5 |
| 37 | >5 | 0.201 | 0.004 | 0.064 | >5 | >5 |
| 38 | 3.315 | 0.100 | 0.005 | 0.030 | >5 | >5 |
| 39 | >5 | >5 | 0.169 | 2.710 | >5 | >5 |
| 40 | >5 | >5 | 0.016 | 0.036 | >5 | 0.999 |
| 41 | 0.133 | 0.037 | 0.006 | 0.225 | 0.067 | 0.117 |
| 42 | 0.089 | 0.017 | 0.001 | 0.036 | 0.101 | 0.034 |

TABLE 2-continued

| Inhibition of cyclin-dependant kinases | | | | | | |
|---|---|---|---|---|---|---|
| | CDK inhibition $K_i$ (μM) or % remaining enzymatic activity at 10 μM | | | | | |
| Compound | CDK1B | CDK 2A | CDK4D1 | CDK6D3 | CDK7H | CDK9T1 |
| 43 | >5 | 0.903 | 0.021 | 0.056 | >5 | >5 |
| 44 | >5 | 0.335 | 0.004 | 0.040 | >5 | >5 |
| 45 | >5 | 1.430 | 0.030 | 0.154 | >5 | >5 |
| 46 | >5 | 1.39 | 0.002 | 0.055 | >5 | 4.36 |
| 47 | >5 | 3.335 | 0.002 | 0.279 | >5 | >5 |
| 48 | >5 | 0.976 | 0.087 | 0.234 | >5 | >5 |
| 49 | >5 | 1.04 | 0.024 | 0.366 | >5 | >5 |
| 50 | >5 | 0.069 | 0.044 | ND | >5 | >5 |
| 51 | ND | ND | >5 | ND | ND | ND |
| 52 | 0.580 | 0.076 | 0.037 | 0.297 | >5 | >5 |
| 53 | 2.370 | 0.206 | 0.003 | 0.032 | >5 | 3.037 |
| 54 | ND | ND | >5 | ND | ND | ND |
| 55 | 3.140 | 0.240 | 0.005 | 0.011 | 0.775 | 2.420 |
| 56 | 3.815 | 0.399 | 0.003 | 0.015 | 0.760 | 0.773 |
| 57 | 2.695 | 0.200 | 0.021 | 0.105 | 4.385 | 3.717 |
| 58 | >5 | 0.127 | 0.041 | 0.082 | >5 | >5 |
| 59 | >5 | 0.800 | 0.016 | 0.028 | 1.160 | 0.925 |
| 60 | >5 | >5 | 0.001 | 0.034 | 1.108 | 0.220 |
| 61 | 2.235 | 0.256 | 0.003 | 0.007 | 0.790 | 0.787 |
| 62 | 0.220 | 0.022 | 0.008 | 0.002 | 0.194 | 0.258 |
| 63 | 2.675 | 0.206 | 0.002 | 0.009 | 0.865 | 0.180 |
| 64 | 2.330 | 0.103 | 0.001 | 0.003 | 2.020 | 0.505 |
| 65 | 0.241 | 0.022 | 0.001 | 0.003 | 0.189 | 0.831 |
| 66 | 3.02 | 0.355 | 0.002 | 0.011 | 0.780 | 0.141 |
| 67 | >5 | 0.349 | 0.002 | 0.006 | 0.685 | >5 |
| 68 | 3.252 | 0.776 | 0.006 | 0.093 | 3.453 | 0.286 |
| 69 | >5 | 0.228 | 0.034 | 0.023 | >5 | 4.990 |
| 70 | 0.297 | 0.014 | 0.004 | 0.006 | 2.615 | >5 |
| 71 | >5 | 2.940 | 0.005 | 0.029 | >5 | >5 |
| 72 | 4.350 | 0.104 | 0.006 | 0.020 | >5 | >5 |
| 73 | >5 | 0.154 | 0.008 | 0.011 | >5 | >5 |
| 74 | 1.230 | 0.181 | 0.003 | 0.133 | 1.187 | 0.173 |
| 75 | >5 | >5 | 0.070 | 0.257 | >5 | >5 |
| 76 | 4.070 | 0.278 | 0.001 | 0.008 | 0.282 | 0.508 |
| 77 | 1.100 | 0.077 | 0.007 | 0.055 | 2.640 | 1.321 |
| 78 | — | — | 0.570 | — | — | >5 |
| 79 | 0.345 | 0.015 | 0.011 | 0.007 | 1.900 | >5 |
| 80 | >5 | 1.150 | 0.001 | 0.031 | >5 | 1.091 |
| 81 | >5 | 0.417 | 0.014 | 0.010 | 0.815 | 0.679 |
| 82 | >5 | 0.348 | 0.039 | 0.101 | >5 | >5 |
| 83 | >5 | 0.416 | 0.006 | 0.009 | 0.211 | 1.984 |
| 84 | >5 | 0.620 | 0.003 | 0.014 | 0.630 | 3.570 |
| 85 | 1.390 | 0.174 | 0.002 | 0.010 | 3.20 | 1.801 |
| 86 | >5 | 0.476 | 0.002 | 0.010 | >5 | 1.800 |
| 87 | 3.170 | 0.121 | 0.010 | 0.031 | >5 | >5 |
| 88 | >15 | >5 | 0.071 | 0.539 | >5 | >5 |
| 89 | 2.040 | >5 | 0.005 | 0.066 | 1.660 | 0.436 |
| 90 | >5 | >5 | 0.019 | 0.485 | >5 | >5 |
| 91 | >5 | 1.040 | 0.026 | 0.100 | >5 | 2.00 |
| 92 | 51% | 61% | 0.027 | 0.155 | 24% | 0.950 |
| 93 | 71% | 77% | 0.255 | 0.915 | 52% | 0.840 |
| 94 | 3.660 | 1.340 | 0.033 | 0.320 | 1.260 | 1.580 |
| 95 | 55% | 40% | ND | 25% | 68% | 17% |
| 96 | 63% | 61% | ND | 11% | 22% | 15% |
| 97 | 58% | 54% | ND | 12% | 24% | 3% |

TABLE 3

| Anti-proliferative activity (72 h, $GI_{50}$ μM) of example compounds | | |
|---|---|---|
| Compound No. | MV4-11 | MDA-MB-453 |
| 1 | 1.099 ± 0.345 | >10 |
| 2 | 1.021 ± 0.007 | >10 |
| 3 | 0.053 ± 0.003 | 0.378 ± 0.029 |
| 4 | 0.296 ± 0.287 | 1.973 ± 0.404 |
| 5 | 0.500 ± 0.247 | 0.914 ± 0.098 |
| 6 | 2.129 ± 0.969 | >10 |
| 7 | 0.606 ± 0.150 | 3.860 ± 0.220 |
| 8 | 0.750 ± 0.246 | 3.009 ± 0.705 |
| 9 | 0.591 ± 0.083 | 3.320 ± 0.576 |
| 10 | 5.372 ± 1.685 | >10 |

TABLE 3-continued

| Anti-proliferative activity (72 h, $GI_{50}$ μM) of example compounds | | |
|---|---|---|
| Compound No. | MV4-11 | MDA-MB-453 |
| 11 | >10 | >10 |
| 12 | 5.294 ± 0.811 | >10 |
| 13 | 0.029 ± 0.019 | 0.703 ± 0.071 |
| 14 | 0.596 ± 0.231 | >10 |
| 15 | 0.063 ± 0.026 | 0.542 ± 0.065 |
| 16 | 0.457 ± 0.122 | >10 |
| 17 | 0.649 ± 0.024 | 1.054 ± 0.203 |
| 18 | 0.418 ± 0.023 | 0.166 ± 0.117 |
| 19 | 3.518 ± 1.044 | >10 |
| 20 | 0.671 ± 0.091 | 3.137 ± 0.173 |

TABLE 3-continued

| Anti-proliferative activity (72 h, $GI_{50}$ μM) of example compounds | | |
|---|---|---|
| Compound No. | MV4-11 | MDA-MB-453 |
| 21 | 0.456 ± 0.066 | 7.156 ± 0.886 |
| 22 | 2.511 ± 0.432 | >10 |
| 23 | 0.073 ± 0.025 | 0.461 ± 0.059 |
| 24 | 0.066 ± 0.019 | 4.877 ± 0.214 |
| 25 | 0.537 ± 0.117 | 0.514 ± 0.050 |
| 26 | 0.259 ± 0.241 | — |
| 27 | 0.014 ± 0.006 | — |
| 28 | 0.012 ± 0.003 | 0.248 ± 0.044 |
| 29 | 0.297 ± 0.061 | 0.544 ± 0.078 |
| 30 | 0.056 ± 0.004 | — |
| 31 | 0.011 ± 0.004 | 0.381 ± 0.096 |
| 32 | 0.065 ± 0.002 | 0.528 ± 0.046 |
| 33 | 0.154 ± 0.074 | 5.840 ± 0.279 |
| 34 | 0.174 ± 0.022 | 0.813 ± 0.022 |
| 35 | 0.035 ± 0.004 | 4.912 ± 0.432 |
| 36 | 0.643 ± 0.018 | — |
| 37 | 0.465 ± 0.129 | — |
| 38 | 0.069 ± 0.005 | 5.407 ± 0.801 |
| 39 | 45.90 ± 2.520 | — |
| 40 | 0.084 ± 0.008 | — |
| 41 | 0.038 ± 0.006 | — |
| 42 | 0.037 ± 0.006 | — |
| 43 | 0.011 ± 0.021 | 0.894 ± 0.091 |
| 44 | 0.048 ± 0.004 | 0.237 ± 0.044 |
| 45 | 0.092 ± 0.004 | 2.102 ± 0.787 |
| 46 | 0.073 ± 0.010 | 0.638 ± 0.042 |
| 47 | 0.107 ± 0.022 | 0.349 ± 0.036 |
| 48 | 0.537 ± 0.133 | 4.718 ± 0.715 |
| 49 | 0.208 ± 0.030 | 2.369 ± 0.026 |
| 50 | 4.675 ± 0.298 | 5.358 ± 0.501 |
| 51 | 0.606 ± 0.038 | 0.463 ± 0.075 |
| 52 | 0.425 ± 0.073 | 0.660 ± 0.092 |
| 53 | 0.080 ± 0.013 | 0.362 ± 0.003 |
| 54 | 2.158 ± 0.431 | 2.941 ± 0.507 |
| 55 | 0.093 ± 0.010 | 0.031 ± 0.002 |
| 56 | 0.075 ± 0.005 | 0.618 ± 0.193 |
| 57 | 2.071 ± 0.321 | 0.344 ± 0.126 |
| 58 | 0.032 ± 0.003 | 0.115 ± 0.024 |

TABLE 3-continued

| Anti-proliferative activity (72 h, $GI_{50}$ μM) of example compounds | | |
|---|---|---|
| Compound No. | MV4-11 | MDA-MB-453 |
| 59 | 0.255 ± 0.085 | 0.938 ± 0.068 |
| 60 | 0.023 ± 0.024 | 0.070 ± 0.013 |
| 61 | 0.053 ± 0.004 | 0.780 ± 0.598 |
| 62 | 0.002 ± 0.001 | 0.081 ± 0.039 |
| 63 | 0.009 ± 0.000 | 0.130 ± 0.011 |
| 64 | 0.073 ± 0.028 | 0.202 ± 0.030 |
| 65 | 0.001 ± 0.001 | 0.420 ± 0.120 |
| 66 | 0.009 ± 0.001 | 0.287 ± 0.070 |
| 67 | 0.013 ± 0.002 | 0.066 ± 0.019 |
| 68 | 0.024 ± 0.028 | 0.591 ± 0.256 |
| 69 | 0.015 ± 0.002 | 8.107 ± 1.147 |
| 70 | 0.012 ± 0.001 | 0.077 ± 0.001 |
| 71 | 0.335 ± 0.184 | 3.683 ± 0.285 |
| 72 | 0.290 ± 0.062 | 1.437 ± 0.304 |
| 73 | 0.069 ± 0.013 | 0.415 ± 0.103 |
| 74 | 0.022 ± 0.002 | 0.055 ± 0.012 |
| 75 | 0.191 ± 0.029 | 7.035 ± 0.710 |
| 76 | 0.029 ± 0.002 | 0.102 ± 0.117 |
| 77 | 0.176 ± 0.009 | 0.215 ± 0.052 |
| 78 | 0.300 ± 0.035 | 4.379 ± 0.691 |
| 79 | 0.004 ± 0.001 | 0.336 ± 0.188 |
| 80 | 0.454 ± 0.040 | 0.356 ± 0.024 |
| 81 | 0.029 ± 0.002 | 0.083 ± 0.009 |
| 82 | 2.628 ± 0.582 | 2.813 ± 0.089 |
| 83 | 0.019 ± 0.003 | 0.004 ± 0.002 |
| 84 | 0.010 ± 0.002 | 0.622 ± 0.208 |
| 85 | 0.285 ± 0.041 | 0.402 ± 0.006 |
| 86 | 0.020 ± 0.015 | 3.360 ± 0.286 |
| 87 | 0.328 ± 0.007 | 6.864 ± 0.798 |
| 88 | 0.714 ± 0.179 | 0.373 ± 0.117 |
| 89 | 0.056 ± 0.011 | 0.279 ± 0.044 |
| 90 | 0.508 ± 0.042 | 0.494 ± 0.081 |
| 91 | 0.421 ± 0.044 | 0.150 ± 0.029 |
| 92 | 0.752 ± 0.033 | 3.327 ± 0.864 |
| 93 | 3.725 ± 0.357 | >10 |
| 94 | 1.829 ± 0.194 | >10 |
| 95 | 2.238 ± 0.043 | >10 |
| 96 | 0.792 ± 0.074 | 2.858 ± 0.988 |
| 97 | 1.512 ± 0.802 | >10 |

TABLE 4

| Antiproliferative activity (72 h, $GI_{50}$ μM) of representative compounds. | | | | | |
|---|---|---|---|---|---|
| | Leukemia | | Ovarian | Medulloblastoma | |
| Compound | KG-1 | MOLM-13 | A2780 | D458 | D283 |
| 9 | 0.047 ± 0.015 | 0.293 ± 0.028 | — | — | — |
| 29 | — | — | 0.282 ± 0.058 | 0.326 ± 0.029 | 0.335 ± 0.097 |
| 31 | — | — | 0.094 ± 0.001 | 0.645 ± 0.097 | 0.489 ± 0.022 |
| 34 | 0.112 ± 0.045 | 0.408 ± 0.025 | — | — | — |
| 46 | 0.005 ± 0.004 | 0.098 ± 0.012 | — | — | — |
| 47 | 0.006 ± 0.001 | 0.076 ± 0.008 | — | — | — |
| 60 | — | — | 0.081 ± 0.001 | 0.321 ± 0.068 | 0.124 ± 0.020 |
| 64 | — | — | 0.056 ± 0.007 | 0.457 ± 0.171 | 0.077 ± 0.006 |
| 86 | — | — | 0.072 ± 0.020 | 0.617 ± 0.112 | 0.358 ± 0.100 |

TABLE 5

| Pharmacokinetic properties of representative compounds 60, 71, and 34 | | | | |
|---|---|---|---|---|
| | Compounds (po, 20 mg/kg in rat) | | | |
| Pharmacokinetic parameter | 60[a] | 71 | 71[b] | 34 |
| Cmax (μM) | 0.5 | 1.4 | 1.6 | 0.6 |
| AUC (μM · hr) | 6.6 | 15.9 | 5.9 | 10.2 |
| $t_{1/2}$ (hr) | 16.4 | 2.8 | 5.0 | 4.6 |
| Oral bioavailability (F %) | 51 | 27 | 100 | 39 |

[a]40 mg/kg in rat,
[b]10 mg/kg in mice.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

Please note that the following claims are provisional claims only, and are provided as examples of possible claims and are not intended to limit the scope of what may be claimed in any future patent applications based on the present application. Integers may be added to or omitted from the example claims at a later date so as to further define or re-define the invention.

The invention claimed is:

[1. A compound of formula I shown below:

I

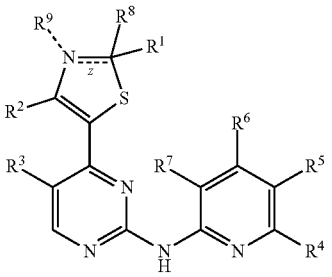

]

wherein:

z represents an optional bond such that the bond between N and the adjacent carbon atom can be a single or double bond;

$R^1$, $R^4$, $R^6$ and $R^7$ are each independently selected from the group consisting of H, alkyl, alkyl- $R^{10}$, aryl, aryl-$R^{10}$, aralkyl, aralkyl-$R^{11}$, halogen, $NO_2$, CN, $CF_3$, OH, O-alkyl, $COR^{10}$, $COOR^{10}$, O-aryl, O—$R^{10}$, $NH_2$, NH-alkyl, NH-aryl, N-$(alkyl)_2$, N-$(aryl)_2$, N-(alkyl)(aryl), NH—$R^{10}$, N—$(R^{10})(R^{11})$, N-(alkyl)($R^{10}$), N-(aryl)($R^{10}$), SH-alkyl, SH-aryl, S-$(alkyl)_2$, S-$(aryl)_2$, S-(alkyl)(aryl), SH—$R^{10}$,S—$(R^{10})(R^{11})$, S-(alkyl)($R^{10}$), S-(aryl)($R^{10}$), COOH, $CONH_2$, CONH-alkyl, CONH-aryl, CON-(alkyl)($R^{10}$), CON(aryl)($R^{10}$), CONH—$R^{10}$, CON—$(R^{10})(R^{11})$, $SO_3H$, $SO_2$-alkyl, $SO_2$-alkyl-$R^{10}$, $SO_2$-aryl, $SO_2$-aryl-$R^{10}$, $SO_2NH_2$, $SO_2NH$—$R^{10}$, $SO_2N$—$(R^{10})(R^{11})$, $CF_3$, CO-alkyl, CO-alkyl-$R^{10}$, CO-aryl, CO-aryl-$R^{10}$ and $R^{12}$, wherein said alkyl, aryl and aralkyl groups may be optionally substituted with one or more groups selected from halogen, CN, OH, O-methyl, $NH_2$, COOH, $CONH_2$ and $CF_3$, and wherein when bond z is absent, $R^1$ is taken together with $R^8$ and is =O or =S;

$R^2$ is alkyl;

$R^3$ is H, $C_{1-6}$ alkyl, CN or halogen;

$R^5$ is selected from alkyl, alkyl-$R^{10}$, aryl, aryl-$R^{10}$, aralkyl, aralkyl-$R^{11}$, halogen, $NO_2$, CN, $CF_3$, OH, O-alkyl, $COR^{10}$, $COOR^{10}$, O-aryl, O—$R^{10}$, $NH_2$, NH-alkyl, NH-aryl, N-$(alkyl)_2$, N-$(aryl)_2$, N-(alkyl)(aryl), NH—$R^{10}$, N—$(R^{10})(R^{11})$, N-(alkyl)($R^{10}$), N-(aryl)($R^{10}$), SH-alkyl, SH-aryl, S-$(alkyl)_2$, S-$(aryl)_2$, S-(alkyl)(aryl), SH—$R^{10}$, S—$(R^{10})(R^{11})$, S-(alkyl)($R^{10}$), S-(aryl)($R^{10}$), COOH, $CONH_2$, CONH-alkyl, CONH-aryl, CON-(alkyl)($R^{10}$), CON(aryl)($R^{10}$), CONH—$R^{10}$, CON—$(R^{10})(R^{11})$, $SO_3H$, $SO_2$-alkyl, $SO_2$-alkyl-$R^{10}$, $SO_2$-aryl, $SO_2$-aryl-$R^{10}$, $SO_2NH_2$, $SO_2NH$—$R^{10}$, $SO_2N$—$(R^{10})(R^{11})$, $CF_3$, CO-alkyl, CO-alkyl-$R^{10}$, CO-aryl, CO-aryl-$R^{10}$ and $R^{12}$, wherein said alkyl, aryl and aralkyl groups may be optionally substituted with one or more groups selected from halogen, CN, OH, O-methyl, $NH_2$, COOH, $CONH_2$ and $CF_3$;

$R^8$ is together with $R^1$=O or =S when bond z is absent, or is not present when bond z is present; $R^9$ is H, alkyl, aryl or heterocyclic group when bond z is absent, or is not present when bond z is present; and $R^{10}$, $R^{11}$ and $R^{12}$ are independently selected from water solubilising groups;

or a pharmaceutically acceptable salt or solvate thereof.]

[2. A compound according to claim 1, wherein the compound is of formula II:

II

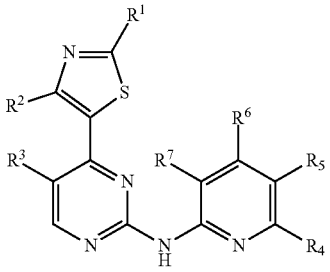

]

wherein $R^1$, $R^4$, $R^6$ and $R^7$ are each independently selected from the group consisting of H, alkyl, aryl, aralkyl, halogen, $NO_2$, CN, $CF_3$, OH, O-alkyl, O-aryl, $NH_2$, NH-alkyl, NH-aryl, N-$(alkyl)_2$, N-(aryl), N-(alkyl)(aryl), SH-alkyl, SH-aryl, S-$(alkyl)_2$, S-$(aryl)_2$, S-(alkyl)(aryl), COOH, $CONH_2$, CONH-alkyl, CONH-aryl, $SO_3H$, $SO_2$-alkyl, $SO_2$-aryl, $SO_2NH_2$, $CF_3$, CO-alkyl, and CO-aryl, wherein said alkyl, aryl and aralkyl groups may be optionally substituted with one or more groups selected from halogen, CN, OH, O-methyl, $NH_2$, COOH, $CONH_2$ and $CF_3$;

$R^2$ is alkyl;

$R^3$ is H, $C_{1-6}$ alkyl, CN or halogen; and $R^5$ is $R^{12}$, or a pharmaceutically acceptable salt or solvate thereof.]

[3. A compound according to claim 1, wherein $R^1$ is H, $C_{1-6}$ alkyl, aryl, NH—$C_{1-6}$alkyl, N($C_{1-6}$ alkyl)$_2$, NH-aryl, N—($C_{1-6}$ alkyl)(aryl) or SH—$C_{1-6}$ alkyl.]

[4. A compound according to claim 1, wherein the compound is of formula III:

[ III

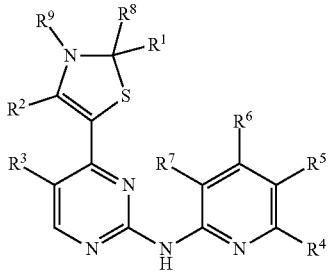

]

wherein $R^2$, $R^3$, $R^4$, $R^5$, $R^6$ and $R^7$ are as defined in claim 1, $R^8$ is together with $R^1$ is =O or =S, and $R^9$ is H, alkyl, aryl or heterocyclic group.]

[5. A compound according to claim 2, wherein $R^2$ is $C_{1-6}$ alkyl.]

[6. A compound according to claim 2, wherein $R^3$ is $C_{1-3}$ alkyl, CN or halogen.]

[7. A compound according to claim 2, wherein $R^4$ is H, O—$C_{1-6}$ alkyl or halogen.]

[8. A compound according to claim 2, wherein $R^{12}$ is N—, O— and/or S-containing heterocyclic groups substituted with one or more hydroxyl or amino groups, aliphatic and aryl groups comprising one or more carboxamide, sulfoxide, sulfone or sulfonamide groups, and halogenated alkylcarbonyl groups.]

[9. A compound according to claim 8, wherein $R^{12}$ is selected from the following:

[

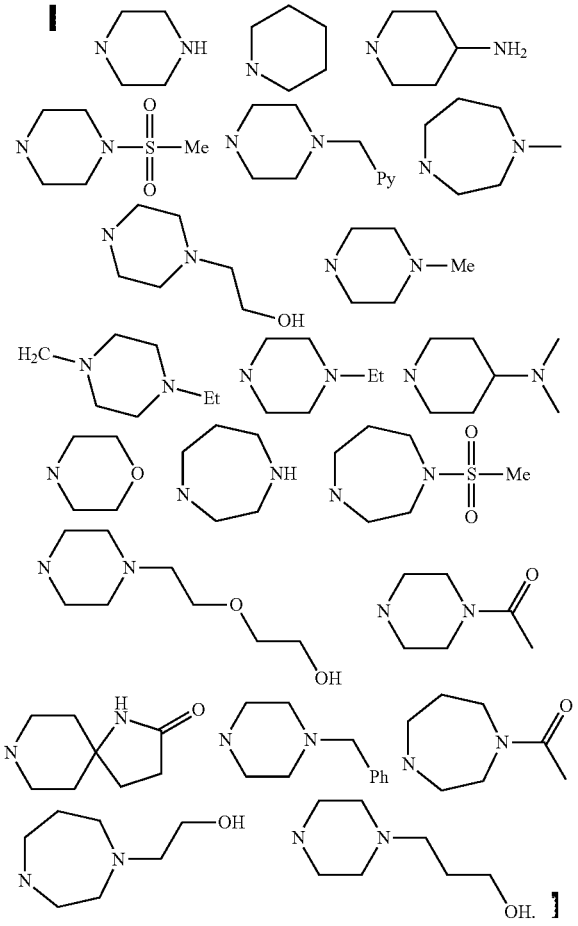

]

]

[10. A compound according to claim 8, wherein $R^6$ is H.]

[11. A compound according to claim 8, wherein $R^6$ is $R^{12}$ and $R^5$ is H.]

[12. A compound according to claim 8, wherein $R^{12}$ is an N—, O— and/or S-containing heterocyclic group substituted with one or more hydroxyl, amino or alkoxy group.]

[13. A compound according to claim 8, wherein $R^{12}$ is selected from the following:

[

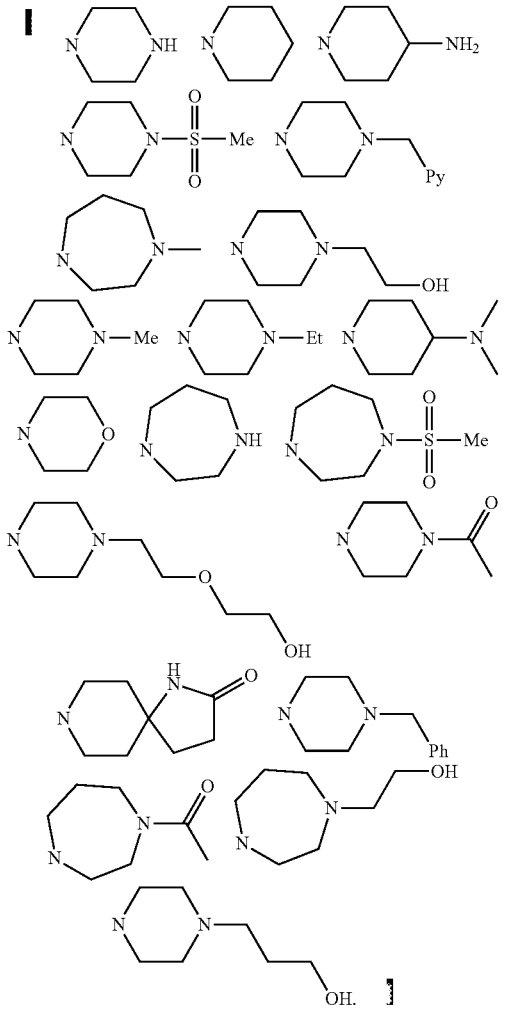

]

]

[14. A compound according to claim 8, wherein $R^{12}$ is selected from the following:

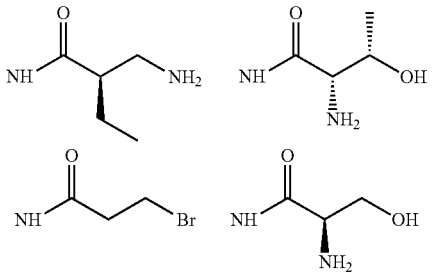

-continued

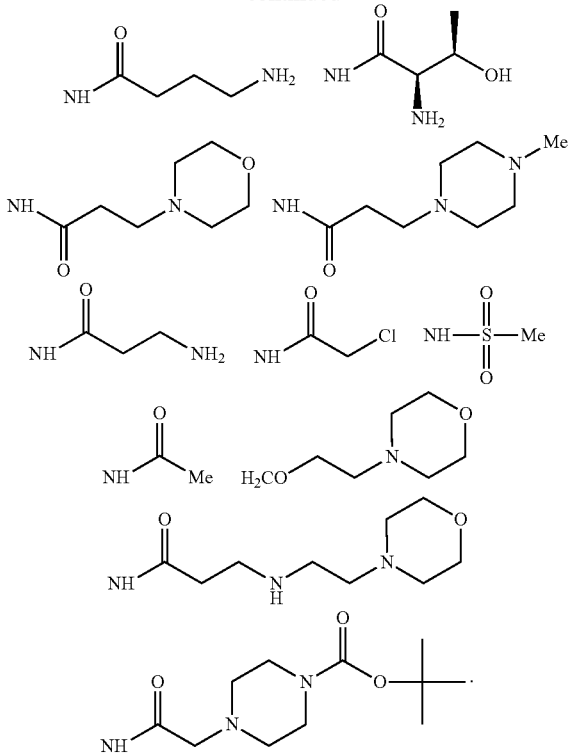

]

[15. A compound according claim 1, wherein $R^7$ is H.]

[16. A method of treating cancer in a subject, the method comprising administering to said subject a therapeutically effective amount of the compound of claim 1 or a pharmaceutically acceptable salt or solvate thereof, optionally in combination with a pharmaceutically acceptable carrier, diluent and/or excipient.]

[17. The method of claim 16, wherein the cancer is selected from those characterized by over-expression of CDK4 and/or CDK6.]

[18. The method of claim 17, wherein the cancer is selected from the group consisting of cancers of lung, breast, brain, central nervous system and colorectal cancer.]

[19. The method of claim 17, wherein the cancer is selected from the group consisting of acute lymphoblastic leukemia (ALL), acute myeloid leukemia (AML), and chronic lymphocytic leukemia (CLL).]

[20. A pharmaceutical composition or medicament comprising the compound of claim 2 and at least one pharmaceutically acceptable carrier, diluent or excipient.]

[21. A method for modulating protein kinase activity in a cell, comprising introducing to or contacting said cell with an effective amount of the compound of claim 2 or a pharmaceutically acceptable salt or solvate thereof.]

[22. A compound according to claim 2, wherein $R^2$ is $C_{1-3}$ alkyl.]

[23. A compound according to claim 2, wherein $R^2$ is methyl.]

[24. A compound according to claim 2, wherein $R^3$ is halogen.]

[25. A compound according to claim 24, wherein $R^3$ is F.]

[26. A compound according to claim 2, wherein $R^1$ is NH—$C_{1-6}$ alkyl or N($C_{1-6}$ alkyl)$_2$.]

[27. A compound according to claim 26, wherein $R^1$ is NH-methyl, NH-cyclopentyl or N(methyl)$_2$.]

[28. A compound according to claim 2, wherein the compound is:

5-(5-fluoro-2-((5-(4-methylpiperazin-1-yl)pyridin-2-yl)amino)pyrimidin-4-yl)-N,N,4-trimethylthiazol-2-amine, 5-(2-((5 -(4-(dimethylamino)piperidin-1-yl)pyridin-2-yl)amino)-5-fluoropyrimidin-4-yl)-N,4-dimethylthiazol-2-amine, N-cyclopentyl-5-(2-((5-(4-(dimethylamino)piperidin-1-yl)pyridin-2-yl)amino)-5-fluoropyrimidin-4-yl)-4-methylthiazol-2-amine, or N-cyclopentyl-5-(2-((5-((4-ethylpiperazin-1-yl)mcthyppyridin-2-yl)amino)-5-fluoropyrimidin-4-yl)-4-methylthiazol-2-amine.]

[29. A pharmaceutical composition or medicament comprising a compound selected from 5-(5-fluoro-2-((5-(4-methylpiperazin-1 -yl)pyridin-2-yl)amino)pyrimidin-4-yl)-N,N,4-trimethylthiazol-2-amine, 5-(2-((5-(4-(dimethylamino)piperidin-1-yl)pyridin-2-yl)amino)-5-fluoropyrimidin-4-yl)-N,4-dimethylthiazol-2-amine, N-cyclopentyl-5-(2-((5-(4-(dimethylamino)piperidin-1-yl)pyridin-2-yl)amino)-5-fluoropyrimidin-4-yl)-4-methylthiazol-2-amine, and N-cyclopentyl-5-(2-((5-((4-ethylpiperazin-1-yl)mcthyppyridin-2-yl)amino)-5-fluoropyrimidin-4-yl)-4-methylthiazol-2-amine; and at least one pharmaceutically acceptable carrier, diluent or excipient.]

*30. A compound which is 5-(2-((5-(4-(dimethylamino)piperidin-1-yl)pyridin-2-yl)amino)-5-fluoropyrimidin-4-yl)-N,4-dimethylthiazol-2-amine, or a pharmaceutically acceptable salt or solvate thereof.*

*31. A pharmaceutical composition comprising the compound according to claim 30, and at least one pharmaceutically acceptable carrier, diluent or excipient.*

*32. A method of treating cancer in a subject, the method comprising administering to said subject a therapeutically effective amount of the compound of claim 30 or a pharmaceutically acceptable salt or solvate thereof, optionally in combination with a pharmaceutically acceptable carrier, diluent and/or excipient.*

*33. The method according to claim 32, wherein the cancer is characterized by over-expression of CDK4.*

*34. The method according to claim 32, wherein the cancer is selected from the group consisting of biliary tract cancer, brain cancer, breast cancer, cervical cancer, choriocarcinoma, colonic cancer, endometrial cancer, oesophageal cancer, gastric cancer, haematological neoplasms, intraepithelial neoplasms, liver cancer, lung cancer, lymphomas, neuroblastomas, oral cancer, ovarian cancer, pancreatic cancer, prostate cancer, colorectal cancer, sarcomas, skin cancer, testicular cancer, stromal tumours, germ cell tumours, thyroid cancer, and renal cancer.*

*35. The method according to claim 32, wherein the cancer is selected from the group consisting of cancers of lung, breast, brain, central nervous system, ovarian cancer and colorectal cancer.*

*36. The method according to claim 32, wherein the cancer is selected from the group consisting of acute lymphoblastic leukemia (ALL), acute myeloid leukaemia (AML), and chronic lymphocytic leukemia (CLL).*

*37. The method according to claim 32, wherein the cancer is breast cancer.*

*38. The method according to claim 32, wherein the cancer is ovarian cancer.*

*39. The method according to claim 32, wherein the cancer is a liposarcoma.*

*40. The method according to claim 32, wherein the cancer is lung cancer.*

*41. A method for modulating protein kinase activity in a cell, comprising introducing to or contacting said cell with an effective amount of the compound of claim 30 or a pharmaceutically acceptable salt or solvate thereof.*

* * * * *